US011260018B2

(12) United States Patent
Jordan et al.

(10) Patent No.: US 11,260,018 B2
(45) Date of Patent: Mar. 1, 2022

(54) APPROACHES FOR IMPROVING SKIN HYDRATION AND MOISTURIZATION

(71) Applicant: JRX BIOTECHNOLOGY, INC., Orange, CA (US)

(72) Inventors: Frederick L. Jordan, Newport Beach, CA (US); Chris Jordan, Newport Beach, CA (US)

(73) Assignee: JRX BIOTECHNOLOGY, INC., Orange, CA (US)

( * ) Notice: Subject to any disclaimer, the term of this patent is extended or adjusted under 35 U.S.C. 154(b) by 0 days.

(21) Appl. No.: 15/761,063

(22) PCT Filed: Sep. 14, 2016

(86) PCT No.: PCT/US2016/051683
§ 371 (c)(1),
(2) Date: Mar. 16, 2018

(87) PCT Pub. No.: WO2017/048807
PCT Pub. Date: Mar. 23, 2017

(65) Prior Publication Data
US 2018/0256482 A1 Sep. 13, 2018

Related U.S. Application Data

(60) Provisional application No. 62/220,059, filed on Sep. 17, 2015.

(51) Int. Cl.
*A61Q 19/00* (2006.01)
*A61K 8/86* (2006.01)
*A61K 8/92* (2006.01)
*A61B 5/00* (2006.01)
*A61B 5/0531* (2021.01)
*A61K 8/06* (2006.01)

(52) U.S. Cl.
CPC ............ *A61K 8/922* (2013.01); *A61B 5/0075* (2013.01); *A61B 5/0531* (2013.01); *A61B 5/441* (2013.01); *A61B 5/7257* (2013.01); *A61K 8/062* (2013.01); *A61K 8/068* (2013.01); *A61K 8/86* (2013.01); *A61Q 19/00* (2013.01); *A61Q 19/007* (2013.01); *A61K 2800/10* (2013.01); *A61K 2800/43* (2013.01); *A61K 2800/87* (2013.01); *A61K 2800/882* (2013.01)

(58) Field of Classification Search
CPC ..... A61B 5/0075; A61B 5/0531; A61B 5/441; A61B 5/7257; A61K 2800/10; A61K 2800/43; A61K 2800/87; A61K 2800/882; A61K 8/062; A61K 8/068; A61K 8/86; A61K 8/922; A61Q 19/00; A61Q 19/007
See application file for complete search history.

(56) References Cited

U.S. PATENT DOCUMENTS

| | | |
|---|---|---|
| 4,374,766 A | 2/1983 | Puchalski et al. |
| 4,973,473 A | 11/1990 | Schneider et al. |
| 5,126,331 A | 6/1992 | Gazzani |
| 5,128,324 A | 7/1992 | Walker et al. |
| 5,153,174 A | 10/1992 | Band et al. |
| 5,221,734 A | 6/1993 | Burk et al. |
| 5,318,960 A | 6/1994 | Toppo |
| 5,431,924 A | 7/1995 | Ghosh et al. |
| 5,472,713 A | 12/1995 | Fein et al. |
| 5,571,671 A | 11/1996 | Potter |
| 5,579,774 A | 12/1996 | Miller et al. |
| 5,614,212 A | 3/1997 | D'Angelo et al. |
| 5,665,378 A | 9/1997 | Davis et al. |
| 5,708,038 A | 1/1998 | Davis |
| 5,716,625 A | 2/1998 | Hahn et al. |
| 5,744,368 A | 4/1998 | Goldgaber et al. |
| 5,837,853 A | 11/1998 | Takashima et al. |
| 5,840,746 A | 11/1998 | Ducharme et al. |
| 5,849,334 A | 12/1998 | Rivlin |
| 5,861,268 A | 1/1999 | Tang et al. |
| 5,885,597 A | 3/1999 | Botknecht et al. |
| 5,891,651 A | 4/1999 | Roche et al. |
| 5,891,857 A | 4/1999 | Holt et al. |
| 5,936,107 A | 8/1999 | Raths et al. |
| 5,939,082 A | 8/1999 | Oblong et al. |
| 5,958,384 A | 9/1999 | Holick |
| 5,993,846 A | 11/1999 | Friedman et al. |
| 6,004,566 A | 12/1999 | Friedman et al. |
| 6,028,076 A | 2/2000 | Hirota et al. |
| 6,069,149 A | 5/2000 | Nanba et al. |

(Continued)

FOREIGN PATENT DOCUMENTS

| | | |
|---|---|---|
| CN | 1245394 A | 2/2000 |
| CN | 1874740 | 12/2006 |

(Continued)

OTHER PUBLICATIONS

Vanzan® Xanthan Gum Oct. 10, 2018; 16 pages (Year: 2018).*
Yoo et al. Bio-Medical CMOS ICs 2010 p. 75; 1 page (Year: 2010).*
U.S. Appl. No. 11/412,182, filed Aug. 24, 2006, Frederick L. Jordan.
International Search Report and Written Opinion dated Dec. 1, 2016, in International Application No. PCT/US2016/051683.
Aloe Laboratories, "Manufacturing Procedures, Product: Regular Traditional Hand Fillet Aloe Vera Juice," 1 page, date unknown.
Amadio et al., "Nonsteroidal anti-inflammatory drugs," Postgraduate Medicine, 93(4): 73-97 (1993).

(Continued)

*Primary Examiner* — Ernst V Arnold
(74) *Attorney, Agent, or Firm* — Knobbe, Martens, Olson & Bear, LLP

(57) ABSTRACT

The present disclosure generally relates to approaches for improving water absorption and retention by the skin's surface. In particular, the disclosure provides compositions and methods for preparing mixtures comprised of ethoxylated oils and water or mixtures comprised of micro or nano emulsions and water, which provide enhanced skin hydration or moisturization to a subject.

13 Claims, 4 Drawing Sheets

(56) References Cited

U.S. PATENT DOCUMENTS

| | | | |
|---|---|---|---|
| 6,103,246 A | 8/2000 | Tisdale et al. | |
| 6,194,388 B1 | 2/2001 | Kreig et al. | |
| 6,207,646 B1 | 3/2001 | Kreig et al. | |
| 6,239,116 B1 | 5/2001 | Kreig et al. | |
| 6,300,508 B1 | 10/2001 | Raths et al. | |
| 6,302,958 B1 | 10/2001 | Lindrud et al. | |
| 6,329,381 B1 | 12/2001 | Kurimoto et al. | |
| 6,339,068 B1 | 1/2002 | Kreig et al. | |
| 6,376,501 B1 | 4/2002 | Isobe et al. | |
| 6,387,938 B1 | 5/2002 | Mizuguchi et al. | |
| 6,406,705 B1 | 6/2002 | Davis et al. | |
| 6,416,722 B1 | 7/2002 | Izutsu et al. | |
| 6,426,334 B1 | 7/2002 | Agrawal et al. | |
| 6,444,234 B1 | 9/2002 | Kirby et al. | |
| 6,476,000 B1 | 11/2002 | Agrawal | |
| 6,518,265 B1 | 2/2003 | Kato et al. | |
| 6,656,499 B1 | 12/2003 | Foldvari et al. | |
| 6,759,056 B2 | 7/2004 | Jordan | |
| 6,787,152 B2 | 9/2004 | Kirby et al. | |
| 6,946,144 B1 | 9/2005 | Jordan | |
| 7,201,919 B2 | 4/2007 | Jordan | |
| 7,220,427 B2 | 5/2007 | Jordan | |
| 7,300,666 B2 | 11/2007 | Jordan | |
| 7,316,820 B2* | 1/2008 | Jordan | A61K 8/922 424/489 |
| 8,778,420 B1* | 7/2014 | Boyt | A61K 36/82 424/401 |
| 2002/0002272 A1 | 1/2002 | Houghton et al. | |
| 2003/0064093 A1 | 4/2003 | Jordan | |
| 2003/0104040 A1 | 6/2003 | Kirby et al. | |
| 2003/0199461 A1 | 10/2003 | Averett et al. | |
| 2004/0170676 A1 | 9/2004 | Jordan | |
| 2004/0202709 A1 | 10/2004 | Kirby et al. | |
| 2005/0019384 A1 | 1/2005 | Jordan | |
| 2006/0046962 A1 | 3/2006 | Meezan et al. | |
| 2006/0121103 A1 | 6/2006 | Kirby et al. | |
| 2006/0182771 A1 | 8/2006 | Dor et al. | |
| 2006/0188531 A1 | 8/2006 | Jordan | |
| 2006/0188532 A1 | 8/2006 | Jordan | |
| 2006/0193901 A1 | 8/2006 | Jordan | |
| 2007/0197418 A1 | 8/2007 | Rahse | |
| 2008/0064640 A1 | 3/2008 | Jordan | |
| 2008/0154210 A1 | 6/2008 | Jordan et al. | |
| 2009/0285876 A1 | 11/2009 | Hein et al. | |
| 2010/0009038 A1* | 1/2010 | Ella | A23L 2/56 426/66 |
| 2010/0086611 A1 | 4/2010 | Rabinow et al. | |
| 2011/0159104 A1 | 3/2011 | Teslenko | |
| 2011/0117187 A1 | 5/2011 | Stock et al. | |
| 2011/0166530 A1 | 7/2011 | Kreiner | |
| 2012/0064136 A1* | 3/2012 | Baker, Jr | A61K 8/4926 424/401 |
| 2014/0200531 A1 | 7/2014 | Jordan et al. | |
| 2015/0118176 A1 | 4/2015 | Mendoza et al. | |

FOREIGN PATENT DOCUMENTS

| | | |
|---|---|---|
| CN | 102389401 | 3/2012 |
| EP | 1 256 582 | 11/2002 |
| JP | 9-255926 | 9/1997 |
| WO | WO 92/08470 | 5/1992 |
| WO | WO 97/09992 A1 | 3/1997 |
| WO | WO 97/25023 A1 | 7/1997 |
| WO | WO 98/03163 | 1/1998 |
| WO | WO 98/29085 | 7/1998 |
| WO | WO 98/33474 | 8/1998 |
| WO | WO 98/34629 | 8/1998 |
| WO | WO 99/06024 | 2/1999 |
| WO | WO 99/44584 | 9/1999 |
| WO | WO 99/56727 | 11/1999 |
| WO | WO 00/02601 | 1/2000 |
| WO | WO 00/75304 | 12/2000 |
| WO | WO 01/46393 | 6/2001 |
| WO | WO 02/088595 | 1/2002 |
| WO | WO 2004/050856 A2 | 6/2004 |
| WO | WO 04/058808 | 7/2004 |
| WO | WO 04/060720 | 7/2004 |
| WO | WO 04/099389 | 11/2004 |
| WO | WO 04/110483 | 12/2004 |
| WO | WO 2005/039464 | 5/2005 |
| WO | WO 2006/041538 | 4/2006 |
| WO | WO 2009/019604 | 2/2009 |
| WO | WO 2014/106048 A2 | 7/2014 |

OTHER PUBLICATIONS

Barel and Clarys, "Study of the Stratum Corneum Barrier Function by Transepidermal Water Loss Measurements: Comparison between Two Commercial Instruments," Skin Pharmacol., 8:186-195.

Bergh, "Allergenic oxidation products in ethoxylated non-ionic surfactants: Chemical characterization and studies on allergenic activity and physicochemical behavior," Acta Dermato-Venereologica, 79(3) (Dec. 3, 1999), 28 pp.

Biomedical Information Services, Ltd., "Inspection Criteria," General Standard for Testing Purity of Aloe Vera, 7 pages (1996).

Bronaugh and Collier, "In Vitro Percutaneous Absorption Studies: Principle, Fundamentals, and Applications," eds., Bronaugh and Maibach, Bock Raton, Fl.,CRC Press pp. 237-241 (1991).

Brooks et al., May 1993, Pseudocollagenous proteins from yeast, Drug and Cosmetic Industry, 5 pp.

Charulatha et al., "Influence of different crosslinking treatments on the physical properties of collagen membranes," Biomaterials, 24(5): 759-767 (2003).

Chattem Inc., Packaging—"Flexall QuickGel," Copyright 1999.

Chinese Office Action issued on the related Chinese Patent Application No. 2004800320502, dated Feb. 20, 2008.

Cohen et al., "Wound Healing/Biochemical and Clinical Aspects," 1st ed. WB Saunders, Philadelphia (1992).

Collagen rejuvenates again skin, Life Extension™, Apr. 2004, 10 pp.

Collier et al., "Maintenance of Skin Viability During In vitro Percutaneous Absorption/Metabolism Studies," Toxicology and Applied Pharmacology, 99:522-533 (1989).

Cosmetic Ingredients & Ideas: Collagen and Glycosaminoglycans, Brooks Industries, Inc. (Fall 1992), 6 pp.

Cummings, et al., "A Natural Alternative: Jojoba esters are a New Category of Naturally Derived, Oil Free Emollients that Offer Good Properties for a Wide Variety of Cosmetic Products," SPC Asia (May 1999), 4 pages.

Cummings, et al., "In a Nutshell," 3 pages.

Croda, "Guide to Specialty Ingredients for the Personal Care Industry," pp. i-iii and 1-42 (2000).

Davis et al., "Aloe Vera as a biologically active vehicle for hydrocortisone acetate," JAPMA 81(1) (Jan. 1991), 9 pp.

David Julian McClements, "Edible nanoemulsions: fabrication, properties, and functional performance," Soft Matter, 7: 2297-2316 (2011).

Downing et al., Dermatology in General Medicine, Fitzpatrick, et al., eds., pp. 210-221(1993).

Extended Search Report dated Aug. 26, 2016 issued in European Patent Application No. 13869707.3, filed Jul. 3, 2015.

Esoteric Oils (Pty) Ltd., 2001, Macadamia oil for massage therapy and to help moisturize the skin, 3 pp. downloaded from http://www.essentialoils.co.za/macadamia_oil.htm.

Fitzpatrick et al., eds., Dermatology in General Medicine: Third Edition, McGraw-Hill Book Company (1987), pp. 185-190 and 210-223.

Flick, E.W. (1991), Cosmetics Additives—An Industrial Guide. William Andrew Publishing/Noyes. Online version available at: http://knovel.com/web/portal/browse/display?_EXT_KNOVEL_DISPLAY_bookid=581&VerticalID=0.

Floraesters® International Flora Technologies. Product Specification for Floraesters® 20: 1 page.

Floraesters® International Flora Technologies. Product Specification for Floraesters® 30: 1 page.

Floraesters® International Flora Technologies. Product Specification for Floraesters® 60: 1 page.

(56) References Cited

OTHER PUBLICATIONS

Floraesters® International Flora Technologies. Product Specification for Floraesters® 70: 1 page.
Floraesters® International Flora Technologies. Product Specification for Florasolvs® PEG-10 Sunflower: 1 page.
Floraesters® International Flora Technologies. Product Specification for Florasun® 90, Refined, Bleached, Winterized, Deodorized: 1 page.
Floraesters® International Flora Technologies. Product Specification for Floraesters® IPJ: 1 page.
Floraesters® International Flora Technologies. Product Specification for Floraesters® HIPJ: 1 page.
Floraesters® International Flora Technologies. Product Specification for Florabeads®, Jojoba 40/60: 1 page.
Floraesters® International Flora Technologies. Product Specification for Florabeads®, Jojoba White 60/100: 1 page.
Floraesters® International Flora Technologies. Product Specification for Florasolvs® PEG-80 Jojoba: 1 page.
Floraesters® International Flora Technologies. Product Specification for Florasolvs® PEG-120 Jojoba: 1 page.
Floraesters® International Flora Technologies. Product Specification for Floraesters® Jojoba Oil, Pasteurized, Not Refined: 1 page.
Floraesters® International Flora Technologies. Product Specification for Floraesters® 15: 1 page.
Floraesters® International Flora Technologies. Product Specification for Florabeads®, Jojoba 28/60, 1 of 2: 1 page.
Floraesters® International Flora Technologies. Product Specification for Florabeads®, Jojoba 28/60, 2 of 2: 1 page.
Foldvari et al., "Dermal and transdermal delivery of protein pharmaceuticals: lipid-based delivery systems for interferon a," Biotechnol. Appl. Biochem, 30:129-137 (1999).
Frankincense & Myrrh Essential Oil, Essential Notes, Madison Avenue Hair Color & Design, 1997, 3 pp., downloaded from http://www.madison-avenue.com/aroma/Oils/FrankMyrrh.htm.
Grindlay and Reynolds, "The Aloe Vera Phenomenon: A Review of the Properties and Modern Uses of the Leaf Parenchyma Gel," J. of Ethnopharmacology, 16:117-151 (1986).
Hart et al., "Two Functionally and Chemically Distinct Immunomodulatory Compounds in the Gel of Aloe Vera," J. of Ethnopharmacology, 23:61-71 (1988).
Hirata et al., "Biologically Active Constituents of Leaves and Roots of the Aloe Vera *Arborescens* var. *natalensis*," Z. Naturforsch, 32c:731-734 (1977).
Katayama et al., "A pentapeptide from type I procollagen promotes extracellular matrix production," J. Biol. Chem., 268(14):9941-9944 (1993).
International Aloe Science Council, Inc., "The Datasheet—100% Pure Aloe Vera," 1 page, date unknown.
International Search Report and Written Opinion from PCT/US2013/077985 dated Jun. 24, 2014.
International Preliminary Report on Patentability from PCT/US2013/077985 dated Jul. 9, 2015.
Office Action cited in the U.S. Appl. No. 11/412,182.
Office Action cited in the U.S. Appl. No. 11/597,700.
Office Action cited in the U.S. Appl. No. 11/931,288.
Office Action including Search Report and Written Opinion dated Nov. 1, 2016 in Singapore Patent Application No. 11201505076U.
Office Action from European Application No. 04753890.5 dated Jul. 28, 2014.
Office Action dated Oct. 26, 2016 issued in Eurasian Patent Application No. 201591015, filed Jun. 23, 2015.
Office Action dated May 17, 2017 issued in Chinese Patent Application No. 201380074085.1, filed Aug. 28, 2015.
Office Action dated Oct. 3, 2017 in Japanese Patent Application No. 2015-550799.
International Search Report issued on the related PCT Application No. PCT/US99/15409, dated Jan. 13, 2000.
International Search Report issued on the related PCT Application No. PCT/US2004/017169, dated Feb. 23, 2005.
International Search Report issued on the related PCT Application No. PCT/US2005/19017, dated Mar. 20, 2007.
Merck & Co., Inc., 1996, Calcitonin, in The Merck index, 12th edition, p. 1681.
Melaslow™, Brightening Cream with Melaslow™, SC-306, product formula: 2 pages.
Melaslow™, Skin Lightening Age Spot Treatment, product specification and claim substantiation: 2 pages.
"Nature's Plus® The Energy Supplements," 1999, Boswellin 300 mg and Boswellian Liquid Suspension product descriptions, 3 pp., downloaded from http://www.natplus.com/products/productNumber=7124.
Nelson et al., "Mid-Infrared Laser Ablation of Stratum Corneum Enhances in Vitro Percutaneous Transport of Drugs," The Society for Investigative Dermatology, Inc., pp. 874-879 (1991).
Odermatt et al., "Structural diversity and domain composition of a unique collagenous fragment (intima collagen) obtained from human placenta," Biochem J., 211(2):295-302 (May 1, 1983).
O'Malley et al., "Emu Products, Increasing Production and Profitability," Rural Industries Research & Development Corporation, pp. i-110 (Dec. 1999).
Pamphlet—Certificate of Analysis for Florasolvs® PEG-16 Macadamia, Jun. 2001.
Pamphlet—Life Extension™, Apr. 2002.
Pamphlet—The mighty macadamia, SPC ASIA, Mar. 2000.
Ponec, M., "Epidermal lipids in vivo," The Keratinocyte Handbook, Leigh et al., eds, pp. 351-363 (1994).
Preventics, 1999, Boswella product description, 2 pp., downloaded from http://preventics.com/products/boswella.html.
Qui et al., "Enhancement of primary and secondary cellular immune responses against human immunodeficiency virus type 1 gag by using dna expression vectors that target gag antigen to the secretory pathway," J. Virology, 74(13):5997-6005 (Jul. 2000).
Schaller et al., 1996, Interaction of liposomes with human skin: the role of the stratum corneum, Advanced Drug Delivery Reviews, 18:303-309 (1996).
Sederma, Etioline, product brochure, pp. 1-16 (Oct. 1996).
Sederma, Ichtyocollagene, product brochure, pp. 1-19 (Aug. 1993).
Sederma, Matrixyl "The physiological reconstruction of the matrix structures of the dermis to reduce deep and medium wrinkles: tested in vivo on a panel of 35 subjects during 2-4-6 months," product brochure, pp. 1-44 (Sep. 1999).
Sederma, Melaslow™ "Lightens the complexion/Decreases age spots," product brochure, overview and pp. 1-28 (Dec. 2000).
Taguchi et al., "Enhancement of Propylene Glycol Distribution in the Skin by High Purity cis-Unsaturated Fatty Acids with Different Alkyl Chain Lengths Having Different Double Bond Position," Biol. Pharm. Bull., 22(4):407-411 (1999).
Tasab et al., "Sequence-specific recognition of collagen triple helices by the collagen-specific molecular chaperone HSP47," JBC, 277(38):35007-35012 (Sep. 20, 2002).
Woodin, L., "Cutting Postop Pain," RN, pp. 26-33 (1993).
Yuan et al., "Investigation of microemulsion system for transdermal delivery of meloxicam," International Journal of Pharmaceuticals 321 (2006) 117-123.
Extended European Search Report dated Mar. 15, 2019, in European Patent Office Application No. 16847208.2.
Burnett et al., "Safety Assessment of PEGylated Alkyl Glycerides as Used in Cosmetics," International Journal of Toxicology, 2014:33 (Supplement 4), pp. 13S-39S, Aug. 27, 2014.
Cosmetic Ingredient Review Expert Panel, "Safety Assessment of PEGylated Alkyl Glycerides as Used in Cosmetics, Cosmetic Ingredient Review," Jan. 13, 2015 (https://www.cir-safety.org/supplementaldoc/safety-assessment-pegylated-alkyl-glycerides-used-cosmetics-1).
Floratech, "Formulation Guide—FloraSolvs—A quantitative comparison of common PEG ingredients' relative attributes," International Flora Technologies, Ltd., 2002.
"Floratech Product List," C.H. Erbslöh Baltic, Jan. 3, 2008, (http://www.cheb.lt/site/files/LS/FLORATECH_ProductList.pdf).
Yong et al., "The Chemical Composition and Biological Properties of Coconut (*Cocos nucifera* L.) Water," Molecules, 2009:14, pp. 5144-5164, Dec. 9, 2009.

(56) References Cited

OTHER PUBLICATIONS

Search Report dated Oct. 23, 2019 in Brazilian Patent Application No. BR112018005315-5, filed Sep. 14, 2016.
PEG ingredients' relative attributes, USA, doi:10.1016/j.yrtph.2015.01.013, (Jan. 1, 2007), pp. 1-12, URL: https://protecingredia.com/products/floratech/florasolvsbrochure.pdf_(Mar. 7, 2019), XP055565989 [X] 1-4,6-10 * pp. 3,9; figures 10,11; table 1 *.
Office Action dated May 6, 2020 in European Patent Application No. 16847208.2 Filed Apr. 9, 2018.
Office Action dated Apr. 30, 2021 in the corresponding Brazilian patent application BR 11 2018 005315 5 Filed Mar. 16, 2018.
Office Action dated May 31, 2021 in the corresponding Chinese Patent Application No. 201680053982.8 Filed Mar. 16, 2018.

* cited by examiner

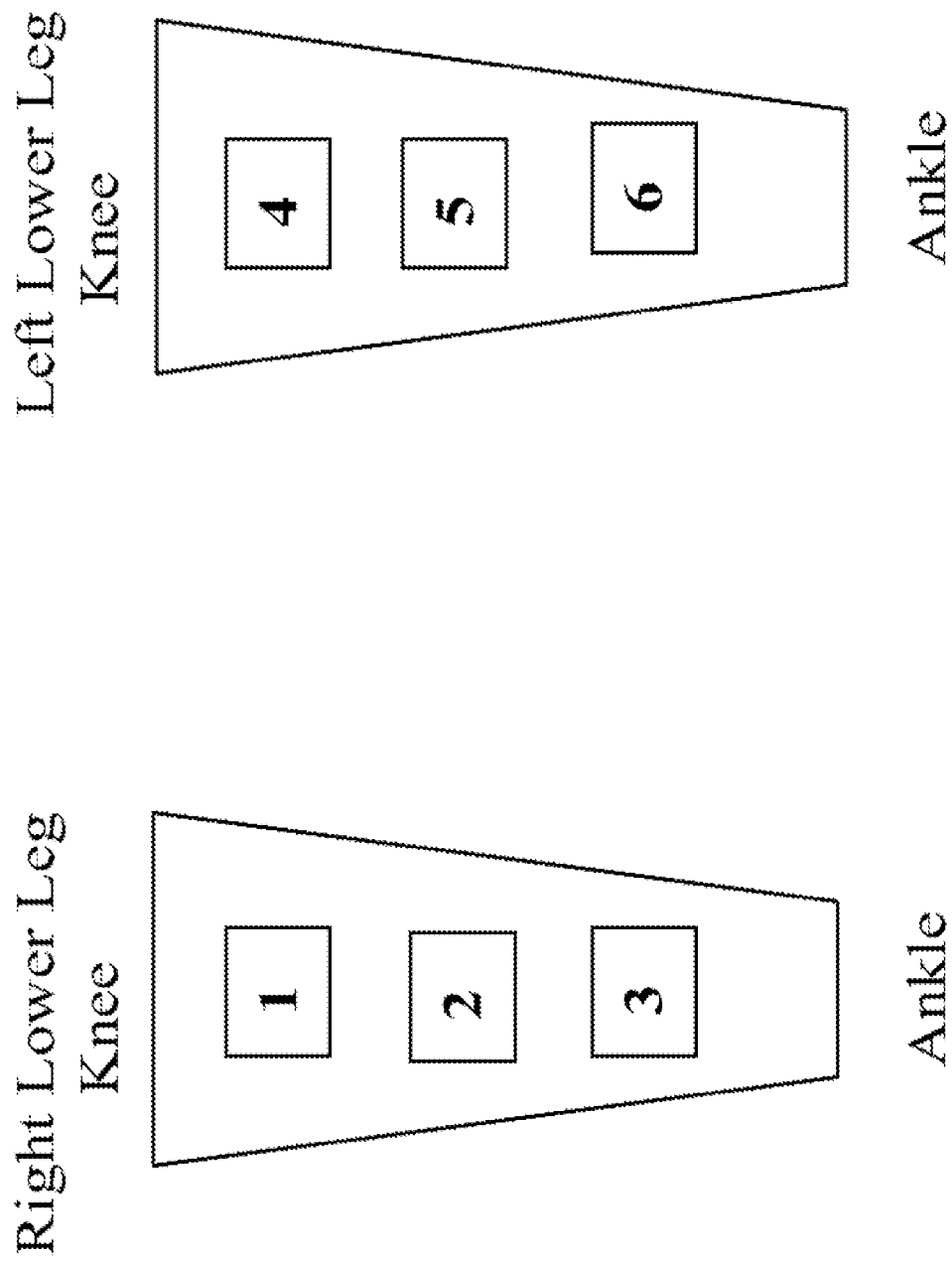
FIG. 2 (for Examples 1-4)

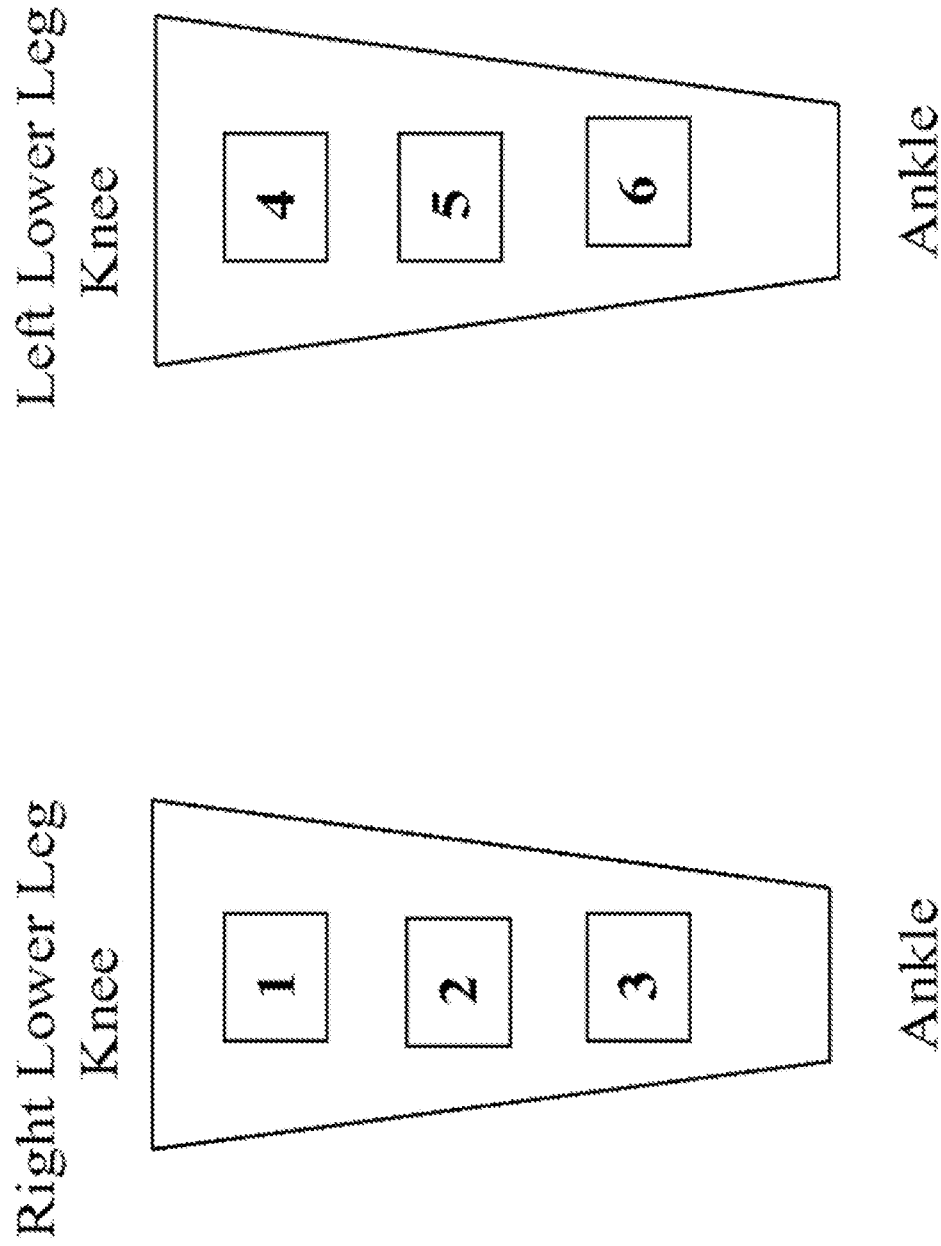
FIG. 3 (for Examples 6-10)

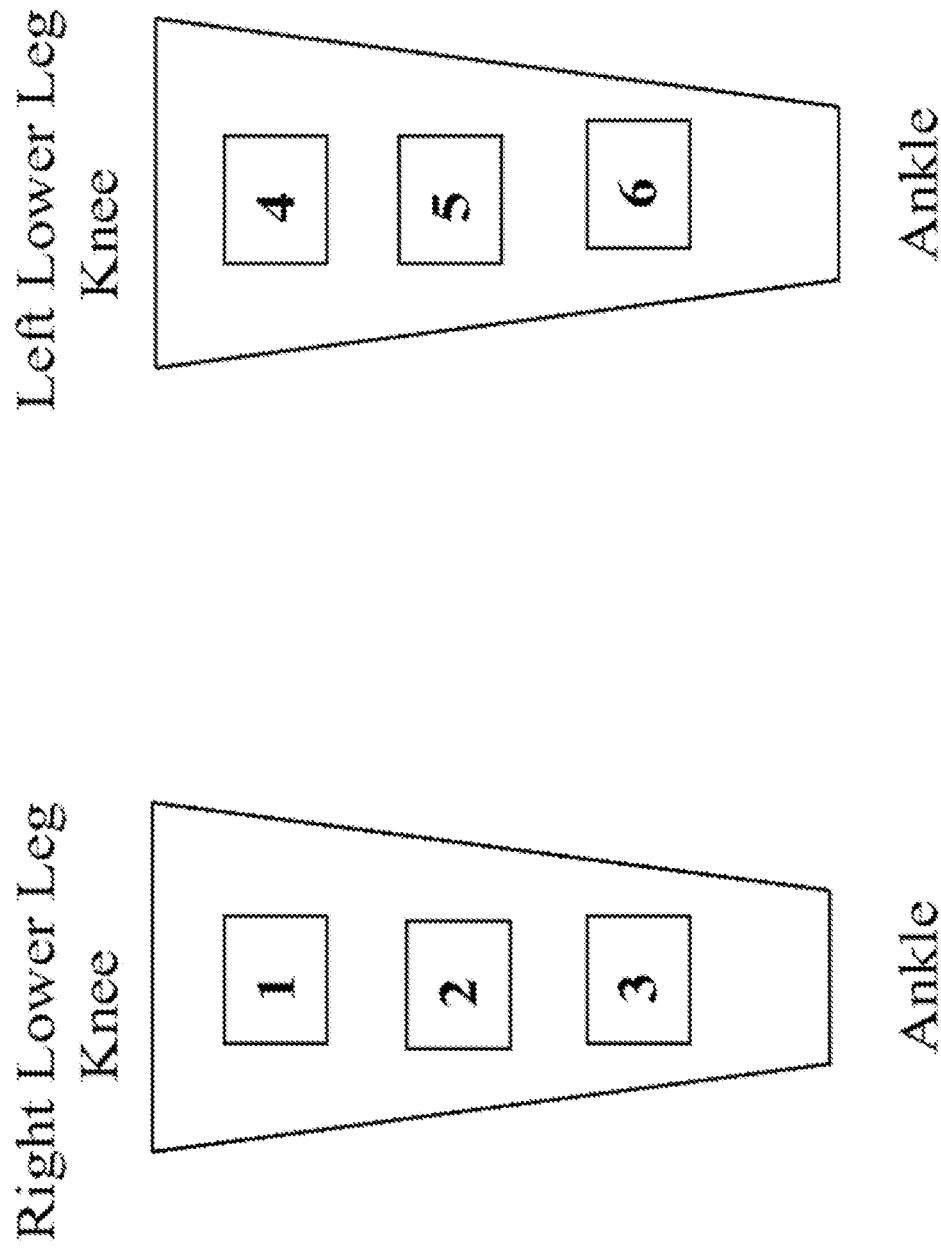
FIG. 4 (for Examples 11-14)

APPROACHES FOR IMPROVING SKIN HYDRATION AND MOISTURIZATION

CROSS REFERENCE TO RELATED APPLICATIONS

This application is a U.S. National Phase Application of PCT International Application Number PCT/US2016/051683, filed on Sep. 14, 2016, designating the United States of America and published in the English language, which is an International Application of and claims the benefit of priority to U.S. Provisional Application No. 62/220,059, filed on Sep. 17, 2015. The disclosures of the above-referenced applications are hereby expressly incorporated by reference in their entireties.

BACKGROUND

Field of the Invention

The present disclosure generally relates to approaches for improving water absorption and retention by the skin. In particular, the disclosure provides for compositions and methods for preparing mixtures which provide enhanced skin hydration and/or moisturization.

Description of the Related Art

Skin covers the entire human body and provides a protective barrier from various types of external stimuli and damage. The skin also protects against a loss of moisture, referred to as dehydration. Structurally, skin is a multi-layer membrane with a highly complex structure, and includes the epidermis, the outmost epithelial tissue of skin. The epidermis is mainly constructed of keratinocytes, and is composed of four layers—the stratum corneum, the stratum *granulosum*, the stratum *spinosum*, and the stratum basale. The outermost layer of the epidermis, stratum corneum, consists of dead cells (corneocytes). The primary function of the stratum corneum is to form a barrier to protect underlying tissue from infection, dehydration, chemicals, and mechanical stress.

Skin functions have been long recognized to be greatly dependent on the amount of moisture available in the stratum corneum. Changes in the amount of water content in the stratum corneum often have a significant impact on the functional properties of the skin. Thus, it is essential to provide sufficient moisture in the stratum corneum for healthy skin.

In recent years, several studies have been reported and focused on supplying the skin with water from an external source or on preventing the loss of water from the body in order to maintain the skin water content at a suitable level. As a result, various types of topical moisturizers having water-holding capacity have been developed and mainly used in the cosmetic, skincare, personal care and pharmaceutical fields. However, a significant number of people continue to suffer from dry skin symptoms. Furthermore, as people age, their skin loses elasticity, and decreases in the ability to retain moisture. Thus, many people experience dry skin as they age and require enhanced formulations and methods with the ability to help moisture penetrate the skin more easily, quickly and deeply, so that the moisture is achieved more rapidly and retained for a longer period of time.

Thus, there remains a need for compositions and methods for improving the level of hydration or moisturization of the skin to yield a rapid and enduring effect that can be accomplished conveniently and effectively.

SUMMARY

It has been discovered that certain ethoxylated oils, preferably a macadamia nut oil having an average number of ethoxylations per molecule that is 10, 11, 12, 13, 14, 15, 16, 17, 18, or 19 or an average number of ethoxylations per molecule that is within a range defined by any two of the aforementioned values, facilitates, improves, accelerates, and/or enhances hydration or moisturization of the skin, when said ethoxylated oils are mixed with water, and these mixtures are applied topically to a subject's skin. Without being bound to any particular theory or mechanism of action, it is contemplated that certain ethoxylated oils have the capacity to trap water in emulsions, and when the ethoxylated oils also contain fatty acids that mimic the fatty acids present on a subject's skin, for instance oleic acid, the ethoxylated oil and water solution facilitates, improves, accelerates, and/or enhances the hydration or moisture of the skin.

Disclosed herein are methods for enhancing hydration or moisturization of the skin of a subject including selecting or identifying a subject (e.g., a human or animal such as a domestic animal or farm animal such as dog, cat, horse, cattle, pig, or sheep), for enhanced skin hydration or moisturization, and topically administering to the skin of the selected or identified subject a mixture comprising or consisting of an ethoxylated oil, such as a macadamia nut oil, and water, wherein the average number of ethoxylations per molecule in the ethoxylated oil is 10, 11, 12, 13, 14, 15, 16, 17, 18, or 19 or an average number of ethoxylations per molecule that is within a range defined by any two of the aforementioned values; and, optionally, determining or measuring skin hydration or moisturization in the subject after administration of the mixture. In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages. In some alternatives, the mixture further includes an essential oil, a pigment, such as a mineral based color, and/or a fragrance.

In some alternatives, the ethoxylated oil, such as a macadamia nut oil, wherein the average number of ethoxylations per molecule is 10, 11, 12, 13, 14, 15, 16, 17, 18, or 19 or an average number of ethoxylations per molecule that is within a range defined by any two of the aforementioned values, is administered to the subject by adding the ethoxylated oil to a reservoir of water, such as that contained in a container, mixing vessel, mixing tank, mixing kettle, water softener system, water purification system, water filtration system, drinking water system, drinking fountain, swimming pool, pool, whirlpool, steam room, sauna, storage tank, sink, bath, tub or shower, or metering the ethoxylated oil in-line, in real time, to flowing water, mixing the ethoxylated oil with water to create a mixture, and contacting the subject with the mixture. In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages. In some alternatives, the mixture further includes an essential oil, a pigment, such as a mineral based color, and/or a fragrance. In some alternatives, skin hydration or skin moisture is measured or observed, for example, by determining an electromagnetic radiation, a dielectric constant, a dielectric permittivity, a thermal conductivity, or an elastographic parameter of the skin. In some alternatives, the determining or measuring skin hydration or moisturization comprises determining a water evaporation gradient or an electrical property of the skin, such as by capacitance, conductance, impedance, or alternating current conductivity on the skin surface, e.g., by transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometer. In some alternatives, the determining or measuring skin hydration or moisturization comprises analysis with an instrument, such as a Corneometer®, a Tewameter®, a Skicon® 200 hygrometer, a Nova DPM 9003, a Biox Epsilon, a Biox AquaFlux, a ServoMed® evaporimeter, a DermaLab®-Hydration Probe and Module, or a DermaLab®-TEWL Probe and Module.

In some alternatives, this mixture comprising or consisting of an ethoxylated oil, such as a macadamia nut oil, and water, wherein the average number of ethoxylations per molecule in the ethoxylated oil is 10, 11, 12, 13, 14, 15, 16, 17, 18, or 19 or an average number of ethoxylations per molecule that is within a range defined by any two of the aforementioned values, is formulated with or into a base, a functional ingredient, a functional ingredient blend, an active ingredient, an active ingredient blend, a bar soap, a liquid soap, a hand soap, a body soap, a body wash, a shower gel, a bubble bath, a dissolvable bead, such as a bath bead, a shaving cream, a shaving gel, an aftershave, a deodorant, an antiperspirant, an acne treatment formula, a lip care formula, a lip plumper, a face care formula, such as a facial moisturizer, a facial cleanser, a facial wash, a facial toner, a facial astringent, a facial clarifier, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, such as a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product (e.g., to treat eczema, psoriasis or rosacea), an anti-septic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation. In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages. In some alternatives, the mixture further includes an essential oil, a pigment, such as a mineral based color, and/or a fragrance.

Additional alternatives disclosed herein relate to methods for preparing a container, mixing vessel, mixing tank, mixing kettle, water softener system, water purification system, water filtration system, drinking water system, drinking fountain, swimming pool, pool, whirlpool, steam room, sauna, storage tank, sink, bath, tub or shower, which provides enhanced skin hydration or moisturization to a subject including: selecting a subject to receive enhanced skin hydration or moisturization; providing a container, mixing vessel, mixing tank, mixing kettle, water softener system, water purification system, water filtration system, drinking water system, drinking fountain, swimming pool, pool, whirlpool, steam room, sauna, storage tank, sink, bath, tub or shower comprising water; and adding to the water in the container, mixing vessel, mixing tank, mixing kettle, water softener system, water purification system, water filtration system, drinking water system, drinking fountain, swimming pool, pool, whirlpool, steam room, sauna, storage tank, sink, bath, tub or shower an ethoxylated oil, such as a macadamia nut oil, wherein the average number of ethoxylations per molecule in the ethoxylated oil is 10, 11, 12, 13, 14, 15, 16, 17, 18, or 19 or an average number of ethoxylations per molecule that is within a range defined by any two of the aforementioned values, or metering said ethoxylated oil in-line, in real time, to flowing water, so as to mix the ethoxylated oil with water to form a mixture. In some alternatives, the ethoxylated oil is macadamia nut oil with 16 ethoxylations per molecule. In some alternatives, the amount of ethoxylated oil added to water is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages. In some alternatives, the container further includes an essential oil, a pigment, such as a mineral based color, and/or a fragrance. In some alternatives, the methods further include observing, determining or measuring skin hydration or moisturization. In some alternatives, the determining or measuring skin hydration or moisturization includes determining an electromagnetic radiation, a dielectric constant, a dielectric permittivity, a thermal conductivity, or an elastographic parameter of the skin. In some alternatives, the determining or measuring skin hydration or moisturization includes determining a water evaporation gradient or an electrical property of the skin, such as by capacitance, conductance, impedance, or alternating current conductivity on the skin surface, e.g., by transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometer. In some alternatives, the determining or measuring skin hydration or moisturization comprises analysis with an instrument, such as a Corneometer®, a Tewameter®, a Skicon® 200 hygrometer, a Nova DPM 9003, a Biox Epsilon, a Biox AquaFlux, a ServoMed® evaporimeter, a DermaLab®-Hydration Probe and Module, or a DermaLab®-TEWL Probe and Module. In some alternatives, the mixture is formulated with or into a base, a functional ingredient, a functional ingredient blend, an active ingredient, an active ingredient blend, a bar soap, a liquid soap, a hand soap, a body soap, a body wash, a shower gel, a bubble bath, a dissolvable bead, such as a bath bead, a shaving cream, a shaving gel, an aftershave, a deodorant, an antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, such as a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product (e.g., to treat eczema, psoriasis or rosacea), an anti-septic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation.

Some alternatives disclosed herein relate to methods of making a micro or nano emulsion or mixture that includes a non-ethoxylated macadamia nut oil and water by: sonicating a first fluid jet stream including a non-ethoxylated macadamia nut oil and a second fluid jet stream including water, wherein the sonicating is performed by positioning a tip of a sonication probe within a gap defined between a first fluid jet which emits the first fluid jet stream, and a second fluid jet which emits the second fluid jet stream, positioned such that the fluid jet streams from the first fluid jet and the second fluid jet impinge in the gap creating a point of high turbulence at the point of impact of the fluid jet streams, with each of the fluid jet streams having sufficient linear velocity to achieve high intensity micromixing of the macadamia nut oil and water, and the sonication probe providing ultrasonic energy in the immediate vicinity of the impinging fluid jet streams thereby generating the micro or nano emulsion or mixture that comprises the macadamia nut oil and water. In some alternatives of this and other aspects of the disclosure, the macadamia nut oil is ethoxylated. In some alternatives, the ethoxylated macadamia nut oil has an average number of ethoxylations per molecule of 10, 11, 12, 13, 14, 15, 16, 17, 18, or 19 or an average number of ethoxylations per molecule that is within a range defined by any two of the aforementioned values. In some alternatives, the ethoxylated oil is macadamia nut oil with 16 ethoxylations per molecule. In some alternatives, the amount of macadamia nut oil or ethoxylated macadamia nut oil in the micro or nano emulsion is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts. In some alternatives, the sonicating is conducted above the freezing point of water but less than or equal to ambient temperature such as, for example, 1, 2, 3, 4, 5, 6, 7, 8, 9, 10, 11, 12, 13, 14, 15, 16, 17, 18, 19, 20, 21, 22, 23, 24, or 25 degrees Celsius or a temperature within a range defined by any two of the aforementioned temperatures. In some alternatives, the temperature of the first fluid jet stream and/or the second fluid jet stream is above the freezing point of water but less than or equal to ambient temperature such as, for example, 1, 2, 3, 4, 5, 6, 7, 8, 9, 10, 11, 12, 13, 14, 15, 16, 17, 18, 19, 20, 21, 22, 23, 24, or 25 degrees Celsius or a temperature within a range defined by any two of the aforementioned temperatures. In some alternatives, the micro or nano emulsion or mixture further includes an essential oil, a pigment, such as a mineral based color, and/or a fragrance.

In some alternatives, the methods for making the micro or nano emulsions or mixtures disclosed herein further include adding the micro or nano emulsion or mixture to a reservoir of water, such that is contained in a container, a mixing vessel, a mixing tank, a mixing kettle, a water softener system, a water purification system, a water filtration system, a drinking water system, a drinking fountain, a swimming pool, a pool, a whirlpool, a steam room, a sauna, a storage tank, a sink, a bath, a tub or a shower, or metering the micro or nano emulsion or mixture in-line, in real time, to flowing water and thereby allowing the micro or nano emulsion or mixture to mix with water, and contacting a subject with the mixture which consists of the micro or nano emulsion and water. In some alternatives, the methods disclosed herein further include observing, determining or measuring skin hydration or moisturization. In some alternatives, the determining or measuring skin hydration or moisturization includes determining an electromagnetic radiation, a dielectric constant, a dielectric permittivity, a thermal conductivity, or an elastographic parameter of the skin. In some alternatives, the determining or measuring skin hydration or moisturization comprises determining a water evaporation gradient or an electrical property of the skin, such as by capacitance, conductance, impedance, or alternating current conductivity on the skin surface, e.g., by transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometer. In some alternatives, the determining or measuring skin hydration or moisturization comprises analysis with an instrument, such as a Corneometer®, a Tewameter®, a Skicon® 200 hygrometer, a Nova DPM 9003, a Biox Epsilon, a Biox AquaFlux, a ServoMed® evaporimeter, a DermaLab®-Hydration Probe and Module, or a DermaLab®-TEWL Probe and Module. In some alternatives, the methods disclosed herein further include introducing the mixture which consists of the micro or nano emulsion and water into a base, a functional ingredient, a functional ingredient blend, an active ingredient, an active ingredient blend, a bar soap, a liquid soap, a hand soap, a body soap, a body wash, a shower gel, a bubble bath, a dissolvable bead, such as a bath bead, a shaving cream, a shaving gel, an aftershave, a deodorant, an antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, such as a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product (e.g., to treat eczema, psoriasis or rosacea), an anti-septic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation.

Some alternatives disclosed herein also relate to methods of making an ethoxylated oil that comprises a macadamia nut oil and water including: transesterification of a non-ethoxylated macadamia nut oil in the presence of water to create an ethoxylated macadamia nut oil; and adding the resulting ethoxylated macadamia nut oil to a reservoir of water to create a mixture. In some alternatives, the ethoxylated macadamia nut oil has an average number of ethoxylations per molecule that is 10, 11, 12, 13, 14, 15, 16, 17, 18, or 19 or an average number of ethoxylations per molecule that is within a range defined by any two of the aforementioned values. In some alternatives, the ethoxylated oil is macadamia nut oil with 16 ethoxylations per molecule. In some alternatives, the amount of ethoxylated macadamia nut oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts. In some alternatives, the methods disclosed herein further include adding an essential oil, a pigment, such as a mineral based color, and/or a fragrance to the mixture. In some alternatives, the methods disclosed herein further include adding the ethoxylated oil to a reservoir of water, such as that contained in a container, a mixing vessel, a mixing tank, a mixing kettle, a water softener system, a water purification system, a water filtration system, a drinking water system, a drinking fountain, a swimming pool, a pool, a whirlpool, a steam room, a sauna, a storage tank, a sink, a bath, a tub or a shower, or metering the ethoxylated oil in-line, in real time, to flowing water, and thereby allowing the ethoxylated oil to mix with water to create a mixture, and contacting a subject with the mixture. In some alternatives, the methods disclosed herein further include observing, determining or measuring skin hydration or moisturization. In some alternatives, the determining or measuring skin hydration or moisturization comprises determining an electromagnetic radiation, a dielectric constant, a dielectric permittivity, a thermal conductivity, or an elastographic parameter of the skin. In some alternatives, the determining or measuring skin hydration or moisturization includes determining a water evaporation gradient or an electrical property of the skin, such as by capacitance, conductance, impedance, or alternating current conductivity on the skin surface, e.g., by transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometer. In some alternatives, the determining or measuring skin hydration or moisturization comprises analysis with an instrument, such as Corneometer®, a Tewameter®, a Skicon® 200 hygrometer, a Nova DPM 9003, a Biox Epsilon, a Biox AquaFlux, a ServoMed® evaporimeter, a DermaLab®-Hydration Probe and Module, or a DermaLab®-TEWL Probe and Module. In some alternatives, the methods disclosed herein further include introducing the mixture into a base, a functional ingredient, a functional ingredient blend, an active ingredient, an active ingredient blend, a bar soap, a liquid soap, a hand soap, a body soap, a body wash, a shower gel, a bubble bath, a dissolvable bead, such as a bath bead, a shaving cream, a shaving gel, an aftershave, a deodorant, an antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, such as a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product (e.g., to treat eczema, psoriasis or rosacea), an anti-septic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation.

In yet a further aspect, some alternatives disclosed herein relate to methods of making a micro or nano emulsion or mixture that includes a non-ethoxylated macadamia nut oil and water including: providing a first fluid jet stream including a non-ethoxylated macadamia nut oil and a second fluid jet stream including water, wherein the fluid jet streams are provided by a first fluid jet which emits the first fluid jet stream, and a second fluid jet which emits the second fluid jet stream, positioned such that the fluid jet streams from the first fluid jet and the second fluid jet impinge and create a point of high turbulence at the point of impact of the fluid jet streams, with each of the fluid jet streams having sufficient linear velocity, such as, for example, 100, 200, 300, 400, 500, 600, 700, 800, or 900 meters per second (m/s) or a linear velocity within a range defined by any two of the aforementioned liner velocities, so as to achieve a high intensity micromixing of the macadamia nut oil and water, wherein the first and second fluid jet streams are contacted under a pressure of 25,000-50,000 pounds per square inch (psi) or within a range defined by any two numbers within the range of 25,000-50,000 psi and, wherein after the first and second fluid jet streams are contacted under pressure, the resultant micro or nano emulsion or mixture that includes the macadamia nut oil and water is brought to atmospheric pressure. In some of these alternatives, the macadamia nut oil is ethoxylated. In some alternatives, the ethoxylated macadamia nut oil has an average number of ethoxylations per molecule that is 10, 11, 12, 13, 14, 15, 16, 17, 18, or 19 or an average number of ethoxylations per molecule that is within a range defined by any two of the aforementioned values. In some alternatives, the ethoxylated oil is macadamia nut oil with 16 ethoxylations per molecule. In some alternatives, the amount of macadamia nut oil or ethoxylated macadamia nut oil in the micro or nano emulsion is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts. In some alternatives, the contact of the first and second fluid jet streams is conducted above the freezing point of water but less than or equal to ambient temperature such as, for example, 1, 2, 3, 4, 5, 6, 7, 8, 9, 10, 11, 12, 13, 14, 15, 16, 17, 18, 19, 20, 21, 22, 23, 24, or 25 degrees Celsius or a temperature within a range defined by any two of the aforementioned temperatures. In some alternatives, the temperature of the first fluid jet stream and/or the second fluid jet stream is above the freezing point of water but less than or equal to ambient temperature such as, for example, 1, 2, 3, 4, 5, 6, 7, 8, 9, 10, 11, 12, 13, 14, 15, 16, 17, 18, 19, 20, 21, 22, 23, 24, or 25 degrees Celsius or a temperature within a range defined by any two of the aforementioned temperatures. In some alternatives, the methods disclosed herein further include adding an essential oil, a pigment, such as a mineral based color, and/or a fragrance to the micro or nano emulsion. In some alternatives, the methods disclosed herein further include adding the micro or nano emulsion to a reservoir of water, such as that contained in a container, a mixing vessel, a mixing tank, a mixing kettle, a water softener system, a water purification system, a water filtration system, a drinking water system, a drinking fountain, a swimming pool, a pool, a whirlpool, a steam room, a sauna, a storage tank, a sink, a bath, a tub or a shower, or metering the micro or nano emulsion in-line, in real time, to flowing water, thereby allowing the micro or nano emulsion to mix with water to create a mixture, and contacting a subject with the mixture. In some alternatives, the methods disclosed herein further include observing, determining or measuring skin hydration or moisturization. In some alternatives, the determining or measuring skin hydration or moisturization includes determining an electromagnetic radiation, a dielectric constant, a dielectric permittivity, a thermal conductivity, or an elastographic parameter of the skin. In some alternatives, the determining or measuring skin hydration or moisturization includes determining a water evaporation gradient or an electrical property of the skin, such as by capacitance, conductance, impedance, or alternating current conductivity on the skin surface, e.g., by transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometer. In some alternatives, the determining or measuring skin hydration or moisturization comprises analysis with an instrument, such as a Corneometer®, a Tewameter®, a Skicon® 200 hygrometer, a Nova DPM 9003, a Biox Epsilon, a Biox AquaFlux, a ServoMed® evaporimeter, a DermaLab®-Hydration Probe and Module, or a DermaLab®-TEWL Probe and Module. In some alternatives, the methods disclosed herein further include introducing the mixture which consists of the micro or nano emulsion and water into a base, a functional ingredient, a functional ingredient blend, an active ingredient, an active ingredient blend, a bar soap, a liquid soap, a hand soap, a body soap, a body wash, a shower gel, a bubble bath, a dissolvable bead, such as a bath bead, a shaving cream, a shaving gel, an aftershave, a deodorant, an antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, such as a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product (e.g., to treat eczema, psoriasis or rosacea), an anti-septic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation.

Additionally, disclosed herein are compositions and methods for enhancing hydration or moisturization of the skin of a subject (e.g., a human or animal such as a domestic animal or farm animal such as dog, cat, horse, cattle, pig, or sheep), including selecting or identifying a subject for improving skin hydration or moisturization, and topically administering to the skin of the selected or identified subject a mixture comprising or consisting of an ethoxylated oil, such as ethoxylated macadamia nut oil, and water, wherein the average number of ethoxylations per molecule in the ethoxylated oil is 10, 11, 12, 13, 14, 15, 16, 17, 18, or 19 or the average number of ethoxylations per molecule can be within a range defined by any of the two aforementioned values. In the mixture, water is contacted with said ethoxylated oil prior to optionally combining the mixture with one or more components or additional compounds, and, optionally, determining or measuring skin hydration or moisturization in the subject after administration of the mixture. Once the mixture is topically administered to the skin of the selected or identified subject, hydration or moisturization of the subject's skin can also be determined or measured. In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages.

In some alternatives, the one or more components or additional compounds are selected from a group consisting of 0-5% w/w xanthan gum, 0-5% w/w zinc dioxide, 0-5% w/w titanium dioxide, 0-5% w/w talc, 0-5% w/w silica, and 0-3% w/w combined phenoxyethanol, caprylyl glycol, ethylhexylglycerin, and hexylene glycol, known under the trade name Botanistat PF-64. In some alternatives, the one or more components or additional compounds are selected, in any combination, from the group consisting of glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides. In some alternatives, the mixture further includes an essential oil, a pigment, such as a mineral based color, and/or a fragrance.

In some alternatives, the ethoxylated oil or micro or nano emulsion is administered to the subject by first adding the ethoxylated oil or micro or nano emulsion to a reservoir of water, such as that contained in a container, mixing vessel, mixing tank, mixing kettle, water softener system, water purification system, water filtration system, drinking water system, drinking fountain, swimming pool, pool, whirlpool, steam room, sauna, storage tank, sink, bath, tub or shower, or metering the ethoxylated oil or micro or nano emulsion, in real time, to flowing water to create the mixture, then optionally adding at least one component before contacting the mixture with the subject.

In some alternatives, the water contacted with ethoxylated oil or micro or nano emulsion is selected from the group consisting of drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and/or any mixtures thereof. In some alternatives, the bottled water, sparkling water, sparkling mineral water, alkaline water, glacial water, coconut water, carbonated water, purified drinking water, natural water, spring water, natural spring water, artesian water, natural artesian water, mineral water or natural mineral water is further selected from the group consisting of Fiji® Water, Ice Mountain, Sparkletts, Zico, Vita Coco, Aquafina, Arrowhead Water, Dejà Blue, Crystal Geyser, Evian, Glacéau Smartwater, Glacéau Vitaminwater, Iceland Pure Spring Water, Nestlé® Pure Life®, Nestlé® Waters, Niagara, Poland Spring, Propel Fitness Water, San Pellegrino, Gerolsteiner, Ferrarelle, Perrier, Mountain Valley, Ty Nant, Volvic, Icelandic Glacial, Dasani, Deer Park, Ozarka, Voss, Vittel, Contrex, Acqua Panna, São Lourenço and Sierra Springs water and/or any mixtures thereof.

In some alternatives, skin hydration or skin moisture is measured or observed, for example, by determining an electromagnetic radiation, a dielectric constant, a dielectric permittivity, a thermal conductivity, or an elastographic parameter of the skin. In some alternatives, the determination of skin hydration or moisturization comprises determining a water evaporation gradient or an electrical property of the skin, such as by capacitance, conductance, impedance, or alternating current conductivity on the skin surface, e.g., by transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometer. In some alternatives, the determining or measuring skin hydration or moisturization comprises analysis with an instrument, such as a Corneometer®, a Tewameter®, a Skicon® 200 hygrometer, a Nova Dermal Phase Meter 9003, a Biox Epsilon, a Biox AquaFlux, a ServoMed® evaporimeter, a DermaLab®-Hydration Probe and Module, or a DermaLab®-TEWL Probe and Module.

In some alternatives, the mixture comprising, consisting essentially of, or consisting of water contacted with an ethoxylated oil, such as a macadamia nut oil, wherein the average number of ethoxylations per molecule in the ethoxylated oil is 10, 11, 12, 13, 14, 15, 16, 17, 18, or 19 or an average number of ethoxylations per molecule that is within a range defined by any two of the aforementioned values, is provided as is or neat, and in some alternatives this mixture is formulated with or into a base, a functional ingredient, a functional ingredient blend, an active ingredient, an active ingredient blend, a bar soap, a liquid soap, a hand soap, a body soap, a body wash, a shower gel, a bubble bath, a dissolvable bead, such as a bath bead, a shaving cream, a shaving gel, an aftershave, a deodorant, an antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, such as a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product (e.g., to treat eczema, psoriasis or rosacea), an anti-septic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation. In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages. In some alternatives, additional components in the mixture include 0-5% w/w xanthan gum, 0-5% w/w zinc dioxide, 0-5% w/w titanium dioxide, 0-5% w/w talc, 0-5% w/w silica, and 0-3% w/w combined phenoxyethanol, caprylyl glycol, ethylhexylglycerin, and hexylene glycol, sold under the trade name Botanistat PF-64. In some alternatives, additional components include glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides. In some alternatives, the mixture further includes an essential oil, a pigment, such as a mineral based color, and/or a fragrance.

Some alternatives disclosed herein relate to methods for increasing conductance and capacitance of a subject's skin, (e.g., a human or animal such as a domestic animal or farm animal such as dog, cat, horse, cattle, pig, or sheep) and decreasing impedance of said subject's skin, including selecting or identifying a subject for improving skin hydration or moisturization, and topically administering to the skin of the selected or identified subject a mixture comprising or consisting of an ethoxylated oil, such as ethoxylated macadamia nut oil, and water, wherein the average number of ethoxylations per molecule in the ethoxylated oil is 10, 11, 12, 13, 14, 15, 16, 17, 18, or 19 or an average number of ethoxylations per molecule that can be within a range defined by any of the two aforementioned values. In the mixture, water is contacted with said ethoxylated oil prior to combining the mixture with one or more components, which can be done optionally, and determining or measuring skin hydration or moisturization in the subject after administration of the mixture. In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages.

In some alternatives, the one or more components or additional compounds added are selected from a group consisting of 0-5% w/w xanthan gum, 0-5% w/w zinc dioxide, 0-5% w/w titanium dioxide, 0-5% w/w talc, 0-5% w/w silica, and 0-3% w/w combined phenoxyethanol, caprylyl glycol, ethylhexylglycerin, and hexylene glycol, sold under the trade name Botanistat PF-64. In some alternatives, the one or more components or additional compounds added are selected, in any combination, from the group consisting of glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides. In some alternatives, the mixture further includes an essential oil, a pigment, such as a mineral based color, and/or a fragrance.

In some alternatives, the mixture, which consists, consists essentially of, or comprises water first contacted with the ethoxylated oil is administered to the subject (e.g., a human or animal such as a domestic animal or farm animal such as dog, cat, horse, cattle, pig, or sheep) by adding the ethoxylated oil to a reservoir of water, such as that contained in a container, mixing vessel, mixing tank, mixing kettle, water softener system, water purification system, water filtration system, drinking water system, drinking fountain, swimming pool, pool, whirlpool, steam room, sauna, storage tank, sink, bath, tub or shower, or metering the ethoxylated oil in-line, in real time, to flowing water to create the mixture, then optionally adding the one or more components, before contacting the mixture with the subject.

In some alternatives, the water contacted with ethoxylated oil is selected from the group consisting of drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and/or any mixtures thereof. In some alternatives, the drinking water, bottled water, sparkling water, sparkling mineral water, alkaline water, glacial water, coconut water, carbonated water, purified drinking water, natural water, spring water, natural spring water, artesian water, natural artesian water, mineral water or natural mineral water is further selected from the group consisting of Fiji® Water, Ice Mountain, Sparkletts, Zico, Vita Coco, Aquafina, Arrowhead Water, Déjà Blue, Crystal Geyser, Evian, Glacéau Smartwater, Glacéau Vitaminwater, Iceland Pure Spring Water, Nestlé® Pure Life®, Nestlé® Waters, Niagara, Poland Spring, Propel Fitness Water, San Pellegrino, Gerolsteiner, Ferrarelle, Perrier, Mountain Valley, Ty Nant, Volvic, Icelandic Glacial, Dasani, Deer Park, Ozarka, Voss, Vittel, Contrex, Acqua Panna, São Lourenço and Sierra Springs water and/or any mixtures thereof.

In some alternatives, skin hydration or skin moisture is measured or observed, for example, by determining an electromagnetic radiation, a dielectric constant, a dielectric permittivity, a thermal conductivity, or an elastographic parameter of the skin. In some alternatives, the determining skin hydration or moisturization comprises determining a water evaporation gradient or an electrical property of the skin, such as by capacitance, conductance, impedance, or alternating current conductivity on the skin surface, e.g., by transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometer. In some alternatives, the determining or measuring skin hydration or moisturization comprises analysis with an instrument, such as a Corneometer®, a Tewameter®, a Skicon® 200 hygrometer, a Nova Dermal Phase Meter 9003, a Biox Epsilon, a Biox AquaFlux, a ServoMed® evaporimeter, a DermaLab®-Hydration Probe and Module, or a DermaLab®-TEWL Probe and Module.

In some alternatives, the mixture comprising or consisting of water and an ethoxylated oil is created by first contacting water with an ethoxylated oil such as a macadamia nut oil, wherein the average number of ethoxylations per molecule in the ethoxylated oil is 10, 11, 12, 13, 14, 15, 16, 17, 18, or 19 or an average number of ethoxylations per molecule that is within a range defined by any two of the aforementioned values, is formulated neat or as is, and in some alternatives this mixture is formulated with or into a base, a functional ingredient, a functional ingredient blend, an active ingredient, an active ingredient blend, a bar soap, a liquid soap, a hand soap, a body soap, a body wash, a shower gel, a bubble bath, a dissolvable bead, such as a bath bead, a shaving cream, a shaving gel, an aftershave, a deodorant, an antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, such as a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product (e.g., to treat eczema, psoriasis or rosacea), an anti-septic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation. In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages. In some alternatives, additional components that can be added to the mixture include 0-5% w/w xanthan gum, 0-5% w/w zinc dioxide, 0-5% w/w titanium dioxide, 0-5% w/w talc, 0-5% w/w silica, and 0-3% w/w combined phenoxyethanol, caprylyl glycol, ethylhexylglycerin, and hexylene glycol, sold under the trade name Botanistat PF-64. In some alternatives, additional components include glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides. In some alternatives, the mixture further includes an essential oil, a pigment, such as a mineral based color, and/or a fragrance.

Some alternatives disclosed herein relate to methods of making a mixture for improving hydration or moisturization of a subject (e.g., a human or animal such as a domestic animal or farm animal such as dog, cat, horse, cattle, pig, or sheep) including mixing water and an ethoxylated oil, such as ethoxylated macadamia nut oil, to create a mixture or emulsion, prior to the addition or mixing-in of an additional compound or component. That is, optionally, after mixing water and the ethoxylated oil, at least one additional compound or component such as e.g., glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides may be added to said mixture. In some alternatives, one or more compounds or components that can be added to the mixture are selected from the group consisting of xanthan gum, zinc dioxide, titanium dioxide, talc, silica, and a combined mixture of phenoxyethanol caprylyl glycol, ethylhexylglycerin, and hexylene glycol, known under the trade name Botanistat PF-64.

In some alternatives, the ethoxylated oil is macadamia nut oil with 16 ethoxylations per molecule. In some alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or a percentage that is within a range defined by any two of the aforementioned percentages. In some alternatives, the mixture further includes an essential oil, a pigment, such as a mineral based color, and/or a fragrance.

In some alternatives, the water contacted with ethoxylated oil is selected from the group consisting of drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and/or any mixtures thereof. In some alternatives, the drinking water, bottled water, sparkling water, sparkling mineral water, alkaline water, glacial water, coconut water, carbonated water, purified drinking water, natural water, spring water, natural spring water, artesian water, natural artesian water, mineral water or natural mineral water is further selected from the group consisting of Fiji® Water, Ice Mountain, Sparkletts, Zico, Vita Coco, Aquafina, Arrowhead Water, Dejà Blue, Crystal Geyser, Evian, Glacéau Smartwater, Glacéau Vitaminwater, Iceland Pure Spring Water, Nestlé® Pure Life®, Nestlé® Waters, Niagara, Poland Spring, Propel Fitness Water, San Pellegrino, Gerolsteiner, Ferrarelle, Perrier, Mountain Valley, Ty Nant, Volvic, Icelandic Glacial, Dasani, Deer Park, Ozarka, Voss, Vittel, Contrex, Acqua Panna, São Lourenço and Sierra Springs water and/or any mixtures thereof. The foregoing summary is illustrative only and is not intended to be in any way limiting. In addition to the illustrative aspects, alternatives, and features described herein, further aspects, alternatives, objects and features of the disclosure will become fully apparent from the drawings and the following detailed description and the claims.

BRIEF DESCRIPTION OF THE DRAWINGS

FIG. 2 is a schematic drawing of selected skin test sites demarcated on two legs of a single subject. Such skin test sites were selected by an independent clinical testing facility to carry out an initial hydration or moisturization study. In this initial study, a total of six (6) test sites were selected based on a computer generated test site randomization code. This randomization code was based on the location of 6 possible test sites, more specifically 3 test sites per lower leg. Each test site was approximately 4 cm×4 cm. Test sites were placed centrally on the outer lower legs (at least 2 cm from the knee and at least 2 cm from the ankle). Per randomization code, one site served as the placebo control (deionized or DI water only) site and one site served as the positive control site. The remaining four sites served to test four different experimental formulas, respectively. FIG. 2 corresponds to Examples 1 through 4 herein below.

FIG. 3 is a schematic drawing of selected skin test sites demarcated on two legs of a single subject. Such skin test sites were selected by an independent clinical testing facility to carry out a second hydration or moisturization study. In this second study, a total of six (6) test sites were selected based on a computer generated test site randomization code. This randomization code was based on the location of 6 possible test sites, more specifically 3 test sites per lower leg. Each test site was approximately 4 cm×4 cm. Test sites were placed centrally on the outer lower legs (at least 2 cm from the knee and at least 2 cm from the ankle). Per randomization code, one site served as the placebo control (deionized or DI water only) site, one served as the positive control (DI water and 2% PEG-16 Macadamia Glycerides) site, and a third served as a second placebo control (DI water and a number of specified components, without any PEG-16 Macadamia Glycerides) site. The remaining three sites served to test three different experimental formulas, respectively. FIG. 3 corresponds to Examples 6 through 10 herein below.

FIG. 4 is a schematic drawing of selected skin test sites demarcated on two legs of a single subject. Such skin test sites were selected by an independent clinical testing facility to carry out a third hydration or moisturization study. For this third study, a total of six (6) test sites were selected based on a computer generated test site randomization code. This randomization code was based on the location of 6 possible test sites, more specifically 3 test sites per lower leg. Each test site was approximately 4 cm×4 cm. Test sites were placed centrally on the outer lower legs (at least 2 cm from the knee and at least 2 cm from the ankle). Per randomization code, one site served as the placebo control (deionized or DI water only) site, one served as the second placebo control (Nestlé® "Pure Life"® Purified bottled Water only) site, and a third served as the last placebo control (Fiji® Natural Artesian bottled Water only) site. The remaining three sites served to test three different experimental formulas, respectively. FIG. 4 corresponds to Examples 11 through 14 herein below.

Figure 1:
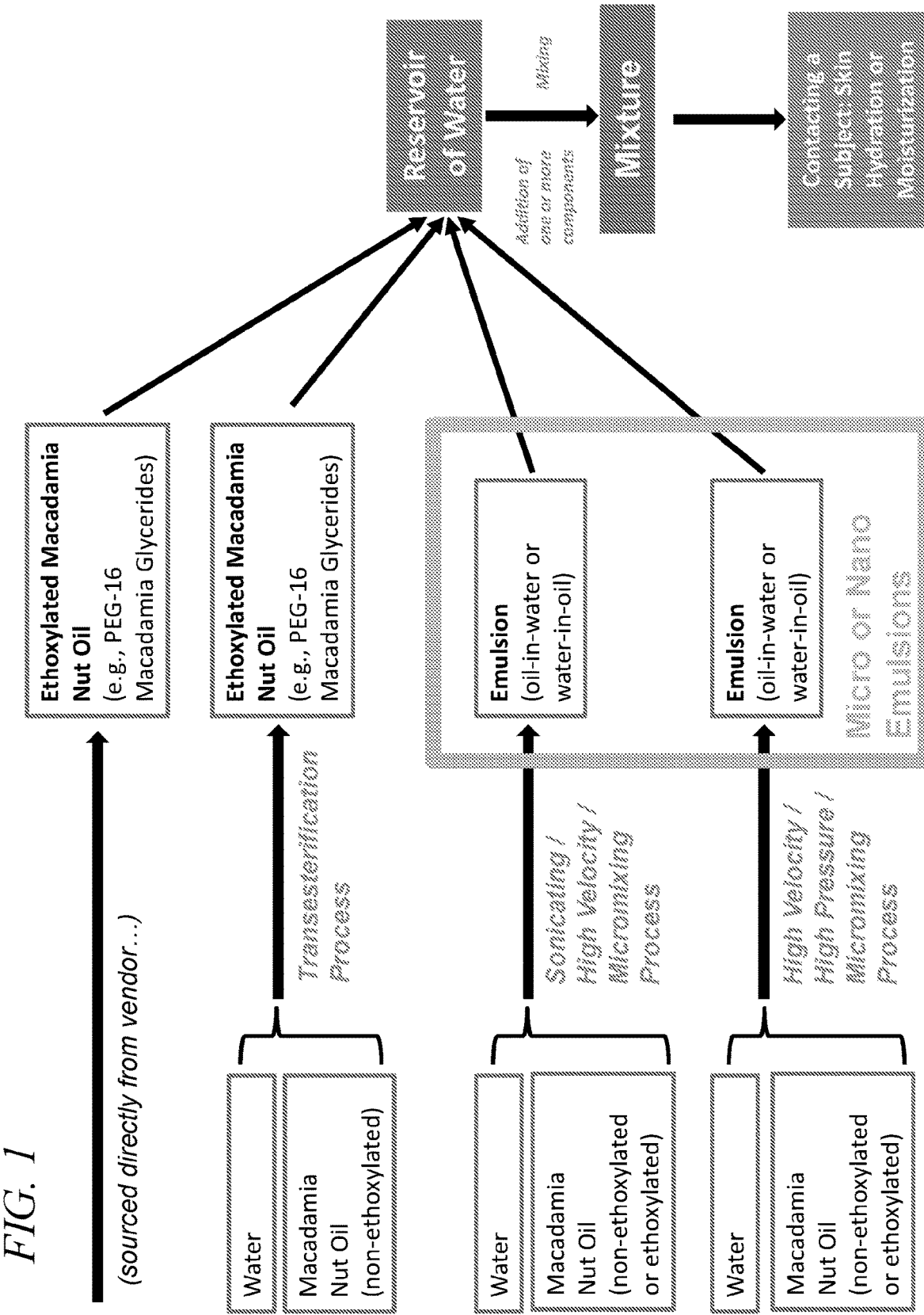
FIG. 1 is a flow diagram illustrating a number of non-limiting approaches for enhancing skin hydration or moisturization of a subject in accordance with some alternatives of the methods disclosed herein.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

DETAILED DESCRIPTION OF THE PREFERRED EMBODIMENT

It is to be understood by one of ordinary skill in the art that the present discussion is a description of exemplary embodiments only, and is not intended as limiting the broader aspects of the present disclosure, which broader aspects are embodied in the exemplary construction.

The present disclosure generally relates to methods and compositions for improving the level of water absorption and retention by the skin. In particular, in one aspect, the disclosure provides methods for enhancing hydration or moisturization of the skin of a subject (e.g., a human or animal such as a domestic animal or farm animal such as dog, cat, horse, cattle, pig, or sheep), by topically administering to the skin a mixture comprising or consisting of an ethoxylated oil and water. In another aspect, the disclosure provides methods for enhancing hydration or moisturization of the skin of a selected or identified subject (e.g., a human or animal such as a domestic animal or farm animal such as dog, cat, horse, cattle, pig or sheep) by topically administering to the skin of said subject a mixture comprising or consisting of water contacted with an ethoxylated oil, and optionally, additional components added only after the water is contacted with the ethoxylated oil. Also provided, in one aspect, are methods for making micro or nano emulsions that comprise, consist of, or consist essentially of a non-ethoxylated macadamia nut oil and water, wherein e.g., the non-ethoxylated macadamia nut oil and the water are the active ingredients. Additionally, in one aspect, are methods for increasing skin conductance and capacitance, while decreasing impedance, by topically administering to the skin of a selected or identified subject a mixture or emulsion comprising of or consisting of water contacted with an ethoxylated oil prior to inclusion of additional components in the water-ethoxylated oil mixture or emulsion. In another aspect, also provided are methods for preparing reservoirs of water by adding either an ethoxylated oil or a micro or nano emulsion to water to create a mixture for enhancing skin hydration or moisturization of a subject. In a further aspect, also provided are methods for making a mixture comprising or consisting of water contacted with an ethoxylated oil prior to inclusion of an additional component or compound in the mixture.

Definitions

Unless otherwise defined, all terms of art, notations and other scientific terms or terminology used herein are intended to have the meanings commonly understood by those skilled in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

The term "comprising" as used herein is synonymous with "including", "containing", or "characterized by", and is inclusive or open-ended and does not exclude additional, un-recited elements or method steps.

"Skin" as used herein, is meant to include skin on the face, neck, scalp, underarms, chest, back, arms, hands, legs, feet, buttocks and abdomen, preferably the hands, neck, face, and underarms. The invention is suitable for any skin type.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Headings, e.g., (a), (b), (i) etc., are presented merely for ease of reading the specification and claims. The use of headings in the specification or claims does not require the steps or elements be performed in alphabetical or numerical order or the order in which they are presented, unless otherwise specified.

Methods for Enhancing Hydration or Moisturization of the Skin

In one aspect, disclosed herein are methods for enhancing hydration or moisturization of the skin of a subject (e.g., a human or animal such as a domestic animal or farm animal such as dog, cat, horse, cattle, pig, or sheep), that comprise topically administering to the skin of the selected or identified subject a mixture comprising an ethoxylated oil and water or a micro or nano emulsion and water (FIG. 1). In some alternatives, the micro or nano emulsion comprises of a non-ethoxylated oil and water. In some alternatives, the micro or nano emulsion comprises of an ethoxylated oil and water. In some alternatives, the water is contacted with the ethoxylated oil prior to, optionally, combining the mixture with one or more additional components (FIG. 1). In some alternatives, the ethoxylated oil that can be used in the methods described herein can be a vegetable, plant, fruit, seed, marine, flower, nut, animal, or synthetic oil or fatty acid, fatty alcohol, or fatty amine therein having an average number of ethoxylations per molecule that is 10, 11, 12, 13, 14, 15, 16, 17, 18, or 19 or an average number of ethoxylations per molecule that is within a range defined by any two of the aforementioned values. In some alternatives, the ethoxylated oil can be unsaturated fatty acid. Preferable ethoxylated oils can be obtained or created from, for example, oleic acid, palmitoleic acid, apricot kernel oil, avocado oil, evening primrose oil, grape seed oil, hazelnut oil, pumpkinseed oil, rosehip oil, safflower oil, sunflower oil, walnut oil, wheat germ oil, neem oil, mink oil, lanolin, argan oil, Abyssinian oil, *Salvia Hispanica* oil (chia seed oil), Calophyllum Tacamahaca Seed oil (tamanu oil), squalane, sea buckthorn oil, meadowfoam oil, castor oil, jojoba oil, olive oil, corn oil, sesame oil, oenocarpus bataua oil, pentaclethra macroloba oil, or emu oil, or any combination therein. In some alternatives, preferred oils can be macadamia nut oil, jojoba oil, or meadowfoam oil, or any combination thereof. In some alternatives, the ethoxylated oil that can be used in the methods described herein is obtained or created from macadamia nut oil. Preferably, the average number of ethoxylations per molecule in the ethoxylated macadamia nut oil is 10, 11, 12, 13, 14, 15, 16, 17, 18, or 19 or an average number of ethoxylations per molecule that is within a range defined by any two of the aforementioned values. In a particularly preferred alternative, the ethoxylated oil is obtained from macadamia nut oil with 16 ethoxylations per molecule. In some alternatives, the amount of non-ethoxylated macadamia nut oil or ethoxylated macadamia nut oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts.

Depending on the intended applications, the amount of ethoxylated oil(s) in the mixture or micro or nano emulsion suitable for the methods described herein can vary. For example, in some alternatives, the methods for enhancing skin hydration or moisturization of the present disclosure can comprise a mixture or micro or nano emulsion comprising between 0.1% and 50% by weight or volume ethoxylated oil(s). That is, some alternatives of the methods described herein can comprise a mixture or micro or nano emulsion containing less than or equal to (but not zero) 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, or 50.0% ethoxylated oil(s) by weight or volume or an amount within a range defined by any two of the aforementioned amounts. In some preferred alternatives, the amount of ethoxylated oil in the mixture or micro or nano emulsion is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume, or an amount that is within a range defined by any two of the aforementioned amounts. In some preferred alternatives, the amount of ethoxylated oil in the mixture or micro or nano emulsion is 1%. In some preferred alternatives, the amount of ethoxylated oil in the mixture or micro or nano emulsion is 2%. In some preferred alternatives, the amount of ethoxylated oil in the mixture or micro or nano emulsion is 4%.

In some alternatives, the method for enhancing skin hydration will have one or more components added after the water and ethoxylated oil are contacted or mixed, such as xanthan gum, zinc dioxide, titanium dioxide, talc, silica, and a combination of phenoxyethanol, caprylyl glycol, ethylhexylglycerin, and hexylene glycol, sold under the trade name Botanistat PF-64. Other alternatives include one or more components such as glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides.

In some alternatives of the methods described herein, the mixture is formulated for topical administration. The terms "administration" and "administering", as used herein, refer to the delivery of a mixture by an administration route including parenteral, intranasal, ocular, ear canal, sublingual, buccal, mucosal, and/or oral administration. The term "topical administration" is used in its conventional sense to refer to delivery of an active agent to a body surface, such as, the skin, as in, for example, topical administration of a drug in the prevention or treatment of various skin disorders, the application of cosmetics and cosmeceuticals, including moisturizers, face or body sprays, body washes, facial cleansers, lotions, masks, sunscreens, and the like. Topical administration, in contrast to transdermal administration, provides a local rather than a systemic effect. As such, "topical administration" as used herein is limited to a surface deposition of the mixture, and excludes any mechanism of transdermal systemic delivery.

In some alternatives, the mixture formulated for topical administration contains drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and/or any mixtures thereof. In some alternatives, the mixture, which consists, consists essentially of, or comprises of drinking water, bottled water, sparkling water, sparkling mineral water, alkaline water, glacial water, coconut water, carbonated water, purified drinking water, natural water, spring water, natural spring water, artesian water, natural artesian water, mineral water or natural mineral water first contacted with ethoxylated oil, contains one or more of the following: Fiji® Water, Ice Mountain, Sparkletts, Zico, Vita Coco, Aquafina, Arrowhead Water, Dejà Blue, Crystal Geyser, Evian, Glacéau Smartwater, Glacéau Vitaminwater, Iceland Pure Spring Water, Nestlé® Pure Life®, Nestlé® Waters, Niagara, Poland Spring, Propel Fitness Water, San Pellegrino, Gerolsteiner, Ferrarelle, Perrier, Mountain Valley, Ty Nant, Volvic, Icelandic Glacial, Dasani, Deer Park, Ozarka, Voss, Vittel, Contrex, Acqua Panna, São Lourenço and Sierra Springs water and/or any mixtures thereof.

Generally, in the methods described herein, any topical formulation may be used as is known in the art, as long as the formulation preserves the moisturizing or hydrating activity of the mixture. In some alternatives, the mixture described herein is administered in a form selected from the group consisting of aqueous solution, spray, mist, liquid, cream, lotion, emulsion including water-in-oil, water-in-oil-in-water triple emulsion, oil-in-water emulsion, micro-emulsion or nano-emulsion, gel, semi-solid, paste, ointment, serum and/or milk.

In some alternatives, the mixture is further formulated with or into a leave-on product, a rinse-off or wash-off product, a pharmaceutical preparation, a dietary supplement, a personal care preparation, or a cosmetic preparation. In some alternatives, the ethoxylated oil and water mixture is further formulated with or into a base, a functional ingredient, a functional ingredient blend, an active ingredient, or an active ingredient blend. In some alternatives, the mixture is further formulated with or into a bar soap, a liquid soap, a hand soap, a body soap, a body wash, a shower gel, or a bubble bath. In some alternatives, the mixture is further formulated with or into a shaving cream, a shaving gel, an aftershave, a deodorant, a antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, or a skincare formula. In some alternatives, the mixture is further formulated with or into a sun care formula, an after sun formula, a foot care formula, or a hand care formula. In some alternatives, the mixture is further formulated with or into a shampoo, a hair conditioner, a hair care formula, a hair spray, a hair styling product, or a scalp care formula. In some alternatives, the mixture is further formulated with or into a self-tanner formula, a body care formula, such as a body moisturizer, a body spray, a body scrub, a body cleanser, a body exfoliator, or a body wipe. In some alternatives, the mixture is further formulated with or into a depilatory, a perfume, an eau de parfume, an eau de toilette, or an eau de cologne. In some alternatives, the mixture is further formulated with or into a dish soap, a laundry detergent, or a pain relief formula. In some alternatives, the mixture is further formulated with or into a toothpaste, a teeth cleaning formula, a lozenge, or a mouthwash. In some alternatives, the mixture is further formulated with or into a first aid product, a skin ailment product, a compromised skin product (e.g., to treat eczema, psoriasis or rosacea), an anti-septic product, an insect bite product, a blister relief product, a bunion relief product or a callus relief product. In some alternatives, the mixture is further formulated with or into a feminine care product, an anti-itching product, an anti-rash product or an anti-fungal product. In some alternatives, the mixture is further formulated with or into a pet care product or a pet grooming product. In some alternatives, the mixture is further formulated with or into a wound healing product, a burn relief product, a scar management product, a stretch mark product, a wart removal product, a hand sanitizer, a cold sore care product or an anti-cellulite product. In some alternatives, the mixture is further formulated with or into an eye drop or spray, a nasal drop or spray, an ear drop or spray or a mouth drop or spray. In some alternatives, the mixture is further formulated with or into a personal lubricant or a diaper product. In some alternatives, the mixture is further formulated with or into a dissolvable bead such as a shampoo or conditioner bead, moisturization bead in a preparation for one's face or body, or a bath bead. Technologies for manufacturing dissolvable beads with encapsulated oil that dissolve under predefined conditions and are suitable for both cosmetic and therapeutic purposes are known by those skilled in the art. Accordingly, it is contemplated that in some alternatives, the mixture is further formulated into dissolvable beads with different dissolution rates to provide for longer term delivery, stability, or reduction of oxidation of the ethoxylated oil.

In some alternatives, the topical formulations described herein can further comprise a cosmetically, dermatologically, or pharmaceutically acceptable diluent, carrier or excipient.

In some alternatives, the topical formulations described herein further comprise additives useful in the cosmetic, personal care, pharmaceutical and/or dermatological fields, including, but not limited to, fats, emulsifiers and co-emulsifiers, surfactants, co-surfactants, hydrophilic or lipophilic gelling agents, preservatives, solvents, co-solvents, emollients, humectants, stabilizers, fragrances, thickeners, fillers, hydrophilic and lipophilic filters, dyestuffs, mineral pigments as used in makeup, neutralizers, astringents, penetration-enhancing agents and polymers. The quantities of these various additives are those conventionally used in cosmetic, personal care, pharmaceutical and/or dermatological preparations as is known to a person skilled in the art. In some alternatives, the topical formulations described herein further comprise an essential oil, a makeup pigment, a tanning pigment, or a fragrance.

In some alternatives, the methods for enhancing hydration or moisturization of the skin described herein further comprise determining or measuring skin hydration or moisturization of the subject after administration of the mixture. One skilled in the art will readily appreciate that improvements in skin hydration or moisturization can be measured using known systems and techniques, including a number of methods and instruments that have been developed for studying skin physiology, biophysical properties, and function of the skin barrier. Generally, skin hydration or moisturization values can be determined by using any suitable techniques known in the art and can be determined by, for example, techniques developed for assessing skin hydration or moisturization based on one or more electrical properties of the skin such as measurement of resistance, alternating current conductivity (conductance), capacitance, and impedance of the skin surface as validated indicators of the hydration or moisture level of skin. For example, one skilled in the art will readily appreciate that skin hydration or moisturization can be determined by measuring electromagnetic radiation on the skin surface, or by determining change in the dielectric constant or dielectric permittivity due to variation in skin surface hydration or moisturization. Other non-limiting examples of suitable techniques for measuring skin hydration or moisturization in accordance with the methods described herein include determination of skin hydration or moisturization through measurements of thermal conductivity, or assessment of the skin hydration or moisturization value based on at least one elastographic parameter of the skin.

Various techniques and systems have been developed for measuring electrical conductance of the skin surface as an indicator of stratum corneum water content. Non-limiting examples of such systems and methods include (1) transepidermal water loss (TEWL) which measures the rate of evaporation of water from the skin surface; (2) attenuated total reflectance Fourier transform infrared (ATR-FTIR) technique which relies on the ambient conditions and is reported to be most effective when measuring the water content of the uppermost stratum corneum; (3) confocal raman spectroscopy; (4) optical fiber near infrared (NIR) spectroscopy (Omar and MatJafri (2012); *Optical Fiber Near Infrared Spectroscopy for Skin Moisture Measurement, Selected Topics on Optical Fiber Technology*, Dr Moh. Yasin (Ed.)); (5) electron microscopy; and (6) Fourier transform near-infrared (FT-NIR) spectrophotometer.

The phrase "transepidermal water loss" (TEWL), as used herein, refers to water loss through the epidermis generally exacerbated by skin barrier damage caused by environmental factors associated with dry skin, such as detergents, soaps, solvents or ultraviolet light which tend to remove or damage the skin's protective lipids, resulting in such water loss. The measurement of TEWL is therefore important for evaluating the efficiency of the skin water barrier. Typically, this measurement can be performed using a Tewameter® device (Courage+Khazaka Electronic, Germany), and the measurement of the water evaporation is based on the diffusion principle in an open chamber.

In some alternatives, determining or measuring skin hydration can be performed using Attenuated Total Reflectance/Fourier Transform Infrared Spectrophotometric (ATR/FTIR) analysis in which skin studies are conducted and analyzed based on the reflection of energy at the prism/skin interface. Generally, ATR/FTIR studies involve contact of the skin sample and prism. A hydration procedure is employed in order to increase the softness and flexibility of the skin surface which results in a less variable contact between the skin and prism. Systems and procedures suitable for ATR/FTIR analysis of skin hydration are known in the art.

In some alternatives, electrical conductance can be measured as an indicator of skin hydration or moisturization when a constant frequency alternating current is applied to skin. The skin hydration or moisture can then be calculated from the electric conductivity that is dependent on the water content of the skin (See Woo et al., Anal. Chem, 73, pp. 4964-4971, 2001). Conductance has been reported to correlate well with the superficial portion of the stratum corneum even when the electrical field on the stratum corneum is non-homologous. Skin conductance can be measured using equipment such as Skicon® 200 hygrometers.

Other equipment suitable to measure skin surface capacitance as an indicator of skin hydration or moisturization, in accordance with some alternatives of the methods disclosed herein, may include Corneometer® hydrometers (Courage+Khazaka Electronic, Germany), ServoMed® evaporimeters, Nova DPM 9003, and DermaLab®-Hydration Probe and Module (Cortex Technology, Denmark). Besides conventional corneometry, additional methods for measuring hydration or moisturization may include nuclear magnetic resonance (NMR-5) spectroscopy and transient thermal transfer (TTT).

In some alternatives, a Tewameter® device (Courage+Khazaka Electronic, Germany), a ServoMed® evaporimeter, or a DermaLab®-TEWL Probe and Module (Cortex Technology, Denmark) can be used to measure transepidermal water loss (TEWL) as an assessment of skin hydration or moisturization value. Increases in TEWL can be generally attributed to a breakdown in the barrier properties of the skin. Decreases in TEWL can be generally attributed to the associated improvement in barrier properties (See Morrison, J. Soc. Cosmet. Chem. 43, 161-167, 1992).

Methods for the Preparation of a Reservoir of Water to Create a Mixture

Some alternatives disclosed herein relate to methods for preparing a reservoir of water, which provides enhanced skin hydration or moisturization to a subject by adding to the water an ethoxylated oil or a micro or nano emulsion to form a mixture (FIG. 1). Those skilled in the art will understand that any appropriately configured reservoir of water will suffice in order to practice the methods described herein. In this regard, the term "reservoir" as used herein is to be construed as any appropriate body of water that may be used in conjunction with a method for enhancing hydration or moisturization of the skin of a subject (e.g., a human or animal such as a domestic animal or farm animal such as dog, cat, horse, cattle, pig, or sheep), in need thereof. Such a reservoir may, for example, also be provided by water held in a tank or a container having an appropriate configuration for the purpose of being applied to the skin.

In some alternatives, the reservoir of water can be a container, a mixing vessel, a mixing tank, or a mixing kettle. In some alternatives, the reservoir of water can be a water softener system, a water purification system, or a water filtration system. In some alternatives, the reservoir of water can be a drinking water system or a drinking fountain. In some alternatives, other suitable reservoirs of water can include but are not limited to a swimming pool, a pool, a whirlpool, a steam room, a sauna, a storage tank, a sink, a bath, a tub, or a shower.

In some alternatives, the methods described herein can comprise selecting a subject to receive enhanced skin hydration or moisturization, providing a reservoir of water, and adding to the reservoir of water an ethoxylated oil or a micro or nano emulsion to form a mixture. One skilled in the art will immediately appreciate that the ethoxylated oil or micro or nano emulsion can be added to stagnant, sprayed or flowing water. Accordingly, in some alternatives of the methods described herein, the ethoxylated oil or micro or nano emulsion is added to a stagnant body of water and then mixed to form a mixture reservoir. In some alternatives, adding an ethoxylated oil comprises metering the ethoxylated oil in-line, in real time, to sprayed or flowing water and mixing the ethoxylated oil with the water so as to form a sprayable or flowing mixture. In some alternatives, adding a micro or nano emulsion comprises metering the micro or nano emulsion in-line, in real time, to sprayed or flowing water and mixing the micro or nano emulsion with the water so as to form a sprayable or flowing mixture.

In some alternatives of the methods described herein, the ethoxylated oil can be a vegetable, plant, fruit, seed, marine, flower, nut, animal, or synthetic oil or fatty acid, fatty alcohol, or fatty amine. In some alternatives, the fatty acid is unsaturated fatty acid. In some alternatives, the ethoxylated oil that can be used in the methods described herein is obtained or created from macadamia nut oil. Preferably, the ethoxylated oil has an average number of ethoxylations per molecule that is 10, 11, 12, 13, 14, 15, 16, 17, 18, or 19 or an average number of ethoxylations per molecule that is within a range defined by any two of the aforementioned values. In a particularly preferred alternative, the ethoxylated oil is obtained from macadamia nut oil with 16 ethoxylations per molecule.

Depending on the intended applications, the amount of ethoxylated oil(s) suitable for the methods described herein can vary. For example, in some alternatives, the methods for preparing a reservoir of water described herein can comprise a mixture described herein that comprises between 0.1% and 50% by weight or volume ethoxylated oil(s) and water. That is, some alternatives of the methods described herein can comprise a mixture containing less than (but not zero) or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, or 50.0% ethoxylated oil(s) by weight or volume or an amount that is within a range defined by any two of the aforementioned amounts. In some preferred alternatives, the amount of ethoxylated oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts. In some preferred alternatives, the amount of ethoxylated oil in the mixture is 1%. In some preferred alternatives, the amount of ethoxylated oil in the mixture is 2%. In some preferred alternatives, the amount of ethoxylated oil in the mixture is 4%.

In some alternatives, the reservoir of water prepared by the methods described herein further comprises an essential oil, a pigment, or a fragrance. In some alternatives, additional moisturizing or hydrating agents can be added to the reservoir of water of the present disclosure. For example, moisturizing or hydrating agents can be added to one or more parts of a bath treatment formulation to make a moisturizing or hydrating bath. This would give users a "spa-like" experience of a relaxing soak in skin beneficial moisturizing or hydrating ingredients and allow such users an easy, convenient alternative to topically applying skin lotion post-bath while relieving stress. Various components could be added to the reservoir of water to provide this benefit including, but not limited to, moisturizing and hydrating agents which impart some moisturizing or hydration benefit to the skin. These include, but are not limited to, humectants such as glycerin, glycols, and sorbitol; synthetic oils such as mineral oil and petrolatum; natural oils such as jojoba oil, sunflower oil, and safflower oil; silicones such as dimethicone and cyclomethicone; esters such as isopropyl palmitate and caprylic or capric triglyceride; butters such as coffee butter, cocoa butter, and shea butter; barrier ingredients such as fatty acids including unsaturated fatty acids, fatty alcohols, and waxes. In some alternatives, hyaluronic acid and/or urea are also added to the reservoir of water.

In some alternatives, the methods for enhancing hydration or moisturization of the skin described herein further comprise observing, determining or measuring skin hydration or moisturization in the subject after receiving enhanced skin hydration or moisturization.

In some alternatives, the mixture is further formulated with or into a leave-on product, a rinse-off or wash-off product, a pharmaceutical preparation, a dietary supplement, a personal care preparation, or a cosmetic preparation. In some alternatives, the ethoxylated oil and water mixture is further formulated with or into a base, a functional ingredient, a functional ingredient blend, an active ingredient, or an active ingredient blend. In some alternatives, the mixture is further formulated with or into a bar soap, a liquid soap, a hand soap, a body soap, a body wash, a shower gel, or a bubble bath. In some alternatives, the mixture is further formulated with or into a shaving cream, a shaving gel, an aftershave, a deodorant, a antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, or a skincare formula. In some alternatives, the mixture is further formulated with or into a sun care formula, an after sun formula, a foot care formula, or a hand care formula. In some alternatives, the mixture is further formulated with or into a shampoo, a hair conditioner, a hair care formula, a hair spray, a hair styling product, or a scalp care formula. In some alternatives, the mixture is further formulated with or into a self-tanner formula, a body care formula, such as a body moisturizer, a body spray, a body scrub, a body cleanser, a body exfoliator, or a body wipe. In some alternatives, the mixture is further formulated with or into a depilatory, a perfume, an eau de parfume, an eau de toilette, or an eau de cologne. In some alternatives, the mixture is further formulated with or into a dish soap, a laundry detergent, or a pain relief formula. In some alternatives, the mixture is further formulated with or into a toothpaste, a teeth cleaning formula, a lozenge, or a mouthwash. In some alternatives, the mixture is further formulated with or into a first aid product, a skin ailment product, a compromised skin product (e.g., to treat eczema, psoriasis or rosacea), an anti-septic product, an insect bite product, a blister relief product, a bunion relief product or a callus relief product. In some alternatives, the mixture is further formulated with or into a feminine care product, an anti-itching product, an anti-rash product or an anti-fungal product. In some alternatives, the mixture is further formulated with or into a pet care product or a pet grooming product. In some alternatives, the mixture is further formulated with or into a wound healing product, a burn relief product, a scar management product, a stretch mark product, a wart removal product, a hand sanitizer, a cold sore care product or an anti-cellulite product. In some alternatives, the mixture is further formulated with or into an eye drop or spray, a nasal drop or spray, an ear drop or spray or a mouth drop or spray. In some alternatives, the mixture is further formulated with or into a personal lubricant or a diaper product. In some alternatives, the mixture is further formulated into dissolvable beads with different dissolution rates to provide for longer term delivery, stability, and/or reduction of oxidation of the oil.

Methods for Manufacturing Micro or Nano Emulsions Containing Macadamia Nut Oil and Water In one aspect, some alternatives of the present disclosure relate to methods of making micro or nano emulsions, which comprise a non-ethoxylated oil and water (FIG. 1). As used herein, the term "micro or nano emulsion" refers to a dispersion of two immiscible liquids, one liquid phase being "dispersed" and the other being "continuous". In general, micron- or nano-sized micelles in micro or nano emulsions provide two very desirable qualities of cosmetics, personal care products, and pharmaceuticals, namely greater solubility and stability, and higher bioavailability and a higher dissolution rate. The micro or nano emulsions prepared by the methods disclosed herein can be in the form of either oil-in-water or water-in-oil, which can be selected as appropriate depending on applications and purposes.

Accordingly, in some alternatives, the micro emulsions prepared by the methods described herein comprise micro-sized micelles having a mean or average micelle diameter of from about 1 micron to about 5 microns, e.g., 1.0 microns, 1.5 microns, 2.0 microns, 2.5 microns, 3.0 microns, 3.5 microns, 4.0 microns, 4.5 microns, or 5.0 microns in diameter or a number within a range defined by any two of the aforementioned diameters.

In some alternatives, the nano emulsions made by the methods described herein comprise nano-sized micelles having a mean or average micelle diameter that is preferably greater than zero microns but not more than 0.5 microns in diameter, preferably not more than 0.04 microns in diameter and most preferably not more than 0.01 microns in diameter or a number within a range defined by any two of the aforementioned diameters.

In some alternatives, the average micelle diameter of the micro and nano emulsions prepared by the methods described herein can be determined by a number of suitable techniques and systems including, but not limited to, photon correlation spectroscopy (PCS), total-intensity light scattering (TILS), static light scattering (SLS), dynamic light scattering (DLS), laser diffraction (LD), small-angle neutron scattering (SANS), transmission electron microscopy (TEM), nuclear magnetic resonance (NMR), spectrophotometric measurements, and small angle X-ray scattering. These and other methods for the characterization of emulsions are known in the art. A particular suitable method for determining micelle or particle size/diameter is laser diffraction or dynamic light scattering with instruments manufactured by, for example, Malvern Instruments (Malvern, United Kingdom) such as a Malvern Zetasizer, or by Horiba International (Kyoto, Japan) such as a Particle Size Analyzer.

In some alternatives, the methods of making micro or nano emulsions disclosed herein involve an impinging fluid jet stream technique in which two impinging jets are used to achieve high intensity mixing of fluids so as to form substantially homogeneous micro or nano micelles. Apparatuses and processes useful for methods of impinging jets to achieve high intensity mixing of non-ethoxylated oil and water are generally known and can be found in further detail in, for example, U.S. Pat. Nos. 5,314,506 and 6,302,958, both of which are incorporated by reference herein. Typically, the process by which these micro or nano micelles are produced involves two impinging liquid jets positioned within a well stirred flask to achieve high intensity mixing. At the point where the two jets strike one another a very high level of supersaturation exists. As a result of this high supersaturation, crystallization occurs extremely rapidly within the small mixing volume at the impingement point of the two liquids. Since new crystals are constantly nucleating at the impingement point, a very large number of crystals, i.e. micro or nano micelles, are produced.

Some alternatives disclosed herein relate to methods of making micro or nano emulsions that include an oil and water including: sonicating a first fluid jet stream including the oil and a second fluid jet stream including water, wherein the sonicating is performed by positioning a tip of a sonication probe within a gap defined between a first fluid jet, which emits the first fluid jet stream, and a second fluid jet, which emits the second fluid jet stream. The first and the second fluid jets are positioned such that the fluid jet streams from the first fluid jet and the second fluid jet impinge in the gap between the jets so as to create a point of high turbulence at the point of impact of the fluid jet streams. In the methods, each of the fluid jet streams have sufficient linear velocity to achieve high intensity mixing of the oil and water, preferably non-ethoxylated macadamia nut oil or ethoxylated macadamia nut oil and water, and the sonication probe provides ultrasonic energy in the immediate vicinity of the impinging fluid jet streams which thereby generates a micro or nano emulsion that comprises oil and water.

In some alternatives of the methods described herein, the first fluid jet stream has a linear velocity of at least 100, 200, 300, 400, 500, 600, 700, 800, or 900 m/s or a linear velocity within a range defined by any two of the aforementioned linear velocities. In some alternatives, the second fluid jet stream has a linear velocity of at least 100, 200, 300, 400, 500, 600, 700, 800, or 900 m/s or a linear velocity within a range defined by any two of the aforementioned linear velocities. In some alternatives, the first jet stream and the second jet stream have the same linear velocity. In some alternatives, the first jet stream and the second jet stream have different linear velocities.

In some alternatives of the methods described herein, the first and second fluid jet streams are contacted under a pressure of 25,000-50,000 psi or at a pressure that is within a range defined by any two numbers within the range of 25,000-50,000 psi and, after the first and second fluid jet streams are contacted under the pressure, the resultant micro or nano emulsions that include the oil, preferably non-ethoxylated macadamia nut oil or ethoxylated macadamia nut oil, and water is brought to atmospheric pressure.

In some alternatives, the sonicating is conducted above the freezing point of water but less than or equal to ambient temperature such as, for example, 1, 2, 3, 4, 5, 6, 7, 8, 9, 10, 11, 12, 13, 14, 15, 16, 17, 18, 19, 20, 21, 22, 23, 24, or 25 degrees Celsius or at a temperature that is within a range defined by any two of the aforementioned temperatures.

In some alternatives, the temperature of the first fluid jet stream is above the freezing point of water but less than or equal to ambient temperature such as, for example, 1, 2, 3, 4, 5, 6, 7, 8, 9, 10, 11, 12, 13, 14, 15, 16, 17, 18, 19, 20, 21, 22, 23, 24, or 25 degrees Celsius or at a temperature that is within a range defined by any two of the aforementioned temperatures.

In some alternatives, the temperature of the second fluid jet stream is above the freezing point of water but less than or equal to ambient temperature such as, for example, 1, 2, 3, 4, 5, 6, 7, 8, 9, 10, 11, 12, 13, 14, 15, 16, 17, 18, 19, 20, 21, 22, 23, 24, or 25 degrees Celsius or at a temperature that is within a range defined by any two of the aforementioned temperatures.

In some alternatives, the temperature of the first fluid jet stream and the temperature of the second fluid jet stream are the same. In some alternatives, the temperature of the first fluid jet stream and the temperature of the second fluid jet stream are different.

In some alternatives of this and other aspects of the disclosure, the micro or nano emulsions prepared by the methods disclosed herein comprise a non-ethoxylated macadamia nut oil and water. In some alternatives, the macadamia nut oil is ethoxylated.

In some alternatives, the mixtures prepared by the methods disclosed herein consist of an ethoxylated oil and water. In some alternatives, the ethoxylated oil can be a vegetable, plant, fruit, seed, marine, flower, nut, animal, or synthetic oil or fatty acid, unsaturated fatty acid, fatty alcohol, or fatty amine having at least 10, 11, 12, 13, 14, 15, 16, 17, 18, 19, or more ethoxylations per molecule. Preferable ethoxylated oils can be obtained or created from, for example, palmitoleic acid, neem oil, mink oil, sea buckthorn oil, castor oil, jojoba oil, corn oil, and emu oil. In some alternatives, preferred oils can be macadamia nut oil, jojoba oil, or meadowfoam oil, or any combination thereof. In some alternatives, the ethoxylated oil that can be used in the methods described herein is obtained or created from macadamia nut oil. Preferably, the ethoxylated oil has an average number of ethoxylations per molecule that is 10, 11, 12, 13, 14, 15, 16, 17, 18, or 19 or an average number of ethoxylations per molecule that is within a range defined by any two of the aforementioned values. In a particularly preferred alternative, the ethoxylated oil is obtained from macadamia nut oil with 16 ethoxylations per molecule.

Depending on the intended applications, the amount of ethoxylated oil(s) suitable for the methods described herein can vary. For example, in some alternatives, the amount of non-ethoxylated macadamia nut oil or ethoxylated macadamia nut oil in the micro or nano emulsions or mixtures is between 0.1% and 50%. That is, some alternatives of the methods described herein can comprise a micro or nano emulsion or mixture containing less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, or 50.0% non-ethoxylated oil(s) or ethoxylated oil(s) by weight or volume or an amount that is within a range defined by any two of the aforementioned amounts. In some preferred alternatives, the amount of non-ethoxylated oil or ethoxylated oil in the micro or nano emulsions or mixtures is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume, or an amount that is within a range defined by any two of the aforementioned amounts. In some preferred alternatives, the amount of non-ethoxylated oil or ethoxylated oil in the mixtures is 1%. In some preferred alternatives, the amount of non-ethoxylated oil or ethoxylated oil in the mixtures is 2%. In some preferred alternatives, the amount of non-ethoxylated oil or ethoxylated oil in the mixtures is 4%.

In some alternatives, the methods of making a mixture described herein further comprises adding an essential oil, a pigment, or a fragrance to the mixture. In some alternatives, also included in the mixtures are additives useful in the cosmetic, personal care, pharmaceutical and/or dermatological fields, including, but not limited to, fats, emulsifiers and co-emulsifiers, surfactants and co-surfactants, hydrophilic or lipophilic gelling agents, preservatives, solvents, co-solvents, emollients, humectants, stabilizers, fragrances, thickeners, fillers, hydrophilic and lipophilic filters, dyestuffs, mineral pigments as used in makeup, neutralizers, astringents, penetration-enhancing agents and polymers. The quantities of these various additives are those conventionally used in cosmetic, personal care, pharmaceutical and/or dermatological preparations as is known to a person skilled in the art.

In some alternatives, the methods of making micro or nano emulsions described herein further include adding the micro or nano emulsions to a reservoir of water and thereby contacting a subject with this mixture, which is the mixture of micro or nano emulsions and water (FIG. 1). Those skilled in the art will readily appreciate that the micro or nano emulsions can be added to stagnant, sprayed or flowing water. Accordingly, in some alternatives of the methods described herein, the micro or nano emulsions are added to a stagnant body of water and mixed to form a reservoir of stagnant mixture. In some alternatives, the methods described herein further comprise contacting a subject with the reservoir of stagnant mixture. Suitable reservoirs of water include, but are not limited to, water contained in a container, a mixing vessel, a mixing tank, a mixing kettle, a water softener system, a water purification system, a water filtration system, a drinking water system, a drinking fountain, a swimming pool, a pool, a whirlpool, a steam room, a sauna, a storage tank, a sink, a bath, a tub, and a shower. In some alternatives, the micro or nano emulsions are added by metering in-line, in real time, to sprayed or flowing water, mixing the micro or nano emulsion with the sprayed or flowing water to create a sprayable or flowable mixture, and contacting a subject with such sprayable or flowable mixture.

In some alternatives, the methods of making mixtures described herein further comprise observing, determining or measuring skin hydration or moisturization of the subject after contacting the subject with the mixture.

In some alternatives, the methods of making mixtures described herein further include introducing the mixture into a leave-on product, a rinse-off or wash-off product, a pharmaceutical preparation, a dietary supplement, a personal care preparation, or a cosmetic preparation. In some alternatives, the ethoxylated oil and water mixture is further formulated with or into a base, a functional ingredient, a functional ingredient blend, an active ingredient, or an active ingredient blend. In some alternatives, the mixture is further formulated with or into a bar soap, a liquid soap, a hand soap, a body soap, a body wash, a shower gel, or a bubble bath. In some alternatives, the mixture is further formulated with or into a shaving cream, a shaving gel, an aftershave, a deodorant, a antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, or a skincare formula. In some alternatives, the mixture is further formulated with or into a sun care formula, an after sun formula, a foot care formula, or a hand care formula. In some alternatives, the mixture is further formulated with or into a shampoo, a hair conditioner, a hair care formula, a hair spray, a hair styling product, or a scalp care formula. In some alternatives, the mixture is further formulated with or into a self-tanner formula, a body care formula, such as a body moisturizer, a body spray, a body scrub, a body cleanser, a body exfoliator, or a body wipe. In some alternatives, the mixture is further formulated with or into a depilatory, a perfume, an eau de parfume, an eau de toilette, or an eau de cologne. In some alternatives, the mixture is further formulated with or into a dish soap, a laundry detergent, or a pain relief formula. In some alternatives, the mixture is further formulated with or into a toothpaste, a teeth cleaning formula, a lozenge, or a mouthwash. In some alternatives, the mixture is further formulated with or into a first aid product, a skin ailment product, a compromised skin product (e.g., to treat eczema, psoriasis or rosacea), an anti-septic product, an insect bite product, a blister relief product, a bunion relief product or a callus relief product. In some alternatives, the mixture is further formulated with or into a feminine care product, an anti-itching product, an anti-rash product or an anti-fungal product. In some alternatives, the mixture is further formulated with or into a pet care product or a pet grooming product. In some alternatives, the mixture is further formulated with or into a wound healing product, a burn relief product, a scar management product, a stretch mark product, a wart removal product, a hand sanitizer, a cold sore care product or an anti-cellulite product. In some alternatives, the mixture is further formulated with or into an eye drop or spray, a nasal drop or spray, an ear drop or spray or a mouth drop or spray. In some alternatives, the mixture is further formulated with or into a personal lubricant or a diaper product. In some alternatives, the mixture is further formulated into dissolvable beads with different dissolution rates to provide for longer term delivery, stability, and/or reduction of oxidation.

In another aspect, as also illustrated in FIG. 1, some alternatives of the present disclosure relate to methods of making a micro or nano emulsion that comprises a non-ethoxylated macadamia nut oil and water including: transesterification of a non-ethoxylated macadamia nut oil in the presence of water to generate an ethoxylated macadamia nut oil; and mixing the resulting ethoxylated macadamia nut oil with water to create a mixture.

Methods for Increasing Conductance and Capacitance in Human Skin

Some alternatives disclosed herein relate to methods for increasing conductance or capacitance in the skin of a subject, (e.g., a human or animal such as a domestic animal or farm animal such as dog, cat, horse, cattle, pig or sheep) while decreasing impedance of the skin of the same subject, that comprise topically administering to the skin of the selected or identified subject a mixture comprising of an ethoxylated oil and water, and optionally adding one or more components or compounds, wherein the water is contacted with the ethoxylated oil prior to, optionally, combining the mixture with one or more additional components or compounds (FIG. 1). In some alternatives, the ethoxylated oil that can be used in the methods described herein can be a vegetable, plant, fruit, seed, marine, flower, nut, animal, or synthetic oil or fatty acid, fatty alcohol, or fatty amine therein having an average number of ethoxylations per molecule that is 10, 11, 12, 13, 14, 15, 16, 17, 18, or 19 or an average number of ethoxylations per molecule that is within a range defined by any two of the aforementioned values. In some alternatives, the ethoxylated oil can be unsaturated fatty acid. Preferable ethoxylated oils can be obtained or created from, for example, oleic acid, palmitoleic acid, apricot kernel oil, avocado oil, evening primrose oil, grape seed oil, hazelnut oil, pumpkinseed oil, rosehip oil, safflower oil, sunflower oil, walnut oil, wheat germ oil, neem oil, mink oil, lanolin, argan oil, Abyssinian oil, *Salvia Hispanica* oil (chia seed oil), Calophyllum Tacamahaca Seed oil (tamanu oil), squalane, sea buckthorn oil, meadowfoam oil, castor oil, jojoba oil, olive oil, corn oil, sesame oil, oenocarpus bataua oil, pentaclethra macroloba oil, or emu oil, or any combination thereof. In some alternatives, the ethoxylated oil that can be used in the methods described herein is obtained or created from macadamia nut oil. Preferably, the average number of ethoxylations per molecule in the ethoxylated macadamia nut oil is 10, 11, 12, 13, 14, 15, 16, 17, 18, or 19 or an average number of ethoxylations per molecule that is within a range defined by any two of the aforementioned values. In a particularly preferred alternative, the ethoxylated oil is obtained from macadamia nut oil with 16 ethoxylations per molecule. In some alternatives, the amount of ethoxylated macadamia nut oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts.

Depending on the intended application, the amount of ethoxylated oil(s) in the mixture suitable for the methods described herein can vary. For example, in some alternatives, the methods for increasing conductance or capacitance in skin of the present disclosure can comprise a mixture comprising between 0.1% and 50% by weight or volume of ethoxylated oil(s). That is, some alternatives of the methods described herein can comprise a mixture containing less than or equal to (but not zero) 0.1%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, or 50.0% ethoxylated oil(s) by weight or volume or an amount within a range defined by any two of the aforementioned amounts. In some preferred alternatives, the amount of ethoxylated oil(s) in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts.

In some alternatives, the method for increasing conductance or capacitance of the skin of the selected subject (e.g., a human or animal such as a domestic animal or farm animal such as dog, cat, horse, cattle, pig, or sheep) will have one or more components added after the water is contacted with ethoxylated oil, such as xanthan gum, zinc dioxide, titanium dioxide, talc, silica, and a combination of phenoxyethanol, caprylyl glycol, ethylhexylglycerin, and hexylene glycol, sold under the trade name Botanistat PF-64. Other component alternatives include one or more components such as glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides.

In some alternatives of the methods described herein, the mixture is formulated for topical administration. The terms "administration" and "administering", as used herein, refer to the delivery of a mixture by an administration route including parenteral, intranasal, ocular, ear canal, sublingual, buccal, mucosal, and/or oral administration. The term "topical administration" is used herein in its conventional sense to refer to delivery of an active agent to a body surface, such as, the skin, as in, for example, topical administration of a drug in the prevention or treatment of various skin disorders, the application of cosmetics and cosmeceuticals, including moisturizers, face or body sprays, body washes, facial cleansers, lotions, masks, sunscreens, and the like. Topical administration, in contrast to transdermal administration, provides a local rather than a systemic effect. As such, "topical administration" as used herein is limited to a surface deposition of the mixture, and excludes any mechanism of transdermal systemic delivery.

In some alternatives, the mixture formulated for topical administration contains drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and/or any mixtures thereof. In some alternatives, the mixture, which consists, consists essentially of, or comprises of drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water first contacted with ethoxylated oil, contains one or more of the following: Fiji® Water, Ice Mountain, Sparkletts, Zico, Vita Coco, Aquafina, Arrowhead Water, Dejà Blue, Crystal Geyser, Evian, Glacéau Smartwater, Glacéau Vitaminwater, Iceland Pure Spring Water, Nestlé® Pure Life®, Nestlé® Waters, Niagara, Poland Spring, Propel Fitness Water, San Pellegrino, Gerolsteiner, Ferrarelle, Perrier, Mountain Valley, Ty Nant, Volvic, Icelandic Glacial, Dasani, Deer Park, Ozarka, Voss, Vittel, Contrex, Acqua Panna, São Lourenço and Sierra Springs water and/or any mixtures thereof.

Generally, in the methods described herein, any topical formulation may be used as is known in the art, as long as the formulation preserves the hydrating or moisturizing activity of the mixture. In some alternatives the mixture is further formulated with or into a leave-on product, a rinse-off or wash-off product, a pharmaceutical preparation, a dietary supplement, a personal care preparation, or a cosmetic preparation. In some alternatives, the ethoxylated oil and water mixture is further formulated with or into a base, a functional ingredient, a functional ingredient blend, an active ingredient, or an active ingredient blend. In some alternatives, the mixture is further formulated with or into a bar soap, a liquid soap, a hand soap, a body soap, a body wash, a shower gel, or a bubble bath. In some alternatives, the mixture is further formulated with or into a shaving cream, a shaving gel, an aftershave, a deodorant, a antiperspirant, an acne treatment formula, a lip care formula, a lip plumper, a face care formula, such as a facial moisturizer, a facial cleanser, a facial wash, a facial toner, a facial astringent, a facial clarifyer, a facial mist, a facial spray, a facial mask, a facial exfoliator, a facial wipe, a color cosmetic, a makeup remover, a makeup foundation, a makeup concealer, or a sprayable makeup setting agent, or a skincare formula. In some alternatives, the mixture is further formulated with or into a sun care formula, an after sun formula, a foot care formula, or a hand care formula. In some alternatives, the mixture is further formulated with or into a shampoo, a hair conditioner, a hair care formula, a hair spray, a hair styling product, or a scalp care formula. In some alternatives, the mixture is further formulated with or into a self-tanner formula, a body care formula, such as a body moisturizer, a body spray, a body scrub, a body cleanser, a body exfoliator, or a body wipe. In some alternatives, the mixture is further formulated with or into a depilatory, a perfume, an eau de parfume, an eau de toilette, or an eau de cologne. In some alternatives, the mixture is further formulated with or into a dish soap, a laundry detergent, or a pain relief formula. In some alternatives, the mixture is further formulated with or into a toothpaste, a teeth cleaning formula, a lozenge, or a mouthwash. In some alternatives, the mixture is further formulated with or into a first aid product, a skin ailment product, a compromised skin product (e.g., to treat eczema, psoriasis or rosacea), an anti-septic product, an insect bite product, a blister relief product, a bunion relief product or a callus relief product. In some alternatives, the mixture is further formulated with or into a feminine care product, an anti-itching product, an anti-rash product or an anti-fungal product. In some alternatives, the mixture is further formulated with or into a pet care product or a pet grooming product. In some alternatives, the mixture is further formulated with or into a wound healing product, a burn relief product, a scar management product, a stretch mark product, a wart removal product, a hand sanitizer, a cold sore care product or an anti-cellulite product. In some alternatives, the mixture is further formulated with or into an eye drop or spray, a nasal drop or spray, an ear drop or spray or a mouth drop or spray. In some alternatives, the mixture is further formulated with or into a personal lubricant or a diaper product. In some alternatives, the mixture is further formulated with or into a dissolvable bead such as a shampoo or conditioner bead, moisturization bead in a preparation for one's face or body, or a bath bead. Technologies for manufacturing dissolvable beads with encapsulated oil that dissolve under predefined conditions and are suitable for both cosmetic and therapeutic purposes are known by those skilled in the art. Accordingly, it is contemplated that in some alternatives, the mixture is further formulated into dissolvable beads with different dissolution rates to provide for longer term delivery, stability, or reduction of oxidation of the ethoxylated oil(s).

In some alternatives, the topical formulations described herein can further comprise a cosmetically, dermatologically, or pharmaceutically acceptable diluent, carrier or excipient.

In some alternatives, the topical formulations described herein further comprise additives useful in the cosmetic, personal care, pharmaceutical and/or dermatological fields, including, but not limited to, fats, emulsifiers and co-emulsifiers, surfactants, co-surfactants, hydrophilic or lipophilic gelling agents, preservatives, solvents, co-solvents, emollients, humectants, stabilizers, fragrances, thickeners, fillers, hydrophilic and lipophilic filters, dyestuffs, mineral pigments as used in color cosmetics, makeup, neutralizers, astringents, penetration-enhancing agents and polymers. The quantities of these various additives are those conventionally used in cosmetic, personal care, pharmaceutical and/or dermatological preparations as is known to a person skilled in the art. In some alternatives, the topical formulations described herein further comprise an essential oil, a makeup pigment, a tanning pigment, or a fragrance.

The term "reservoir", as used herein, is to be construed as any appropriate body of water that may be used in conjunction with methods for increasing conductance and capacitance of the skin of the selected or identified subject. In some alternatives, the methods for increasing conductance and capacitance of the skin of the selected or identified subject, and decreasing impedance of the same subject's skin, described herein, further comprise topically administering to the skin of the selected or identified subject the mixture, which comprises the ethoxylated oil and water from a reservoir. The reservoir of water can be any body of water as can be found in a container, a mixing vessel, a mixing tank, or a mixing kettle. In some alternatives, the reservoir of water can be a water softener system, a water purification system, or a water filtration system. In some alternatives, the reservoir of water can be a drinking water system or a drinking fountain. In some alternatives, other suitable reservoirs of water can include but are not limited to a swimming pool, a pool, a whirlpool, a steam room, a sauna, a storage tank, a sink, a bath, a tub, or a shower.

One skilled in the art will immediately appreciate that the ethoxylated oil can be added to stagnant, sprayed or flowing water to create the mixture. Accordingly, in some alternatives of the methods described herein, the ethoxylated oil is contacted with a stagnant body of water and mixed so as to form a stagnant mixture. In some alternatives, the ethoxylated oil is metered in-line, in real time, to sprayed or flowing water so as to form a sprayable or flowable mixture.

In some alternatives, the method for increasing conductance and capacitance of a subject's (e.g., a human or animal such as a domestic animal or farm animal such as dog, cat, horse, cattle, pig, or sheep) skin, and decreasing impedance of said subject skin, described herein, further comprise determining or measuring skin hydration or moisturization of the subject after administration of the mixture. One skilled in the art will readily appreciate that improvements in skin hydration or moisturization can be measured using known systems and techniques, including a number of methods and instruments that have been developed for studying skin physiology, biophysical properties, and function of the skin barrier. Generally, skin hydration or moisturization values can be determined by using any suitable techniques known in the art and can be determined by, for example, techniques developed for assessing skin hydration or moisturization based on one or more electrical properties of the skin such as measurement of resistance, alternating current conductivity (conductance), capacitance, and impedance of the skin surface. For example, one skilled in the art will readily appreciate that skin hydration or moisturization can be determined by measuring electromagnetic radiation on the skin surface, or by determining changes in the dielectric constant or dielectric permittivity due to variation in skin surface hydration or moisturization. Other non-limiting examples of suitable techniques for measuring skin hydration or moisturization in accordance with the methods described herein include determination of skin hydration or moisturization through measurements of thermal conductivity, or assessment of the skin hydration or moisturization value based on at least one elastographic parameter of the skin.

The phrase "transepidermal water loss" (TEWL), as used herein, refers to water loss through the epidermis generally exacerbated by skin barrier damage caused by environmental factors associated with dry skin, such as detergents, soaps, solvents or ultraviolet light which tend to remove or damage the skin's protective lipids, resulting in such water loss. The measurement of TEWL is therefore important for evaluating the efficiency of the skin water barrier. Typically, this measurement can be performed using a Tewameter® device (Courage+Khazaka Electronic, Germany), and the measurement of the water evaporation is based on the diffusion principle in an open chamber.

In some alternatives, determining or measuring skin hydration or moisturization can be performed using Attenuated Total Reflectance/Fourier Transform Infrared (ATR/FTIR) Spectrophotometric analysis in which skin studies are conducted and analyzed based on the reflection of energy at the prism/skin interface. Generally, ATR/FTIR studies involve contact of the skin sample and prism. A hydration or moisturization procedure is employed in order to increase the softness and flexibility of the skin surface which results in a less variable contact between the skin and prism. Systems and procedures suitable for ATR/FTIR analysis of skin hydration or moisturization are known in the art.

In some alternatives, electrical conductance can be measured as an indicator of skin hydration or moisturization when a constant frequency alternating current is applied to skin. Skin hydration or moisture can then be calculated from the electric conductivity that is dependent on the water content of the skin (see Woo et al., Anal. Chem., 73, pp. 4964-4971, 2001). Conductance has been reported to correlate well with the superficial portion of the stratum corneum even when the electrical field on the stratum corneum is non-homologous. Skin conductance can be measured using equipment such as Skicon® 200 hygrometers.

Other equipment suitable for measuring skin surface capacitance as an indicator of skin hydration or moisturization, in accordance with some alternatives of the methods disclosed herein, may include a Corneometer® (Courage+Khazaka Electronic, Germany), ServoMed® evaporimeters, a Nova Dermal Phase Meter 9003, and a DermaLab®-Hydration Probe and Module (Cortex Technology, Denmark). Besides conventional corneometry, additional methods for measuring hydration or moisturization may include nuclear magnetic resonance (NMR) spectroscopy and transient thermal transfer (TTT).

In some alternatives, a Tewameter® device (Courage+Khazaka Electronic, Germany), a ServoMed® evaporimeter, or a DermaLab®-TEWL Probe and Module (Cortex Technology, Denmark) can be used to measure transepidermal water loss (TEWL) as an assessment of skin hydration or moisturization value. Increases in TEWL can be generally attributed to a breakdown in the barrier properties of the skin. Decreases in TEWL can be generally attributed to the associated improvement in barrier properties (see Morrison, J. Soc. Cosmet. Chem., 43, pp. 161-167, 1992).

Methods of Creating Mixtures for Improving Skin Hydration or Moisturization

In one aspect, some alternatives of the present disclosure relate to methods of making a mixture for improving hydration or moisturization of the skin of a subject, (e.g., a human or animal such as a domestic animal or farm animal such as dog, cat, horse, cattle, pig, or sheep) comprising of mixing water and an ethoxylated oil to generate a mixture or emulsion, then adding to said mixture or emulsion at least one additional component such as glycerin, urea, mineral oil, dimethicone, hyaluronic acid (sodium hyaluronate), γ-polyglutamic acid (or gamma-polyglutamic acid), betaine, sodium PCA, sodium-L-lactate, propanediol, isosorbide dicaprylate, C12-13 alkyl lactate, Di-C12-13 alkyl malate, PPG 15 Stearyl Ether, isostearyl isostearate, isopropyl isostearate, palmitamide MEA, *Helianthus annuus* (sunflower) seed oil unsaponifiables, *Brassica Campestris* (Rapeseed) Sterols, trehalose, hexylene glycol, pentylene glycol, polyquaternium-51, Triacetin, caprylyl glycol, *Argemone mexicana* callus extract, Tamarindus indica seed polysaccharide, oat beta glucan, pentaclethra macroloba oil (pracaxi oil), oenocarpus bataua oil (pataua oil), tetrahexyldecyl ascorbate, and/or ceramides (FIG. 1).

In some alternatives, the method for creating a mixture or emulsion for improving hydration or moisturization of the skin of the subject will have one or more components added after the water and ethoxylated oil are mixed, such as xanthan gum, zinc dioxide, titanium dioxide, talc, silica, and a combination of phenoxyethanol, caprylyl glycol, ethylhexylglycerin, and hexylene glycol, sold under the trade name Botanistat PF-64.

In some alternatives, the ethoxylated oil that can be used in the methods described herein can be a vegetable, plant, fruit, seed, marine, flower, nut, animal, or synthetic oil or fatty acid, fatty alcohol, or fatty amine therein having an average number of ethoxylations per molecule that is 10, 11, 12, 13, 14, 15, 16, 17, 18, or 19 or an average number of ethoxylations per molecule that is within a range defined by any two of the aforementioned values. In some alternatives, the ethoxylated oil can be unsaturated fatty acid. Preferable ethoxylated oils can be obtained or created from, for example, oleic acid, palmitoleic acid, apricot kernel oil, avocado oil, evening primrose oil, grape seed oil, hazelnut oil, pumpkinseed oil, rosehip oil, safflower oil, sunflower oil, walnut oil, wheat germ oil, neem oil, mink oil, lanolin, argan oil, Abyssinian oil, *Salvia Hispanica* oil (chia seed oil), Calophyllum Tacamahaca Seed oil (tamanu oil), squalane, sea buckthorn oil, meadowfoam oil, castor oil, jojoba oil, olive oil, corn oil, sesame oil, oenocarpus bataua oil, pentaclethra macroloba oil, or emu oil, or any combination thereof. In some alternatives, the ethoxylated oil that can be used in the methods described herein is obtained or created from macadamia nut oil. Preferably, the average number of ethoxylations per molecule in the ethoxylated macadamia nut oil is 10, 11, 12, 13, 14, 15, 16, 17, 18, or 19 or an average number of ethoxylations per molecule that is within a range defined by any two of the aforementioned values. In a particularly preferred alternative, the ethoxylated oil is obtained from macadamia nut oil with 16 ethoxylations per molecule. In some alternatives, the amount of ethoxylated macadamia nut oil in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts.

Depending on the intended applications, the amount of ethoxylated oil in the mixture suitable for the methods described herein can vary. For example, in some alternatives, the methods for creating a mixture for improving skin hydration or moisturization in the present disclosure can comprise a mixture comprising between 0.1% and 50% by weight or volume of ethoxylated oil(s). That is, some alternatives of the methods described herein can comprise a mixture containing less than or equal to (but not zero) 0.1%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, or 50.0% ethoxylated oil(s) by weight or volume or an amount within a range defined by any two of the aforementioned amounts. In some preferred alternatives, the amount of ethoxylated oil(s) in the mixture is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight or volume or an amount that is within a range defined by any two of the aforementioned amounts.

In some alternatives of the methods described herein, the mixture is formulated for topical administration. The terms "administration" and "administering", as used herein, refer to the delivery of a mixture by an administration route parenteral, intranasal, ocular, ear canal, sublingual, buccal, mucosal, and/or oral administration. The term "topical administration" is used herein in its conventional sense to refer to delivery of an active agent to a body surface, such as, the skin, as in, for example, topical administration of a drug in the prevention or treatment of various skin disorders, the application of cosmetics and cosmeceuticals, including moisturizers, face or body sprays, body washes, facial cleansers, lotions, masks, sunscreens, and the like. Topical administration, in contrast to transdermal administration, provides a local rather than a systemic effect. As such, "topical administration" as used herein is limited to a surface deposition of the mixture, and excludes transdermal systemic delivery. In some alternatives, the topical formulations described herein further comprise an essential oil, a makeup pigment, a tanning pigment, or a fragrance.

In some alternatives, the mixture formulated for topical administration contains drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and/or any mixtures thereof. In some alternatives, the mixture, which consists, consists essentially of, or comprises of drinking water, bottled water, sparkling water, sparkling mineral water, alkaline water, glacial water, coconut water, carbonated water, purified drinking water, natural water, spring water, natural spring water, artesian water, natural artesian water, mineral water or natural mineral water first contacted with ethoxylated oil, contains one or more of the following: Fiji® Water, Ice Mountain, Sparkletts, Zico, Vita Coco, Aquafina, Arrowhead Water, Dejà Blue, Crystal Geyser, Evian, Glacéau Smartwater, Glacéau Vitaminwater, Iceland Pure Spring Water, Nestlé® Pure Life®, Nestlé® Waters, Niagara, Poland Spring, Propel Fitness Water, San Pellegrino, Gerolsteiner, Ferrarelle, Perrier, Mountain Valley, Ty Nant, Volvic, Icelandic Glacial, Dasani, Deer Park, Ozarka, Voss, Vittel, Contrex, Acqua Panna, São Lourenço and Sierra Springs water and/or any mixtures thereof.

All publications and patent applications mentioned in this specification are herein incorporated by reference to the same extent as if each individual publication or patent application was specifically and individually indicated to be incorporated by reference.

No admission is made that any reference cited herein constitutes prior art. The discussion of the references states what their authors assert, and the applicants reserve the right to challenge the accuracy and pertinence of the cited documents. It will be clearly understood that, although a number of information sources, including scientific journal articles, patent documents, and textbooks, are referred to herein, this reference does not constitute an admission that any of these documents forms part of the common general knowledge in the art.

The discussion of the general methods given herein is intended for illustrative purposes only. Other alternative methods and embodiments will be apparent to those skilled in the art upon review of this disclosure.

EXAMPLES

The present disclosure generally relates to methods and compositions for improving hydration or moisturization of the skin. In particular, the disclosure provides methods for enhancing hydration or moisturization of the skin of a subject (e.g., a human or animal such as a domestic animal or farm animal such as dog, cat, horse, cattle, pig, or sheep), by topically administering to the skin a mixture comprising or consisting of an ethoxylated oil and water or a micro or nano emulsion and water. Also provided are methods for preparing bodies of water containing an ethoxylated oil or a micro or nano emulsion for enhancing skin hydration or moisturization of a subject. Further provided are methods for making micro or nano emulsions that comprise a non-ethoxylated macadamia nut oil or a ethoxylated macadamia nut oil and water. Additionally the disclosure provides methods for enhancing hydration or moisturization of the skin of a subject (e.g., a human or animal such as a domestic animal or farm animal such as dog, cat, horse, cattle, pig, or sheep) by topically administering to the skin of a selected or identified subject a mixture, which comprises, consists essentially of, or consists of water contacted with an ethoxylated oil or a micro or nano emulsion prior to inclusion of an additional component or compound into the mixture. Also provided are methods for increasing skin conductance and capacitance, and decreasing impedance by topically administering to the skin a mixture, which comprises or consists of water contacted with an ethoxylated oil or a micro or nano emulsion prior to introducing additional components or compounds to the mixture. Further provided are methods for making a mixture for hydrating or moisturizing skin comprising or consisting of water contacted with an ethoxylated oil or a micro or nano emulsion prior to introducing an additional component or compound to the mixture. In some alternatives, the mixture formulated for topical administration contains drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and/or any mixtures thereof. In some alternatives, the mixture, which consists, consists essentially of, or comprises of drinking water, bottled water, sparkling water, sparkling mineral water, alkaline water, glacial water, coconut water, carbonated water, purified drinking water, natural water, spring water, natural spring water, artesian water, natural artesian water, mineral water or natural mineral water first contacted with ethoxylated oil or a micro or nano emulsion, contains one or more of the following: Fiji® Water, Ice Mountain, Sparkletts, Zico, Vita Coco, Aquafina, Arrowhead Water, Dejà Blue, Crystal Geyser, Evian, Glacéau Smartwater, Glacéau Vitaminwater, Iceland Pure Spring Water, Nestlé® Pure Life®, Nestlé® Waters®, Niagara, Poland Spring, Propel Fitness Water, San Pellegrino, Gerolsteiner, Ferrarelle, Perrier, Mountain Valley, Ty Nant, Volvic, Icelandic Glacial, Dasani, Deer Park, Ozarka, Voss, Vittel, Contrex, Acqua Panna, São Lourenço and Sierra Springs water and/or any mixtures thereof.

Additional alternatives are disclosed in further detail in the following examples, which are not in any way intended to limit the scope of the claims.

Example 1

General Procedure for Human Clinical Trials

This Example describes a general procedure developed for the human clinical studies that were carried out to evaluate the mixtures described herein for their effectiveness in improving skin hydration or moisturization.

Changes in skin conductance, impedance or capacitance were used to study epidermal hydration in vivo. Measurements were made to determine the difference in dielectric constant of the skin. Typically, skin has a low dielectric constant, and water has a high dielectric constant of 81. When skin is hydrated, conductance and/or capacitance increases and/or impedance decreases. A Corneometer® CM 825 (Courage+Khazaka Electronic, Germany) was used to measure changes in the electrical capacitance of the test subject's skin which is reflective of the changes in hydration or moisturization level of the skin surface. The measurements were based on capacitance measurement of a dielectric medium. The measurement can detect small changes in the skin hydration or moisturization level. Three replicate measurements were taken at each treated site, the positive control site, and the placebo control site at each measurement interval.

The selected skin sites for testing were an area on the outer, lower legs.

Subjects reported to the facility at least 3 days prior to the start of the study. Enrolled subjects received a neutral soap bar (Neutrogena®) to use for cleansing (i.e. bathing) their lower legs for a 3-day washout period. Enrolled subjects were given specific instructions prohibiting use of all personal care products (e.g., lotions, creams, moisturizers, cleansers) on all of the test sites (e.g., the two lower legs) for the entire washout period and duration of study except for those products provided by trial personnel. Following the washout period, the subjects returned to the testing facility and were instructed to wear clothing that did not cover their lower legs on the evaluation day. The surface of the outer lower legs was gently wiped with a damp disposable washcloth and patted dry with a paper towel by trained trial personnel. Trained trial personnel marked 6 test sites on each subject based on a computer generated test site randomization code. This randomization code was based on the location of 6 possible test sites, specifically 3 sites per lower leg. Each test site was approximately 4 cm×4 cm. A schematic representation of test sites is shown at FIG. 2. Test sites were placed centrally on the outer lower legs (at least 2 cm from the knee and at least 2 cm from the ankle). Per randomization code, one site served as the placebo control site and one served as the positive control site. The four remaining sites tested four different experimental formulas, respectively. The placebo control was comprised solely of deionized water (or "DI Water"). The positive control used in this experiment was a serum finished formula containing over ten total ingredients or ingredient blends (hereinafter "HA Serum") that included 2.0% hyaluronic acid ("HA"), a common skin moisturizing ingredient well known by those skilled in the art. Prior to the base line (pre-treatment) measurement taken, the subjects remained seated for at least thirty (30) minutes in a room maintained at 20-24° C. and 30-50% relative humidity to equilibrate. During this time, the subjects were instructed to keep their lower legs uncovered/exposed.

Skin hydration or moisturization values were determined as follows.

The base line value (before applying control or non-control test products) was established by multiple readings (only one is needed although typically, several values were taken and averaging several measurements helped eliminate measurement error) of the skin hydration or moisturization in each of the six test sites. Trained clinical staff then applied 2 mg/cm$^2$ of test product to its designated test site, and rubbed it in until fully absorbed. To avoid cross contamination, such clinical staff personnel wore a fresh fingercot before and during each application and pipetted the test product directly onto the appropriate sites. The post-baseline (treatment) value was established by three readings of the skin's conductivity value in each of the six test sites at six separate time points. Changes in skin hydration or moisturization values were determined by subtracting the average baseline skin conductivity value measured prior to treatment from the average post-baseline (treatment) skin conductivity value measured at six separate time points. Hydration or moisturization values and percent changes could then be calculated.

Example 2

Clinical Evaluation of the Efficacy of Test Product 1 Mixture Containing 1% PEG-16 Macadamia Glycerides and Water Clinical studies were conducted according to the general procedure described in Example 1 herein above. Under conditions of the study, a total of 15 healthy female subjects, 35-65 years of age, completed the clinical study evaluating the efficacy of a mixture containing 1% PEG-16 Macadamia Glycerides oil and deionized water (or "DI Water"). A summary of key clinical findings is shown in Table 1.

TABLE 1

Average post-treatment differences in skin hydration or moisturization relative to the average baseline value - Positive differences indicate increases in skin hydration/moisturization.

| Parameter | 15 Minute | 30 Minute | 1 Hour | 2 Hour | 3 Hour | 8 Hour |
|---|---|---|---|---|---|---|
| Mean % Difference from Baseline (Placebo Control Site) | 1.08% | −0.05% | −0.64% | 0.19% | −0.58% | −0.27% |
| % of Subjects Improved (Placebo Control Site) | 66.67% | 60.00% | 40.00% | 46.67% | 20.00% | 40.00% |
| Mean % Difference from Baseline (Positive Control) | 102.44% | 76.41% | 54.61% | 37.56% | 28.04% | 23.72% |
| % of Subjects Improved (Positive Control) | 100.00% | 100.00% | 100.00% | 100.00% | 100.00% | 93.33% |

TABLE 1-continued

Average post-treatment differences in skin hydration or moisturization relative to the average baseline value - Positive differences indicate increases in skin hydration/moisturization.

| Parameter | 15 Minute | 30 Minute | 1 Hour | 2 Hour | 3 Hour | 8 Hour |
|---|---|---|---|---|---|---|
| Mean % Difference from Baseline (Test Product 1) | 39.53% | 30.15% | 24.74% | 20.21% | 16.57% | 12.84% |
| % of Subjects Improved (Test Product 1) | 100.00% | 100.00% | 100.00% | 100.00% | 86.67% | 66.67% |

Clinical Findings:

As shown in Table 1, there was an improvement in skin hydration/moisturization for Test Product 1 (defined as 1% PEG-16 Macadamia Glycerides and DI Water) after a single application to treated subject's skin at the 15 minute, 30 minute, 1 hour, 2 hour, 3 hour, and 8 hour post-treatment intervals, when compared to the average baseline value. In particular, a 39.53%, 30.15%, 24.74%, 20.21%, 16.57% and 12.84% increase in skin hydration/moisturization was observed, on average, in treated subjects at the 15-min, 30-min, 1-hr, 2-hr, 3-hr, and 8-hr time points, respectively.

A number of subjects demonstrated improvement in skin hydration/moisturization for the Test Product 1 site at the 15 minute, 30 minute, 1 hour, 2 hour, and 3 hour post-treatment intervals. In particular, 100% of the treated subjects displayed an improvement in skin hydration/moisturization at the 15-min, 30-min, 1-hr and 2-hr time points.

Compared to the baseline, there was an improvement in skin hydration/moisturization for Test Product 1 at the 15 minute, 30 minute, 1 hour, 2 hour, 3 hour, and 8 hour post-treatment intervals.

A number of subjects demonstrated improvement in skin hydration/moisturization for Test Product 1 at the 15 minute, 30 minute, 1 hour, 2 hour, and 3 hour post-treatment intervals.

TABLE 2

Post-treatment differences in skin hydration/moisturization relative to Test Product 1 versus DI Water only (Placebo Control site)-Positive differences indicate that the treatment site (for Test Product 1) was more hydrated/moisturized than the Placebo Control (DI Water only) site.

| Comparison (%ΔTest Product 1 - %ΔPlacebo Control) | Interval | Variation Mean % |
|---|---|---|
| Test Product 1 - Placebo Control | 15 Minute | 38.45% |
| Test Product 1 - Placebo Control | 30 Minute | 30.19% |
| Test Product 1 - Placebo Control | 1 Hour | 25.39% |
| Test Product 1 - Placebo Control | 2 Hour | 20.02% |
| Test Product 1 - Placebo Control | 3 Hour | 17.15% |
| Test Product 1 - Placebo Control | 8 Hour | 13.11% |

Clinical Findings: As shown in Table 2, the treatment site for Test Product 1 (again, defined as 1% PEG-16 Macadamia Glycerides and DI Water) was more hydrated/moisturized than the Placebo Control site (DI Water only) when the percent average change in the control site value is subtracted from the percent average change in the treatment site (treated by Test Product 1) value at the 15 minute, 30 minute, 1 hour, 2 hour, 3 hour, and 8 hour post-treatment intervals.

Example 3

Clinical Evaluation of the Efficacy of Test Product 2 Mixture Containing 2% PEG-16 Macadamia Glycerides and Water Clinical studies were conducted according to the general procedure described in Example 1 herein above. Under conditions of the study, a total of 15 healthy female subjects, 35-65 years of age, completed the clinical study evaluating the efficacy of a mixture containing 2% PEG-16 Macadamia Glycerides oil and DI Water. A summary of key clinical findings is shown in Table 3.

TABLE 3

Average post-treatment differences in skin hydration or moisturization relative to the average baseline value - Positive differences indicate increases in skin hydration/moisturization.

| Parameter | 15 Minute | 30 Minute | 1 Hour | 2 Hour | 3 Hour | 8 Hour |
|---|---|---|---|---|---|---|
| Mean % Difference from Baseline (Placebo Control Site) | 1.08% | −0.05% | −0.64% | 0.19% | −0.58% | −0.27% |
| % of Subjects Improved (Placebo Control Site) | 66.67% | 60.00% | 40.00% | 46.67% | 20.00% | 40.00% |
| Mean % Difference from Baseline (Positive Control) | 102.44% | 76.41% | 54.61% | 37.56% | 28.04% | 23.72% |
| % of Subjects Improved (Positive Control) | 100.00% | 100.00% | 100.00% | 100.00% | 100.00% | 93.33% |
| Mean % Difference from Baseline (Test Product 2) | 36.00% | 29.52% | 26.94% | 22.15% | 17.73% | 12.75% |
| % of Subjects Improved (Test Product 2) | 100.00% | 100.00% | 100.00% | 100.00% | 86.67% | 86.67% |

Clinical Findings:

As shown in Table 3, there was an improvement in skin hydration/moisturization for Test Product 2 (defined as 2% PEG-16 Macadamia Glycerides and DI Water) after a single application to treated subject's skin at the 15 minute, 30 minute, 1 hour, 2 hour, 3 hour, and 8 hour post-treatment intervals, when compared to the average baseline value. In particular, a 36.00%, 29.52%, 26.94%, 22.15%, 17.73% and 12.75% increase in skin hydration/moisturization was observed, on average, in treated subjects at the 15-min, 30-min, 1-hr, 2-hr, 3-hr, and 8-hr time points, respectively.

A number of subjects demonstrated improvement in skin hydration/moisturization for the Test Product 2 site at the 15 minute, 30 minute, 1 hour, 2 hour, 3 hour, and 8 hour post-treatment intervals. In particular, 100% of the treated subjects displayed an improvement in skin hydration/moisturization at the 15-min, 30-min, 1-hr, and 2-hr time points.

Compared to the baseline, there was an improvement in skin hydration/moisturization for Test Product 2 at all time points, i.e. at the 15 minute, 30 minute, 1 hour, 2 hour, 3 hour, and 8 hour post-treatment intervals.

A number of subjects demonstrated improvement in skin hydration/moisturization for Test Product 2 at the 15 minute, 30 minute, 1 hour, 2 hour, 3 hour, and 8 hour post-treatment intervals.

TABLE 4

Post-treatment differences in skin hydration/moisturization relative to Test Product 2 versus DI Water only (Placebo Control site)-Positive differences indicate that the treatment site (for Test Product 2) was more hydrated/moisturized than the Placebo Control (DI Water only) site.

| Comparison (%ΔTest Product 2 - %ΔPlacebo Control) | Interval | Variation Mean % |
|---|---|---|
| Test Product 2 - Placebo Control | 15 Minute | 34.92% |
| Test Product 2 - Placebo Control | 30 Minute | 29.56% |
| Test Product 2 - Placebo Control | 1 Hour | 27.58% |
| Test Product 2 - Placebo Control | 2 Hour | 21.96% |
| Test Product 2 - Placebo Control | 3 Hour | 18.30% |
| Test Product 2 - Placebo Control | 8 Hour | 13.02% |

Clinical Findings:

As shown in Table 4, the treatment site for Test Product 2 (again, defined as 2% PEG-16 Macadamia Glycerides and DI Water) was more hydrated/moisturized than the Placebo Control site (DI Water only) when the percent average change in the control site value is subtracted from the percent average change in the treatment site (treated by Test Product 2) value at the 15 minute, 30 minute, 1 hour, 2 hour, 3 hour, and 8 hour post-treatment intervals.

Example 4

Clinical Evaluation of the Efficacy of Test Product 3 Mixture Containing 4% PEG-16 Macadamia Glycerides and Water Clinical studies were conducted according to the general procedure described in Example 1 herein above. Under conditions of the study, a total of 15 healthy female subjects, 35-65 years of age, completed the clinical study evaluating the efficacy of a mixture containing 4% PEG-16 Macadamia Glycerides oil and DI Water. A summary of key clinical findings is shown in Table 5.

TABLE 5

Average post-treatment differences in skin hydration or moisturization relative to the average baseline value - Positive differences indicate increases in skin hydration/moisturization.

| Parameter | 15 Minute | 30 Minute | 1 Hour | 2 Hour | 3 Hour | 8 Hour |
|---|---|---|---|---|---|---|
| Mean % Difference from Baseline (Placebo Control Site) | 1.08% | −0.05% | −0.64% | 0.19% | −0.58% | −0.27% |
| % of Subjects Improved (Placebo Control Site) | 66.67% | 60.00% | 40.00% | 46.67% | 20.00% | 40.00% |
| Mean % Difference from Baseline (Positive Control) | 102.44% | 76.41% | 54.61% | 37.56% | 28.04% | 23.72% |
| % of Subjects Improved (Positive Control) | 100.00% | 100.00% | 100.00% | 100.00% | 100.00% | 93.33% |
| Mean % Difference from Baseline (Test Product 3) | 44.70% | 31.91% | 28.59% | 21.52% | 17.35% | 10.58% |
| % of Subjects Improved (Test Product 3) | 100.00% | 100.00% | 100.00% | 93.33% | 80.00% | 73.33% |

Clinical Findings:

As shown in Table 5, there was an improvement in skin hydration/moisturization for Test Product 3 (defined as 4% PEG-16 Macadamia Glycerides and DI Water) after a single application to treated subject's skin at the 15 minute, 30 minute, 1 hour, 2 hour, 3 hour, and 8 hour post-treatment intervals, when compared to the average baseline value. In particular, a 44.70%, 31.91%, 28.59%, 21.52%, 17.35% and 10.58% increase in skin hydration/moisturization was observed, on average, in treated subjects at the 15-min, 30-min, 1-hr, 2-hr, 3-hr, and 8-hr time points, respectively.

A number of subjects demonstrated improvement in skin hydration/moisturization for the Test Product 3 site at the 15 minute, 30 minute, 1 hour, and 2 hour post-treatment intervals. In particular, at least 93.33% of the treated subjects displayed an improvement in skin hydration/moisturization at 15-min, 30-min, 1-hr, and 2-hr time points.

Compared to the baseline, there was an improvement in skin hydration/moisturization for Test Product 3 at all time points, i.e. at the 15 minute, 30 minute, 1 hour, 2 hour, 3 hour, and 8 hour post-treatment intervals.

TABLE 6

Post-treatment differences in skin hydration/moisturization relative to Test Product 3 versus DI Water only (Placebo Control site)-Positive differences indicate that the treatment site (for Test Product 3) was more hydrated/ moisturized than the Placebo Control (DI Water only) site.

| Comparison (%ΔTest Product 3 - %ΔPlacebo Control) | Interval | Variation Mean % |
|---|---|---|
| Test Product 3 - Placebo Control | 15 Minute | 43.62% |
| Test Product 3 - Placebo Control | 30 Minute | 31.95% |
| Test Product 3 - Placebo Control | 1 Hour | 29.23% |
| Test Product 3 - Placebo Control | 2 Hour | 21.32% |
| Test Product 3 - Placebo Control | 3 Hour | 17.92% |
| Test Product 3 - Placebo Control | 8 Hour | 10.84% |

Clinical Findings:

As shown in Table 6, the treatment site for Test Product 3 (again, defined as 4% PEG-16 Macadamia Glycerides and DI Water) was more hydrated/moisturized than the Placebo Control site (DI Water only) when the percent average change in the control site value is subtracted from the percent average change in the treatment site (treated by Test Product 3) value at the 15 minute, 30 minute, 1 hour, 2 hour, 3 hour, and 8 hour post-treatment intervals.

Example 5

Micelle Size Analysis

This Example describes an exemplary study carried out to characterize a number of oil-in-water (O/W) emulsions and water-in-oil (W/O) emulsions prepared in accordance with some alternatives of the micromixing methods disclosed herein. In this study, the micelle or particle size distribution is measured by dynamic light scattering (DLS) by using a Malvern Zetasizer instrument (Malvern, United Kingdom), where the distribution of diffusion coefficients is determined through the measurement and correlation of the statistical fluctuations in the light scattered from a system of particle diffusion under the influence of Brownian motion. In the emulsions, micelles move in a constant random Brownian motion such that they cause the intensity of scattered light to fluctuate as a function of time. Therefore, in these experiments, micelles' or particles' sizes are measured based on the correlation function as established by the dispersion technology software (DTS) using various algorithms.

All measurements described in this Example are performed at 25° C. with a Zetasizer apparatus which is equipped with a 4-milliwatt Helium/Neon "red" laser at a wavelength of 633 nanometer, a measurement cell, a photomultiplier, and a correlator. A series of dilutions of each emulsion sample is prepared with distilled or deionized water (1:2; 1:5; 1:50; 1:200; and 1:400), and placed in vertical cylindrical cuvettes (DTS0012; Sarstedt AG&Co, Nübrecht, Germany). The cuvettes are then capped and shaken by hand until the sample is dispersed evenly in the cuvette without air bubbles. Using an avalanche of photodiode detector set at 25° C., the scattering intensity is measured at a 173° angle relative to the source. Intensity autocorrelation functions are analyzed by a General Purpose Algorithm (integrated into the Malvern Zetasizer software) in order to determine the distribution of the translational z-averaged diffusion coefficient of the particles, i.e. $D_T$ ($m^2 s^{-1}$). The $D_T$ parameter and the hydrodynamic radius ($R_h$) of particles are related through the Stokes-Einstein equation: $D_T = k_B T/6\pi\eta R_h$. The refractive index (RI) and absorbance level are set respectively at 1.471 and 0.01 at 25° C. Measurements are repeated at least three times and the average diameter of the micelles or particles can be calculated.

Example 6

General Procedure for Human Clinical Studies

This Example describes a general procedure developed for the human clinical studies that were carried out to evaluate the mixtures described herein for their effectiveness in improving skin hydration or moisturization.

Changes in skin conductance, impedance or capacitance were used to study epidermal hydration in vivo. Measurements were made to determine the difference in dielectric constant of the skin. Typically, skin has a low dielectric constant, and water has a high dielectric constant of 81. When skin is hydrated, conductance and/or capacitance increases and/or impedance decreases. A Corneometer® CM 825 (Courage+Khazaka Electronic, Germany) was used to measure changes in the electrical capacitance of the skin, which is reflective of the changes in hydration or moisturization level of the skin surface. The measurements were based on the capacitance measurement of a dielectric medium. The measurement could detect small changes in the skin hydration or moisturization level. Three replicate measurements were taken at each of the three experimental formula sites, the positive control site, and both placebo control sites at each measurement interval.

The selected skin sites for testing were an area on the outer, lower legs.

Subjects reported to the facility at least 3 days prior to the start of the study. Enrolled subjects received a neutral soap bar (Neutrogena®) to use for cleansing (i.e. bathing) their lower legs for a 3-day washout period. Enrolled subjects were given specific instructions prohibiting use of all personal care products (e.g., lotions, creams, moisturizers, cleansers) on all of the test sites (e.g., the two lower legs) for the entire washout period and duration of the study except for those products provided by the testing site personnel. Following the washout period, the subjects returned to the testing facility and were instructed to wear clothing that did not cover their lower legs on the evaluation day. The surface of the outer lower legs was gently wiped with a damp disposable washcloth and patted dry with a paper towel by trained testing site personnel. Trained testing site personnel marked 6 test sites on each subject based on a computer generated test site randomization code. This randomization code was based on the location of 6 possible test sites, specifically 3 sites per lower leg. Each test site was approximately 4 cm×4 cm. A schematic representation of test sites is shown at FIG. 3. Test sites were placed centrally on the outer lower legs (at least 2 cm from the knee and at least 2 cm from the ankle). Per randomization code, one site served as a first placebo control, one site served as the positive control, and one site served as a second placebo control. The three remaining sites tested three different experimental formulas, respectively. The first placebo control was comprised solely of DI water. The positive control used in this experiment was Test Product 2 (see Example 3, herein above), which is a mixture containing DI water and 2.0% PEG-16 Macadamia Glycerides. A second placebo control used in this experiment was a mixture containing DI water and 6 additional components, without an ethoxylated oil. Prior to the base line (pre-treatment) measurement taken, the subjects remained seated for at least thirty (30) minutes in a room maintained at 20-24° C. and 30-50% relative humidity to equilibrate. During this time, the subjects were instructed to keep their lower legs uncovered/exposed.

Skin hydration or moisturization values were determined as follows. The base line value (before applying control or non-control test products) was established by multiple readings (only one is needed although typically, several values were taken and averaging several measurements helped eliminate measurement error) of the skin hydration or moisturization in each of the six test sites. Trained clinical staff then applied approximately 2 mg/cm$^2$ of test product to its designated test site, and rubbed it in until fully absorbed. To avoid cross contamination, clinical staff personnel wore a fresh fingercot before and during each application and pipetted the test product directly onto the appropriate sites. The post-baseline (treatment) value was established by three readings of the skin's conductivity value in each of the six test sites at six separate time points. Changes in skin hydration or moisturization values were determined by subtracting the average baseline skin conductivity value measured prior to treatment from the average post-baseline (treatment) skin conductivity value measured at the six separate time points. Hydration or moisturization values and percent changes were then calculated.

Example 7

Clinical Evaluation of the Efficacy of Test Product 4 Containing 100% PEG-16 Macadamia Glycerides Clinical studies were conducted according to the general procedure described in Example 6 herein above. Under conditions of the study, a total of 18 healthy female subjects, 35-65 years of age, completed the clinical study evaluating the efficacy of only PEG-16 Macadamia Glycerides. An explanation of the contents of the mixtures used in this Example is shown in Table 7. A summary of key clinical findings is shown in Table 8.

TABLE 7

Experimental mixture contents.

| Mixture Type | Contents |
| --- | --- |
| Placebo Control | 100% DI water |
| Positive Control (or Test Product 2) | 98.0% DI water and 2.0% PEG-16 Macadamia Glycerides |
| Test Product 4 | 100% PEG-16 Macadamia Glycerides |

TABLE 8

Average post-treatment differences in skin hydration or moisturization relative to the average baseline value. Positive differences indicate increases in skin hydration/moisturization.

| Parameter | 15 Minute | 30 Minute | 1 Hour | 2 Hour | 3 Hour | 8 Hour |
| --- | --- | --- | --- | --- | --- | --- |
| Mean % Difference from Baseline (Placebo Control Site) | 9.73% | 4.74% | −1.19% | −3.00% | −0.28% | 0.19% |
| % of Subjects Improved (Placebo Control Site) | 83.33% | 72.22% | 27.78% | 33.33% | 38.89% | 38.89% |
| Mean % Difference from Baseline (Positive Control/Test Product 2) | 29.70% | 38.54% | 27.77% | 25.51% | 33.68% | 41.15% |
| % of Subjects Improved (Positive Control/Test Product 2) | 94.44% | 88.89% | 88.89% | 83.33% | 88.89% | 94.44% |
| Mean % Difference from Baseline (Test Product 4) | 91.04% | 107.17% | 116.80% | 124.10% | 131.67% | 137.27% |
| % of Subjects Improved (Test Product 4) | 100.00% | 100.00% | 100.00% | 100.00% | 100.00% | 100.00% |

Clinical Findings:

As shown in Table 8, there was an improvement in skin hydration/moisturization for Test Product 4 (defined as solely PEG-16 Macadamia Glycerides) after a single application to treated subject's skin at the 15 minute, 30 minute, 1 hour, 2 hour, 3 hour, and 8 hour post-treatment intervals, when compared to the average baseline value. In particular, a 91.04%, 107.17%, 116.80%, 124.10%, 131.67% and 137.27% increase in skin hydration/moisturization was observed, on average, in treated subjects at the 15-min, 30-min, 1-hr, 2-hr, 3-hr, and 8-hr time points, respectively.

All subjects demonstrated improvement in skin hydration/moisturization for the Test Product 4 site at the 15 minute, 30 minute, 1 hour, 2 hour, 3 hour, and 8 hour post-treatment intervals. In particular, 100% of the treated subjects displayed an improvement in skin hydration/moisturization at 15-min, 30-min, 1-hr, 2-hr, 3-hr, and 8-hr post-treatment intervals, respectively. Thus, Test Product 4 demonstrates that PEG-16 Macadamia Glycerides provide noticeable high two-digit and three-digit skin hydration/moisturization values.

As further shown in Table 8, there was also an improvement in skin hydration/moisturization for the Positive Control or Test Product 2 (defined as 2.0% PEG-16 Macadamia Glycerides and DI water) after a single application to treated subject's skin at the 15 minute, 30 minute, 1 hour, 2 hour, 3 hour, and 8 hour post-treatment intervals, when compared to the average baseline value. In particular, a 29.70%, 38.54%, 27.77%, 25.51%, 33.68% and 41.15% increase in skin hydration/moisturization was observed, on average, in treated subjects at the 15-min, 30-min, 1-hr, 2-hr, 3-hr, and 8-hr time points, respectively.

A number of subjects demonstrated improvement in skin hydration for the Positive Control or Test Product 2 site at the 15 minute, 30 minute, 1 hour, 2 hour, 3 hour, and 8 hour post-treatment intervals. In particular, 94.44%, 88.89%, 88.89%, 83.33%, 88.89%, and 94.44% of the treated subjects displayed an improvement in skin hydration/moisturization at the 15-min, 30-min, 1-hr, 2-hr, 3-hr, and 8-hr post treatment intervals, respectively.

These results demonstrate that mixtures containing PEG-16 Macadamia Glycerides hydrate/moisturize the skin, and are more effective at hydrating or moisturizing the skin than DI water alone.

TABLE 9

Post-treatment differences in skin hydration/moisturization relative to Test Product 4 (PEG-16 *Macadamia* Glycerides only) versus Placebo Control (DI water only). A positive difference indicates that the Test Product 4 site was more hydrated/moisturized than the Placebo Control site.

| Comparison (%ΔTest Product 4 - %ΔPlacebo Control) | Interval | Variation Mean % |
|---|---|---|
| Test Product 4 - Placebo Control | 15 Minute | 81.31% |
| Test Product 4 - Placebo Control | 30 Minute | 102.43% |
| Test Product 4 - Placebo Control | 1 Hour | 117.99% |
| Test Product 4 - Placebo Control | 2 Hour | 127.10% |
| Test Product 4 - Placebo Control | 3 Hour | 131.94% |
| Test Product 4 - Placebo Control | 8 Hour | 137.08% |

Clinical Findings:

As shown in Table 9, the treatment site for Test Product 4 (again, comprised solely of PEG-16 Macadamia Glycerides) was more hydrated/moisturized than the Placebo Control site (DI water only) when the percent average change in the Placebo Control site value is subtracted from the percent average change in the Test Product 4 site value at the 15 minute, 30 minute, 1 hour, 2 hour, 3 hour, and 8 hour post-treatment intervals. This demonstrates that PEG-16 Macadamia Glycerides only hydrates/moisturizes skin more effectively than DI water alone.

Conclusion:

This Example 7 thus provides evidence that PEG-16 Macadamia Glycerides only hydrates/moisturizes the skin more effectively than DI water alone. Example 7 also shows that a mixture of DI water and PEG-16 Macadamia Glycerides hydrates/moisturizes the skin more effectively than DI water alone.

Example 8

Clinical Evaluation of the Efficacy of Test Product 5 Containing DI Water Contacted with PEG-16 Macadamia Glycerides Prior to Contact with Additional Components or Compounds Clinical studies were conducted according to the general procedure described in Example 6 herein above. Under conditions of the study, a total of 18 healthy female subjects, 35-65 years of age, completed the clinical study evaluating the efficacy of an experimental formula containing DI water contacted first with PEG-16 Macadamia Glycerides and then combined with additional components or compounds. An explanation of the contents of the relevant formulas tested in Example 8 is shown in Table 10 and Table 11. A comparison between Test Product 5 site and Placebo Control 5 site with respect to percent change difference in mean hydration/moisturization measurements is shown in Table 12.

TABLE 10

Experimental mixture contents.

| Mixture Type | Contents |
|---|---|
| Test Product 5 | DI water contacted with PEG-16 *Macadamia* Glycerides, then combined with additional components*. Final PEG-16 *Macadamia* Glyceride concentration in finished experimental mixture: 2.0% (w/w). |
| Placebo Control 5 | DI water combined with additional components** (contained no PEG-16 *Macadamia* Glycerides) |

*See Table 11 for a complete list of additional components.
**Note: Additional components used in Test Product 5 are identical in type and amount to additional components used in Placebo Control 5.

TABLE 11

Additional components contained in Test Product 5 and Placebo Control 5.

| No. | INCI Name | Trade Name | % Weight |
|---|---|---|---|
| 1 | Xanthan Gum | Keltrol CG | 1.0% |
| 2 | Zinc Oxide | Zinc Oxide, USP | 2.0% |
| 3 | Titanium Dioxide | Titanium Dioxide, USP | 2.0% |
| 4 | Talc | Talcron MP 60-30, USP | 2.0% |
| 5 | Silica | Silisphere 10M | 2.0% |
| 6 | Phenoxyethanol & Caprylyl Glycol & Ethylhexylglycerin & Hexylene Glycol | Botanistat PF-64 | 0.5% |

INCI = International Nomenclature of Cosmetic Ingredients

TABLE 12

Post-treatment differences in skin hydration/moisturization relative to Test Product 5 (DI water contacted first with PEG-16 *Macadamia* Glycerides, then combined with additional components) versus Placebo Control 5 (DI water and the same additional components with no PEG-16 *Macadamia* Glycerides). A positive difference indicates that the Test Product 5 site was more hydrated/moisturized than the Placebo Control 5 site.

| Comparison (%ΔTest Product 5 - %ΔPlacebo Control 5) | Interval | Variation Mean % |
|---|---|---|
| Test Product 5 - Placebo Control 5 | 15 Minute | 10.12% |
| Test Product 5 - Placebo Control 5 | 30 Minute | 14.46% |
| Test Product 5 - Placebo Control 5 | 1 Hour | 8.99% |
| Test Product 5 - Placebo Control 5 | 2 Hour | 12.57% |
| Test Product 5 - Placebo Control 5 | 3 Hour | 14.22% |
| Test Product 5 - Placebo Control 5 | 8 Hour | 12.47% |

Clinical Findings:

As shown in Table 12, the treatment site for Test Product 5 (again, DI water contacted first with PEG-16 Macadamia Glycerides, then combined with additional components) was double-digit more hydrated/moisturized than the Placebo Control 5 site (DI water with the same additional components, but no PEG-16 Macadamia Glycerides) at five post-treatment intervals (e.g., at the 15-min, 30-min, 2-hr, 3-hr, and 8-hr time points, respectively), and single-digit more hydrated/moisturized than the Placebo Control 5 site at the remaining post-treatment interval (e.g., at the 1-hr time point) when the percent average change in the Placebo Control 5 site value is subtracted from the percent average change in the Test Product 5 site value at the 15 minute, 30 minute, 1 hour, 2 hour, 3 hour, and 8 hour post-treatment intervals.

Conclusion:

This Example 8 thus provides strong evidence that DI water contacted first with PEG-16 Macadamia Glycerides before introducing additional components hydrates/moisturizes the skin more effectively than DI water and the same additional components used at the same concentrations with no PEG-16 Macadamia Glycerides.

Example 9

Clinical Evaluation of the Efficacy of Test Product 6 Containing DI Water Contacted with Additional Components or Compounds, with PEG-16 Macadamia Glycerides Introduced at the End of the Manufacturing Process Clinical studies were conducted according to the general procedure described in Example 6 herein above. Under conditions of the study, a total of 18 healthy female subjects, 35-65 years of age, completed the clinical study evaluating the efficacy of an experimental formula containing DI water contacted first with additional components or compounds and then combined with PEG-16 Macadamia Glycerides added at the end of the manufacturing process. An explanation of the contents of the relevant formulas tested in Example 9 is shown in Table 13 and Table 14. A comparison between Test Product 6 site and Placebo Control 5 site with respect to percent change difference in mean hydration/moisturization measurements is shown in Table 15.

TABLE 13

Experimental mixture contents.

| Mixture Type | Contents |
| --- | --- |
| Test Product 6 | DI water contacted with additional components*, then combined with PEG-16 Macadamia Glycerides at the end of the manufacturing process. Final PEG-16 Macadamia Glyceride concentration in finished experimental mixture: 2.0% (w/w). |
| Placebo Control 5** | DI water contacted with additional components*** (contained no PEG-16 Macadamia Glycerides) |

*See Table 14 for a complete list of additional components.
**Note: Placebo Control 5 is identical in composition to Placebo Control 5 designated in Example 8.
***Note: Additional components used in Test Product 6 are identical in type and amount to additional components used in Placebo Control 5.

TABLE 14

Additional components contained in Test Product 6 and Placebo Control 5.

| No. | INCI Name | Trade Name | % Weight |
| --- | --- | --- | --- |
| 1 | Xanthan Gum | Keltrol CG | 1.0% |
| 2 | Zinc Oxide | Zinc Oxide, USP | 2.0% |
| 3 | Titanium Dioxide | Titanium Dioxide, USP | 2.0% |
| 4 | Talc | Talcron MP 60-30, USP | 2.0% |
| 5 | Silica | Silisphere 10M | 2.0% |
| 6 | Phenoxyethanol & Caprylyl Glycol & Ethylhexylglycerin & Hexylene Glycol | Botanistat PF-64 | 0.5% |

INCI = International Nomenclature of Cosmetic Ingredients

TABLE 15

Post-treatment differences in skin hydration/moisturization relative to Test Product 6 (DI water contacted first with additional components, then combined with PEG-16 Macadamia Glycerides at the end of the manufacturing process) versus Placebo Control 5 (DI water and the same additional components with no PEG-16 Macadamia Glycerides). A positive difference indicates that the Test Product 6 site was more hydrated/moisturized than the Placebo Control 5 site.

| Comparison (%ΔTest Product 6-%ΔPlacebo Control 5) | Interval | Variation Mean % |
| --- | --- | --- |
| Test Product 6-Placebo Control 5 | 15 Minute | 1.75% |
| Test Product 6-Placebo Control 5 | 30 Minute | 8.30% |
| Test Product 6-Placebo Control 5 | 1 Hour | 2.92% |
| Test Product 6-Placebo Control 5 | 2 Hour | 0.53% |
| Test Product 6-Placebo Control 5 | 3 Hour | 2.08% |
| Test Product 6-Placebo Control 5 | 8 Hour | −0.43% |

Clinical Findings:

As shown in Table 15, there was no double-digit increase in skin hydration/moisturization when comparing the Test Product 6 site and the Placebo Control 5 site at any post-treatment intervals (e.g., at the 15-min, 30-min, 1-hr, 2-hr, 3-hr, and 8-hr time points, respectively). Rather, a single-digit increase in skin hydration/moisturization was shown at four post-treatment intervals (e.g., at the 15-min, 30-min, 1-hr, and 3-hr time points, respectively), a fractional increase in skin hydration/moisturization was shown at one post-treatment interval (e.g., at the 2-hr time point), and an actual decrease in skin hydration/moisturization was shown at the remaining post-treatment interval (e.g., at the 8-hr time point) when comparing the Test Product 6 site and the Placebo Control 5 site.

Conclusion:

This Example 9 thus provides evidence that there is not a double-digit difference in hydration/moisturization between an experimental formula of DI water contacted first with additional components, and then combined with PEG-16 Macadamia Glycerides added at the end of the manufacturing process, and an experimental formula containing DI water and the same additional components used at the same concentrations, but without the presence of any PEG-16 Macadamia Glycerides. Thus, adding PEG-16 Macadamia Glycerides, a known and clinically proven hydrating/moisturizing ingredient (see Example 7, Table 8, Test Product 4), at the end of the manufacturing process provides mixed evidence (some increase, a fractional increase, and an actual decrease) in hydration/moisturization when comparing the Test Product 6 site and the Placebo Control 5 site at each of the six post-treatment intervals, respectively.

Example 10

Clinical Evaluation of the Efficacy of Test Product 5 Containing DI Water Contacted with PEG-16 Macadamia Glycerides Prior to Contact with Additional Components or Compounds, Compared to the Clinical Evaluation of the Efficacy of Test Product 6 Containing DI Water Contacted First with Additional Components or Compounds, with PEG-16 Macadamia Glycerides Introduced at the End of the Manufacturing Process Clinical studies were conducted according to the general procedure described in Example 6 herein above. Under conditions of the study, a total of 18 healthy female subjects, 35-65 years of age, completed the clinical study evaluating the comparative efficacy of two experimental formulas. The experimental formulas differed based on the order of addition of components that were added to the final experimental formulation. The first experimental formula (Test Product 5) contained DI water contacted first with PEG-16 Macadamia Glycerides and then combined with additional components added at the end of the manufacturing process. The second experimental formula (Test Product 6) contained DI water contacted first with the same additional components and then combined with PEG-16 Macadamia Glycerides added at the end of the manufacturing process. An explanation of the contents of the two experimental formulas, and each formula's respective manufacturing procedure, relevant to this Example 10 is shown in Table 16. A comparison between Test Product 5 site and Test Product 6 site with respect to percent change difference in mean hydration/moisturization measurements is shown in Table 17.

As shown in Table 16, Test Product 5 was manufactured in the exact order of the listed components. Notably, DI water contacted first with PEG-16 Macadamia Glycerides and then combined with the remaining six listed components in the order listed. Test Product 6 was manufactured in the exact order of the listed components. Notably and in contrast, DI water contacted first with the next six listed components in the order listed, and then combined with PEG-16 Macadamia Glycerides at the end of the manufacturing procedure.

TABLE 17

Post-treatment differences in skin hydration/moisturization relative to Test Product 5 (DI water contacted first with PEG-16/ *Macadamia* Glycerides, then combined with additional components) versus Test Product 6 (DI water contacted first with the same additional components, then combined with PEG-16 *Macadamia* Glycerides at the end of the manufacturing process). A positive difference indicates that the Test Product 5 site was more hydrated than the Test Product 6 site.

| Comparison (%ΔTest Product 5-%ΔTest Product 6) | Interval | Variation Mean % |
|---|---|---|
| Test Product 5-Test Product 6 | 15 Minute | 8.37% |
| Test Product 5-Test Product 6 | 30 Minute | 6.16% |
| Test Product 5-Test Product 6 | 1 Hour | 6.08% |
| Test Product 5-Test Product 6 | 2 Hour | 12.03% |
| Test Product 5-Test Product 6 | 3 Hour | 12.14% |
| Test Product 5-Test Product 6 | 8 Hour | 12.89% |

Clinical Findings:

As shown in Table 17, the treatment site for Test Product 5 was more hydrated/moisturized than the treatment site for Test Product 6, when the percent average change in the Test Product 6 site value is subtracted from the percent average change in the Test Product 5 site value at the 15 minute, 30 minute, 1 hour, 2 hour, 3 hour, and 8 hour post-treatment intervals.

TABLE 16

Experimental formulas contents and respective manufacturing procedure.

| | Experimental Formula Test Product 5 | | | Experimental Formula Test Product 6 | | |
|---|---|---|---|---|---|---|
| No. | INCI Name | Trade Name | % Weight | INCI Name | Trade Name | % Weight |
| 1 | Water | DI Water | QS | Water | DI Water | QS |
| 2 | PEG-16 *Macadamia* Glycerides | DermX ®-DD | 2.0% | Xanthan Gum | Keltrol CG | 1.0% |
| 3 | Xanthan Gum | Keltrol CG | 1.0% | Zinc Oxide | Zinc Oxide, USP | 2.0% |
| 4 | Zinc Oxide | Zinc Oxide, USP | 2.0% | Titanium Dioxide | Titanium Dioxide, USP | 2.0% |
| 5 | Titanium Dioxide | Titanium Dioxide, USP | 2.0% | Talc | Talcron MP 60-30, USP | 2.0% |
| 6 | Talc | Talcron MP 60-30, USP | 2.0% | Silica | Silisphere 10M | 2.0% |
| 7 | Silica | Silisphere 10M | 2.0% | Phenoxyethanol & Caprylyl Glycol & Ethylhexylglycerin & Hexylene Glycol | Botanistat PF-64 | 0.5% |
| 8 | Phenoxyethanol & Caprylyl Glycol & Ethylhexylglycerin & Hexylene Glycol | Botanistat PF-64 | 0.5% | PEG-16 *Macadamia* Glycerides | DermX ®-DD | 2.0% |

INCI = International Nomenclature of Cosmetic Ingredients
QS = Quantum Satis (or Quantity Sufficient)

Conclusion:

This Example 10 thus provides strong evidence that there is a difference in hydration/moisturization capabilities of an experimental formula of DI water contacted first with PEG- 16 Macadamia Glycerides and then combined with additional components, versus the hydration/moisturization capabilities of an experimental formula of DI water contacted first with the same additional components, and then combined with PEG-16 Macadamia Glycerides at the end of the manufacturing process. This is a surprising result since Example 7, Test Product 4 (100% PEG-16 Macadamia Glycerides) teaches that PEG-16 Macadamia Glycerides is a clinically proven hydrating/moisturizing ingredient at every tested time point on 100% of the subjects tested at every tested time point (see Table 8 for results). However and unexpectedly, order of addition matters: Test Product 5 has been shown to be, on average, more hydrating/moisturizing than Test Product 6 at a minimum of six different time points. Thus, this Example 10 demonstrates that an experimental formula of DI water contacted first with PEG-16 Macadamia Glycerides and then combined with additional components hydrates/moisturizes more effectively than an experimental formula of DI water contacted first with the same additional components, and then combined with PEG-16 Macadamia Glycerides at the end of the manufacturing process.

Example 11

General Procedure for Human Clinical Studies Involving Deionized Water (DI Water), Fiji® Natural Artesian (Bottled) Water, and Nestlé® "Pure Life"® Purified (Bottled) Water Mixed with and without PEG-16 Macadamia Glycerides This Example describes a general procedure developed for the human clinical studies that were carried out to evaluate the mixtures described herein for their effectiveness in improving skin hydration or moisturization.

Changes in skin conductance, impedance or capacitance were used to study epidermal hydration in vivo. Measurements were made to determine the difference in dielectric constant of the skin. Typically, skin has a low dielectric constant, and water has a high dielectric constant of 81. When skin is hydrated, conductance and/or capacitance increases and/or impedance decreases. A Corneometer® CM 825 (Courage+Khazaka Electronic, Germany) was used to measure changes in the electrical capacitance of the skin, which is reflective of the changes in hydration or moisturization level of the skin surface. The measurements were based on the capacitance measurement of a dielectric medium. The measurement could detect small changes in the skin hydration or moisturization level. Three replicate measurements were taken at each of the three experimental formula sites, and at each of the three placebo control sites at each measurement interval.

The selected skin sites for testing were areas on the outer, lower legs.

Subjects reported to the facility at least 3 days prior to the start of the study. Enrolled subjects received a neutral soap bar (Neutrogena®) to use for cleansing (i.e. bathing) their lower legs for a 3-day washout period. Enrolled subjects were given specific instructions prohibiting use of all personal care products (e.g., lotions, creams, moisturizers, cleansers) on all of the test sites (e.g., the two lower legs) for the entire washout period and duration of the study except for those products provided by the testing site personnel. Following the washout period, the subjects returned to the testing facility and were instructed to wear clothing that did not cover their lower legs on the evaluation day. The surface of the outer lower legs was gently wiped with a damp disposable washcloth and patted dry with a paper towel by trained testing site personnel. Trained testing site personnel marked 6 test sites on each subject based on a computer generated test site randomization code. This randomization code was based on the location of 6 possible test sites, specifically 3 sites per outer lower leg. Each test site was approximately 4 cm×4 cm. A schematic representation of test sites is shown at FIG. 4. Test sites were placed centrally on the outer lower legs (at least 2 cm from the knee and at least 2 cm from the ankle). Per randomization code, one site served as a placebo control for Test Product 7, one site served as a placebo control for Test Product 8, and one site served as a placebo control for Test Product 9. The three remaining sites tested three different experimental formulas, respectively. The placebo control for Test Product 7 was comprised solely of DI water. The placebo control for Test Product 8 was comprised solely of Nestlé® "Pure Life"® Purified (bottled) Water. The placebo control for Test Product 9 was comprised solely of Fiji® Natural Artesian (bottled) Water. Prior to the base line (pre-treatment) measurement taken, the subjects remained seated for at least thirty (30) minutes in a room maintained at 20-24° C. and 30-50% relative humidity to equilibrate. During this time, the subjects were instructed to keep their lower legs uncovered/exposed.

Skin hydration or moisturization values were determined as follows. The base line value (before applying control or non-control test products) was established in triplicate to establish the skin hydration or moisturization in each of the six test sites. The legs of each test subject were held in parallel to the ground throughout the duration of the treatment step. Each test site was first rinsed by a trained clinical staff member with 5 mls of DI water (only) using a 5 ml syringe to avoid one test product running off from one test site to another test site. Trained clinical staff then applied approximately 2 mg/cm$^2$ of each test product to its designated test site, and rubbed it in using both a clockwise and counterclockwise circular motion for 60.0 seconds. Then each test site was allowed to sit, untouched, for another 60.0 seconds. Each test site was then rinsed with 4.0 oz of DI water (only) and dabbed three times with a Kimwipes® wipe (Kimberly-Clark). Test subjects were then able to place their feet on the floor. To avoid cross contamination, a trained clinical staff member wore a fresh fingercot before and during each application and pipetted the test product directly onto the appropriate sites. The fingercot was examined after each application to ensure that the test products did not adhere to the fingercot. The post-baseline (treatment) value was established by three readings of the skin's conductivity value in each of the six test sites at five separate time points. Changes in skin hydration or moisturization values were determined by subtracting the average baseline skin conductivity value measured prior to treatment from the average post-baseline (treatment) skin conductivity value measured at the five separate time points. Hydration or moisturization enhancement values and percent changes were then calculated.

Example 12

Clinical Evaluation of the Efficacy of Test Product 7 Mixture Containing 2% PEG-16 Macadamia Glycerides and DI Water (Rinse-Off Study)

Clinical studies were conducted according to the general procedure described in Example 11 herein above. Under conditions of the study, a total of 19 healthy female subjects, 38-64 years of age, completed the clinical study evaluating the efficacy of a mixture containing 2% PEG-16 Macadamia Glycerides oil and DI water. An explanation of the contents of the mixtures used in this Example 12 is shown in Table 18. A summary of key clinical findings is shown in Table 19.

TABLE 18

Experimental mixture contents.

| Mixture Type | Contents |
|---|---|
| Placebo Control 7 | 100% DI water |
| Test Product 7 | 98.0% DI water and 2.0% PEG-16 Macadamia Glycerides |

TABLE 19

Average post-treatment differences in skin hydration or moisturization relative to the average baseline value. Positive differences indicate increases in skin hydration/moisturization.

| Parameter | 30 Minute | 1 Hour | 2 Hour | 4 Hour | 8 Hour |
|---|---|---|---|---|---|
| Mean % Difference from Baseline (Placebo Control 7 Site) | −0.20% | −0.23% | −0.32% | −0.37% | −0.46% |
| % of Subjects Improved (Placebo Control 7 Site) | 21.05% | 26.32% | 42.11% | 31.58% | 42.11% |
| Mean % Difference from Baseline (Test Product 7) | 27.61% | 35.79% | 29.80% | 20.60% | 13.13% |
| % of Subjects Improved (Test Product 7) | 100.00% | 100.00% | 100.00% | 100.00% | 84.21% |

Clinical Findings:

As shown in Table 19, there was an improvement in skin hydration/moisturization for Test Product 7 (defined as 2% PEG-16 Macadamia Glycerides and 98% DI water) after a single application to treated subject's skin at the 30 minute, 1 hour, 2 hour, 4 hour, and 8 hour post-treatment intervals, when compared to the average baseline value. In particular, a 27.61%, 35.79%, 29.80%, 20.60% and 13.13% increase in skin hydration/moisturization was observed, on average, in treated subjects at the 30-min, 1-hr, 2-hr, 4-hr, and 8-hr time points, respectively.

A number of subjects demonstrated improvement in skin hydration/moisturization for the Test Product 7 site at the 30 minute, 1 hour, 2 hour, 4 hour, and 8 hour post-treatment intervals. In particular, 100% of the treated subjects displayed an improvement in skin hydration/moisturization at the 30-min, 1-hr, 2-hr, and 4-hr post-treatment intervals, and 84.21% of the treated subjects displayed an improvement in skin hydration/moisturization at the 8-hr post-treatment interval.

These results demonstrate that mixtures containing 2% PEG-16 Macadamia Glycerides and 98% DI water hydrate/moisturize the skin, and are more effective at hydrating or moisturizing skin than DI water alone.

TABLE 20

Post-treatment differences in skin hydration/moisturization relative to Test Product 7 (2% PEG 16 Macadamia Glycerides and 98% DI water) versus Placebo Control 7 site (DI water only). A positive difference indicates that the Test Product 7 site was more hydrated/moisturized than the Placebo Control 7 site (DI water only).

| Comparison (%ΔTest Product 7-%ΔPlacebo Control 7) | Interval | Variation Mean % |
|---|---|---|
| Test Product 7-Placebo Control 7 | 30 Minute | 27.81% |
| Test Product 7-Placebo Control 7 | 1 Hour | 36.02% |
| Test Product 7-Placebo Control 7 | 2 Hour | 30.13% |
| Test Product 7-Placebo Control 7 | 4 Hour | 20.97% |
| Test Product 7-Placebo Control 7 | 8 Hour | 13.59% |

Clinical Findings:

As shown in Table 20, the treatment site for Test Product 7 (again, defined as 2% PEG-16 Macadamia Glycerides and DI water) was more hydrated/moisturized than the Placebo Control 7 site (DI water only) when the percent average change in the Placebo Control 7 site value is subtracted from the percent average change in the Test Product 7 site value at the 30 minute, 1 hour, 2 hour, 4 hour, and 8 hour post-treatment intervals.

Conclusion:

This Example 12 thus provides evidence that a mixture of DI water and PEG-16 Macadamia Glycerides hydrates/moisturizes the skin more effectively than DI water alone.

Example 13

Clinical Evaluation of the Efficacy of Test Product 8 Mixture Containing 2% PEG-16 Macadamia Glycerides and Nestlé® "Pure Life"® Purified (Bottled) Water (Rinse-Off Study)

Clinical studies were conducted according to the general procedure described in Example 11 herein above. Under conditions of the study, a total of 19 healthy female subjects, 38-64 years of age, completed the clinical study evaluating the efficacy of a mixture containing 2% PEG-16 Macadamia Glycerides oil and Nestlé® "Pure Life"® Purified (bottled) Water. An explanation of the contents of the mixtures used in this Example 13 is shown in Table 21. A summary of key clinical findings is shown in Table 22.

TABLE 21

Experimental mixture contents.

| Mixture Type | Contents |
|---|---|
| Placebo Control 8 | 100% Nestlé ® "Pure Life"® Purified (bottled) Water |
| Test Product 8 | 98.0% Nestlé ® "Pure Life"® Purified (bottled) Water and 2.0% PEG-16 Macadamia Glycerides |

TABLE 22

Average post-treatment differences in skin hydration or
moisturization relative to the average baseline value.
Positive differences indicate increases in skin
hydration/moisturization.

| Parameter | 30 Minute | 1 Hour | 2 Hour | 4 Hour | 8 Hour |
|---|---|---|---|---|---|
| Mean % Difference from Baseline (Placebo Control 8 Site) | −0.46% | −0.72% | −0.78% | −0.86% | −0.99% |
| % of Subjects Improved (Placebo Control 8 Site) | 15.79% | 21.05% | 21.05% | 26.32% | 15.79% |
| Mean % Difference from Baseline (Test Product 8) | 29.96% | 34.24% | 29.65% | 17.10% | 10.71% |
| % of Subjects Improved (Test Product 8) | 100.00% | 100.00% | 100.00% | 94.74% | 78.95% |

Clinical Findings:

As shown in Table 22, there was an improvement in skin hydration/moisturization for Test Product 8 (defined as 2% PEG-16 Macadamia Glycerides and 98% Nestlé® "Pure Life"® Purified (bottled) Water) after a single application to treated subject's skin at the 30 minute, 1 hour, 2 hour, 4 hour, and 8 hour post-treatment intervals, when compared to the average baseline value. In particular, a 29.96%, 34.24%, 29.65%, 17.10% and 10.71% increase in skin hydration/moisturization was observed, on average, in treated subjects at the 30-min, 1-hr, 2-hr, 4-hr, and 8-hr time points, respectively.

A number of subjects demonstrated improvement in skin hydration/moisturization for the Test Product 8 site at the 30 minute, 1 hour, 2 hour, 4 hour, and 8 hour post-treatment intervals. In particular, 100% of the treated subjects displayed an improvement in skin hydration/moisturization at the 30-min, 1-hr, and 2-hr post-treatment intervals, while 94.74% and 78.95% of the treated subjects displayed an improvement in skin hydration/moisturization at the 4-hr and 8-hr post-treatment intervals, respectively.

These results demonstrate that mixtures containing 2% PEG-16 Macadamia Glycerides and 98% Nestlé® "Pure Life"® Purified (bottled) Water hydrate/moisturize the skin, and are more effective at hydrating or moisturizing skin than Nestlé® "Pure Life"® Purified (bottled) Water alone.

TABLE 23

Post-treatment differences in skin hydration/moisturization
relative to Test Product 8 (2% PEG 16 Macadamia Glycerides
and 98% Nestlé ® "Pure Life"® Purified
(bottled) Water) versus Placebo Control 8 site (100% Nestlé ® "Pure
Life"® Purified (bottled) Water only). A positive difference
indicates that the Test Product 8 site was more hydrated/
moisturized than the Placebo Control 8 site (100%
Nestlé ® "Pure Life"® Purified (bottled) Water only).

| Comparison (%ΔTest Product 8-%ΔPlacebo Control 8) | Interval | Variation Mean % |
|---|---|---|
| Test Product 8-Placebo Control 8 | 30 Minute | 30.42% |
| Test Product 8-Placebo Control 8 | 1 Hour | 34.96% |
| Test Product 8-Placebo Control 8 | 2 Hour | 30.43% |
| Test Product 8-Placebo Control 8 | 4 Hour | 17.96% |
| Test Product 8-Placebo Control 8 | 8 Hour | 11.70% |

Clinical Findings:

As shown in Table 23, the treatment site for Test Product 8 (again, defined as 2% PEG-16 Macadamia Glycerides and Nestlé® "Pure Life"® Purified (bottled) Water) was more hydrated/moisturized than the Placebo Control 8 site (Nestlé® "Pure Life"® Purified (bottled) Water only) when the percent average change in the Placebo Control 8 site value is subtracted from the percent average change in the Test Product 8 site value at the 30 minute, 1 hour, 2 hour, 4 hour, and 8 hour post-treatment intervals.

Conclusion:

This Example 13 thus provides evidence that a mixture of Nestlé® "Pure Life"® Purified (bottled) Water and PEG-16 Macadamia Glycerides hydrates/moisturizes the skin more effectively than Nestlé® "Pure Life"® Purified (bottled) Water alone.

Example 14

Clinical Evaluation of the Efficacy of Test Product 9 Mixture Containing 2% PEG-16 Macadamia Glycerides and Fiji® Natural Artesian (Bottled) Water (Rinse-Off Study)

Clinical studies were conducted according to the general procedure described in Example 11 herein above. Under conditions of the study, a total of 19 healthy female subjects, 38-64 years of age, completed the clinical study evaluating the efficacy of a mixture containing 2% PEG-16 Macadamia Glycerides oil and Fiji® Natural Artesian (bottled) Water. An explanation of the contents of the mixtures used in this Example 14 is shown in Table 24. A summary of key clinical findings is shown in Table 25.

TABLE 24

Experimental mixture contents.

| Mixture Type | Contents |
|---|---|
| Placebo Control 9 | 100% Fiji ® Natural Artesian (bottled) Water |
| Test Product 9 | 98.0% Fiji ® Natural Artesian (bottled) Water and 2.0% PEG-16 *Macadamia* Glycerides |

TABLE 25

Average post-treatment differences in skin hydration or moisturization
relative to the average baseline value. Positive differences indicate
increases in skin hydration/moisturization.

| Parameter | 30 Minute | 1 Hour | 2 Hour | 4 Hour | 8 Hour |
|---|---|---|---|---|---|
| Mean % Difference from Baseline (Placebo Control 9 Site) | −0.15% | −0.33% | −0.42% | −0.65% | −0.45% |
| % of Subjects Improved (Placebo Control 9 Site) | 31.58% | 36.84% | 36.84% | 42.11% | 52.63% |
| Mean % Difference from Baseline (Test Product 9) | 37.21% | 35.82% | 29.70% | 22.04% | 14.58% |
| % of Subjects Improved (Test Product 9) | 100.00% | 100.00% | 89.47% | 94.74% | 89.47% |

Clinical Findings:

As shown in Table 25, there was an improvement in skin hydration/moisturization for Test Product 9 (defined as 2%

PEG-16 Macadamia Glycerides and 98% Fiji® Natural Artesian (bottled) Water) after a single application to treated subject's skin at the 30 minute, 1 hour, 2 hour, 4 hour, and 8 hour post-treatment intervals, when compared to the average baseline value. In particular, a 37.21%, 35.82%, 29.70%, 22.04% and 14.58% increase in skin hydration/moisturization was observed, on average, in treated subjects at the 30-min, 1-hr, 2-hr, 4-hr, and 8-hr time points, respectively.

TABLE 26

Average post-treatment differences in skin hydration or moisturization relative to the average baseline value for Test Products 7-9. Positive differences indicate increases in skin hydration/moisturization.

| Parameter | 30 Minute | 1 Hour | 2 Hour | 4 Hour | 8 Hour |
|---|---|---|---|---|---|
| Mean % Difference from Baseline (Test Product 7) | 27.61% | 35.79% | 29.80% | 20.60% | 13.13% |
| Mean % Difference from Baseline (Test Product 8) | 29.96% | 34.24% | 29.65% | 17.10% | 10.71% |
| Mean % Difference from Baseline (Test Product 9) | 37.21% | 35.82% | 29.70% | 22.04% | 14.58% |

As shown in Table 26, the increase skin hydration/moisturization shown for Test Product 9 was greater than the increase in skin hydration/moisturization shown for Test Product 7 at three post-treatment intervals (e.g., at the 30-min, 4-hr, and 8-hr time points, respectively), and essentially equivalent at the other two post-treatment intervals (e.g., at the 1-hr and 2-hr time points, respectively). In addition, the increase in skin hydration/moisturization shown for Test Product 9 was greater than the increase in skin hydration/moisturization shown for Test Product 8 at four post-treatment intervals (e.g., at the 30-min, 1-hr, 4-hr, and 8-hr time points, respectively), and essentially equivalent at the remaining post-treatment interval (e.g., at the 2-hr time point).

As further shown in Table 25, a number of subjects demonstrated improvement in skin hydration/moisturization for the Test Product 9 site at the 30 minute, 1 hour, 2 hour, 4 hour, and 8 hour post-treatment intervals. In particular, 100% of the treated subjects displayed an improvement in skin hydration/moisturization at the 30-min and 1-hr post-treatment intervals, while 89.47%, 94.74% and 89.47% of the treated subjects displayed an improvement in skin hydration/moisturization at the 2-hr, 4-hr and 8-hr post-treatment intervals, respectively.

These results demonstrate that mixtures containing 2% PEG-16 Macadamia Glycerides and 98% Fiji® Natural Artesian (bottled) Water hydrate/moisturize the skin, and are more effective at hydrating or moisturizing skin than Fiji® Natural Artesian (bottled) Water alone. In addition and unexpectedly, the type of water used matters: mixtures containing 2% PEG-16 Macadamia Glycerides and 98% Fiji® Natural Artesian (bottled) Water hydrate/moisturize the skin more effectively than mixtures containing 2% PEG-16 Macadamia Glycerides and DI water, or mixtures containing 2% PEG-16 Macadamia Glycerides and Nestlé® "Pure Life"® Purified (bottled) Water.

TABLE 27

Post-treatment differences in skin hydration/moisturization relative to Test Product 9 (2% PEG-16 *Macadamia* Glycerides and 98% Fiji ® Natural Artesian (bottled) Water) versus Placebo Control 9 site (100% Fiji ® Natural Artesian (bottled) Water alone). A positive difference indicates that the Test Product 9 site was more hydrated/moisturized than the Placebo Control 9 site (100% Fiji ® Natural Artesian (bottled) Water alone).

| Comparison (%ΔTest Product 9-%ΔPlacebo Control 9) | Interval | Variation Mean % |
|---|---|---|
| Test Product 9-Placebo Control 9 | 30 Minute | 37.36% |
| Test Product 9-Placebo Control 9 | 1 Hour | 36.15% |
| Test Product 9-Placebo Control 9 | 2 Hour | 30.12% |
| Test Product 9-Placebo Control 9 | 4 Hour | 22.69% |
| Test Product 9-Placebo Control 9 | 8 Hour | 15.03% |

Clinical Findings:

As shown in Table 27, the treatment site for Test Product 9 (again, defined as 2% PEG-16 Macadamia Glycerides and Fiji® Natural Artesian (bottled) Water) was more hydrated/moisturized than the Placebo Control 9 site (Fiji® Natural Artesian (bottled) Water only) when the percent average change in the Placebo Control 9 site value is subtracted from the percent average change in the Test Product 9 site value at the 30 minute, 1 hour, 2 hour, 4 hour, and 8 hour post-treatment intervals.

Conclusion:

This Example 14 thus provides evidence that a mixture of Fiji® Natural Artesian (bottled) Water and PEG-16 Macadamia Glycerides hydrates/moisturizes the skin more effectively than Fiji® Natural Artesian (bottled) Water alone.

Example 15

Evaluation of Particle Attributes

This Example 15 describes general procedures developed to evaluate various characteristics of mixtures described herein. Test Products 7 through 9 and Placebo Controls 7 through 9 are identical to those described in Examples 11 through 14, respectively.

Attributes of Test Product 7, Placebo Control 7, Test Product 8, Placebo Control 8, Test Product 9, and Placebo Control 9 were evaluated, as well as the attributes of PEG-16 Macadamia Glycerides only. Specifically, particle size, surface tension, and spreading were measured for Test Product 7, Placebo Control 7, Test Product 8, Placebo Control 8, Test Product 9, Placebo Control 9, and PEG-16 Macadamia Glycerides (only).

The particle size was determined using a Malvern Nano-Sizer 90Z. Each formulation was run three times and the data averaged. The sample Count Rate and Duration was set automatically by the instrument.

Surface tension measurements were made using the Krüss DSA10 via the Pendant Drop Method (LaPlace-Young equation for fit). Each formulation was run four times and the data averaged.

The degree of spreading was determined manually via microscopic examination (Zeiss model Std 25 fitted with a 40× objective). A 20 μL drop of each formulation was placed on a horizontal anodized aluminum plate using an Eppendorf pipette. A photograph was taken at time zero and after 5 minutes. Using a calibrated graticule, the diameter of the drop at each time point was determined. Each formulation was measured four times and the data averaged. The average error on timing was determined to be +/−4 seconds.

Example 16

Particle Size Measurements

Measurements of the particle size were measured for Test Products 7-9 and Placebo Controls 7-9. The results for intensity-weighted particle size distribution (PSD) measurements are shown in Table 28.

TABLE 28

Intensity-Weighted Representative PSD results.

| Mixture Type | Particle Size (nano meters) | | |
|---|---|---|---|
| | $Z_{Avg}$ | Peak* | Polydispersity Index (PdI) |
| Test Product 7 | 12.31 | 13.77 | 0.117 |
| Placebo Control 7 | 176.4 | 16.54 | 0.554 |
| Test Product 8 | 26.72 | 11.97 | 0.200 |
| Placebo Control 8 | 62.74 | 10.16 | 0.369 |
| Test Product 9 | 58.15 | 13.25 | 0.211 |
| Placebo Control 9 | N/A** | N/A** | N/A** |

*Main mode
**N/A - Not Applicable: count rate too low for measurement

Findings:

As shown in Table 28, Test Products 7 and 8 show a smaller $Z_{Avg}$ particle size versus their respective placebo controls (Placebo Control 7 and Placebo Control 8, respectively). Whereas, Test Product 9 shows a higher $Z_{Avg}$ particle size versus its placebo control (Placebo Control 9).

Conclusion:

This Example 16 demonstrates that a mixture of PEG-16 Macadamia Glycerides and DI Water contains smaller particles than the particles created by a mixture of PEG-16 Macadamia Glycerides and Nestlé® "Pure Life"® Purified (bottled) Water. Similarly, Example 16 demonstrates that a mixture of PEG-16 Macadamia Glycerides and DI Water contains smaller particles than the particles created by a mixture of PEG-16 Macadamia Glycerides and Fiji® Natural Artesian (bottled) Water. In addition, a mixture of PEG-16 Macadamia Glycerides and DI Water contains smaller particles than the particles created from DI Water alone. Similarly, Example 16 demonstrates that a mixture of PEG-16 Macadamia Glycerides and Nestlé® "Pure Life"® Purified (bottled) Water contains smaller particles than the particles created from Nestlé® "Pure Life"® Purified (bottled) Water alone. Example 16 further demonstrates that a mixture of PEG-16 Macadamia Glycerides and Fiji® Natural Artesian (bottled) Water contains larger particles than the particles created from Fiji® Natural Artesian (bottled) Water alone.

Example 17

Surface Tension Measurements

Measurements of the surface tension were measured for Test Products 7-9, Placebo Controls 7-9, and PEG-16 Macadamia Glycerides only. The results are shown in Table 29.

TABLE 29

Surface tension results.

| Mixture Type | Surface Tension (mN/m) |
|---|---|
| Test Product 7 | 38 |
| Placebo Control 7 | 68 |
| Test Product 8 | 38 |
| Placebo Control 8 | 63 |
| Test Product 9 | 37 |
| Placebo Control 9 | 70 |
| PEG-16 Macadamia Glycerides | 31 |

Findings:

As shown in Table 29, Test Products 7-9 each have lower surface tension values than their respective Placebo Controls. The surface tension of PEG-16 Macadamia Glycerides only is slightly less than the surface tension of Test Products 7-9, respectively.

Conclusion:

This Example 17 demonstrates that mixtures of either DI Water and PEG-16 Macadamia Glycerides, Nestlé® "Pure Life"® Purified (bottled) Water and PEG-16 Macadamia Glycerides, or Fiji® Natural Artesian (bottled) Water and PEG-16 Macadamia Glycerides, respectively, have lower surface tension values than DI Water, Nestlé® "Pure Life"® Purified (bottled) Water, and Fiji® Natural Artesian (bottled) Water by themselves, respectively. Example 17 further demonstrates that mixtures of either DI Water and PEG-16 Macadamia Glycerides, Nestlé® "Pure Life"® Purified (bottled) Water and PEG-16 Macadamia Glycerides, or Fiji® Natural Artesian (bottled) Water and PEG-16 Macadamia Glycerides, respectively, have a slightly higher surface tension value than PEG-16 Macadamia Glycerides alone.

Example 18

Spreading Measurements

Spreading measurements were measured for Test Products 7-9, Placebo Controls 7-9, and PEG-16 Macadamia Glycerides only. Measurements were taken at 0 minutes and 5 minutes. The results are shown in Table 30.

TABLE 30

Spreading on a planar surface results.

| Mixture Type | Drop Diameter (mm) at Time = 0 | Drop Diameter (mm) at Time = 5 minutes | Difference |
|---|---|---|---|
| Test Product 7 | 7.17 | 7.43 | 0.26 |
| Placebo Control 7 | 5.04 | 5.04 | 0 |
| Test Product 8 | 5.62 | 6.41 | 0.79 |
| Placebo Control 8 | 4.76 | 4.81 | 0.05 |
| Test Product 9 | 5.47 | 6.19 | 0.72 |
| Placebo Control 9 | 5.14 | 5.14 | 0 |
| PEG-16 Macadamia Glycerides | 6.79 | 7.29 | 0.5 |

Findings:

As shown in Table 30, Test Products 8 and 9 spread the most readily of all the mixture types tested. Test Product 7 spread, but to a lesser degree versus Test Products 8 and 9. Test Products 8 and 9 spread more readily than PEG-16 Macadamia Glycerides only, while Test Product 7 spread less readily than PEG-16 Macadamia Glycerides only. Placebo Controls 7 and 9 did not spread at all, while the spread of Placebo Control 8 was minimal.

Conclusion:

This Example 18 demonstrates that mixtures of Nestlé® "Pure Life"® Purified (bottled) Water and PEG-16 Macadamia Glycerides, or Fiji® Natural Artesian (bottled) Water and PEG-16 Macadamia Glycerides spread more readily than a mixture of DI Water and PEG-16 Macadamia Glycerides, and spread more readily than PEG-16 Macadamia Glycerides alone. Example 18 further demonstrates that mixtures of either Nestlé® "Pure Life"® Purified (bottled) Water and PEG-16 Macadamia Glycerides, or Fiji® Natural Artesian (bottled) Water and PEG-16 Macadamia Glycerides spread more readily than DI Water only, Nestlé® "Pure Life"® Purified (bottled) Water only, Fiji® Natural Artesian (bottled) Water only, or PEG-16 Macadamia Glycerides only, respectively.

Taken in combination, Examples 16 through 18 demonstrate that mixtures of Nestlé® "Pure Life"® Purified (bottled) Water and PEG-16 Macadamia Glycerides, or Fiji® Natural Artesian (bottled) Water and PEG-16 Macadamia Glycerides have unexpected physical advantages over mixtures of DI Water and PEG-16 Macadamia Glycerides, namely increased spreadability, thus increasing the bioavailability of water to the skin.

What is claimed is:

1. A method for enhancing hydration or moisturization of the skin of a subject comprising:
   mixing water and an ethoxylated oil to generate a nanoemulsion prior to the addition of an additional compound or component to said water and/or ethoxylated oil;
   mixing-in a combined mixture of phenoxyethanol, caprylyl glycol, ethylhexylglycerin and hexylene glycol to create a composition; and
   topically administering to the skin of the subject the composition comprising said nanoemulsion, wherein said nanoemulsion consists of ethoxylated oil and water, wherein the average number of ethoxylations per molecule in the ethoxylated oil is 10-19 and, wherein said nanoemulsion contains nano-sized micelles having a mean or average diameter that is greater than zero microns but not more than 0.5 microns.

2. The method of claim 1, wherein the ethoxylated oil is selected from the group consisting of macadamia nut oil, oleic acid, palmitoleic acid, apricot kernel oil, avocado oil, evening primrose oil, grape seed oil, hazelnut oil, pumpkinseed oil, rosehip oil, safflower oil, sunflower oil, walnut oil, wheat germ oil, neem oil, mink oil, lanolin, argan oil, Abyssinian oil, *Salvia Hispanica* oil (chia seed oil), Calophyllum Tacamahaca Seed oil (tamanu oil), squalane, sea buckthorn oil, meadowfoam oil, castor oil, jojoba oil, olive oil, corn oil, sesame oil, oenocarpus bataua oil, pentaclethra macroloba oil, and emu oil, or any combination therein.

3. The method of claim 1, wherein the amount of ethoxylated oil in the composition is 0.1%, 0.5%, 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by volume or weight or a percentage that is within a range defined by any two of the aforementioned percentages.

4. The method of claim 1, wherein the composition further comprises an essential oil, pigment, or fragrance.

5. The method of claim 1, wherein the composition is administered to said subject by adding the composition to a reservoir of water, contained in a container, mixing vessel, mixing tank, mixing kettle, water softener system, water purification system, water filtration system, drinking water system, drinking fountain, swimming pool, pool, whirlpool, steam room, sauna, storage tank, sink, bath, tub or shower, or metering the composition in-line, in real time, to flowing water.

6. The method of claim 1, further comprising determining skin hydration or moisturization in the subject after administration of the composition and, wherein said determining skin hydration or moisturization comprises determining an electromagnetic radiation, a dielectric constant, a dielectric permittivity, a thermal conductivity, or an elastographic parameter of said skin.

7. The method of claim 1, further comprising determining skin hydration or moisturization in the subject after administration of the composition and, wherein said determining skin hydration or moisturization comprises determining a water evaporation gradient or an electrical property of the skin, by capacitance, conductance, impedance, alternating current conductivity on the skin surface, transepidermal water loss (TEWL), attenuated total reflectance Fourier transform infrared (ATR-FTIR), confocal raman spectroscopy, optical fiber near infrared (NIR) spectroscopy, electron microscopy, or Fourier transform near-infrared (FT-NIR) spectrophotometry.

8. The method of claim 1, wherein the composition is formulated with or into a base, a functional ingredient, a functional ingredient blend, an active ingredient, an active ingredient blend, a bar soap, a liquid soap, a hand soap, a body soap, a body wash, a shower gel, a bubble bath, a dissolvable bead, a bath bead, a shaving cream, a shaving gel, an aftershave, a deodorant, an antiperspirant, an acne treatment formula, a lip care formula, a lip plumper, a face care formula, a facial moisturizer, a facial cleanser, a facial wash, a facial toner, a facial astringent, a facial clarifier, a facial mist, a facial spray, a facial mask, a facial exfoliator, a facial wipe, a color cosmetic, a makeup remover, a makeup foundation, a makeup concealer, or a sprayable makeup setting agent, a skincare formula, a sun care formula, an after sun formula, a foot care formula, a hand care formula, a shampoo, a hair conditioner, a hair care formula, a hair spray, a hair styling product, a scalp care formula, a self-tanner formula, a body care formula, a body moisturizer, a body spray, a body scrub, a body cleanser, a body exfoliator, or a body wipe, a depilatory, a perfume, an eau de parfum, an eau de toilette, an eau de cologne, a dish soap, a laundry detergent, a pain relief formula, a toothpaste, a teeth cleaning formula, a lozenge, a mouthwash, a first aid product, a skin ailment product, a compromised skin product, an antiseptic product, an insect bite product, a blister relief product, a bunion relief product, a callus relief product, a feminine care product, an anti-itching product, an anti-rash product, an anti-fungal product, a pet care product, a pet grooming product, a wound healing product, a burn relief product, a scar management product, a stretch mark product, a wart removal product, a hand sanitizer, a cold sore care product, an anti-cellulite product, an eye drop or spray, a nasal drop or spray, an ear drop or spray, a mouth drop or spray, a personal lubricant, a diaper product, a leave-on product, a rinse-off or wash-off product, a pharmaceutical preparation, a dietary supplement, a personal care preparation, or a cosmetic preparation.

9. The method of claim 1, wherein said water is selected from the group consisting of drinking water, bottled water, sparkling water, sparkling mineral water, alkaline water, glacial water, coconut water, carbonated water, purified drinking water, natural water, spring water, natural spring water, artesian water, natural artesian water, mineral water, natural mineral water, and any mixtures thereof.

10. The method of claim 2, wherein the ethoxylated oil is macadamia nut oil.

11. The method of claim 10, wherein the macadamia nut oil is macadamia nut oil with 16 ethoxylations per molecule.

12. The method of claim 1, wherein the nano-sized micelles have a mean or average diameter that is greater than zero microns but not more than 0.04 microns.

13. The method of claim 1, wherein the nano-sized micelles have a mean or average diameter that is greater than zero microns but not more than 0.01 microns.

* * * * *